(12) United States Patent
Giese et al.

(10) Patent No.: US 10,502,750 B2
(45) Date of Patent: Dec. 10, 2019

(54) RELIABLE AND ROBUST METHOD FOR THE ANALYSIS OF CANNABINOIDS AND TERPENES IN CANNABIS

(71) Applicant: Biotech Institute, LLC, Westlake Village, CA (US)

(72) Inventors: Matthew W. Giese, Westlake Village, CA (US); Mark Anthony Lewis, Westlake Village, CA (US); Laura Giese, Westlake Village, CA (US)

(73) Assignee: Biotech Institute, LLC, Westlake Village, CA (US)

( * ) Notice: Subject to any disclaimer, the term of this patent is extended or adjusted under 35 U.S.C. 154(b) by 183 days.

(21) Appl. No.: 15/539,344

(22) PCT Filed: Dec. 23, 2015

(86) PCT No.: PCT/US2015/000263
§ 371 (c)(1),
(2) Date: Jun. 23, 2017

(87) PCT Pub. No.: WO2016/105514
PCT Pub. Date: Jun. 30, 2016

(65) Prior Publication Data
US 2018/0143212 A1    May 24, 2018

Related U.S. Application Data

(60) Provisional application No. 62/095,827, filed on Dec. 23, 2014, provisional application No. 62/249,583, filed on Nov. 2, 2015.

(51) Int. Cl.
| | |
|---|---|
| *G01N 33/94* | (2006.01) |
| *G01N 30/06* | (2006.01) |
| *G01N 30/68* | (2006.01) |
| *G01N 21/3554* | (2014.01) |
| *B01D 11/02* | (2006.01) |
| *B01D 15/08* | (2006.01) |
| *B01D 53/02* | (2006.01) |
| *A61K 36/185* | (2006.01) |
| *G01N 30/04* | (2006.01) |
| *G01N 21/35* | (2014.01) |
| *G01N 30/02* | (2006.01) |

(52) U.S. Cl.
CPC ......... *G01N 33/948* (2013.01); *A61K 36/185* (2013.01); *B01D 11/0288* (2013.01); *B01D 15/08* (2013.01); *B01D 53/025* (2013.01); *G01N 21/3554* (2013.01); *G01N 30/06* (2013.01); *G01N 30/68* (2013.01); *A61K 2236/00* (2013.01); *G01N 2021/3595* (2013.01); *G01N 2030/025* (2013.01); *G01N 2030/027* (2013.01); *G01N 2030/042* (2013.01); *G01N 2333/415* (2013.01); *G01N 2407/00* (2013.01)

(58) Field of Classification Search
CPC .............. A61K 2236/00; A61K 36/185; B01D 11/0288; B01D 15/08; B01D 53/025; G01N 2021/3595; G01N 2030/025; G01N 2030/027; G01N 2030/042; G01N 21/3554; G01N 2333/415; G01N 2407/00; G01N 30/06; G01N 30/68; G01N 33/94; G01N 33/948; Y10T 436/142222; Y10T 436/20; Y10T 436/203332; Y10T 436/204165; Y10T 436/21; Y10T 436/212; Y10T 436/255; Y10T 436/25625
USPC ......... 436/93, 127, 131, 132, 139, 140, 161, 436/178, 179, 901; 422/70, 89
See application file for complete search history.

(56) References Cited

U.S. PATENT DOCUMENTS

| | | |
|---|---|---|
| 4,279,824 A | 7/1981 | McKinney |
| 5,532,131 A | 7/1996 | Lewis |
| 5,757,659 A | 5/1998 | Arai et al. |
| 6,403,126 B1 | 6/2002 | Webster et al. |
| 6,439,027 B1 | 8/2002 | Hiss |
| 6,466,929 B1 | 10/2002 | Brown et al. |
| 6,630,507 B1 | 10/2003 | Hampson et al. |
| 7,117,188 B2 | 10/2006 | Guyon et al. |
| 7,968,594 B2 | 6/2011 | Guy et al. |
| 8,402,027 B1 | 3/2013 | Dange et al. |
| 9,095,554 B2 | 8/2015 | Lewis et al. |
| 9,370,164 B2 | 6/2016 | Lewis et al. |
| 9,642,317 B2 | 5/2017 | Lewis et al. |
| 2004/0049059 A1 | 3/2004 | Mueller |
| 2005/0266108 A1 | 12/2005 | Flockhart et al. |
| 2006/0100245 A1 | 5/2006 | Bakthavatchalam et al. |
| 2006/0160888 A1 | 7/2006 | Kottayil et al. |
| 2008/0103193 A1 | 5/2008 | Castor et al. |
| 2008/0241339 A1 | 10/2008 | Mitchell et al. |

(Continued)

FOREIGN PATENT DOCUMENTS

| | | |
|---|---|---|
| GB | 2459125 A | 10/2009 |
| WO | WO 2011/110866 A1 | 9/2011 |

(Continued)

OTHER PUBLICATIONS

Giese et al. Journal of AOAC International, vol. 98, No. 6, 2015, pp. 1503-1522.*

(Continued)

*Primary Examiner* — Maureen Wallenhorst
(74) *Attorney, Agent, or Firm* — Cooley LLP

(57) ABSTRACT

The present invention teaches methods useful for accurately and precisely analyzing cannabis plants, plant parts, and extract samples. In particular, the present invention teaches methods of extracting, and quantifying cannabinoid and terpene constituents.

20 Claims, 39 Drawing Sheets

(56) References Cited

U.S. PATENT DOCUMENTS

| | | |
|---|---|---|
| 2009/0035396 A1 | 2/2009 | De Meijer |
| 2010/0216872 A1 | 8/2010 | Letzel et al. |
| 2011/0098348 A1 | 4/2011 | De Meijer |
| 2011/0320135 A1 | 12/2011 | van de Voort et al. |
| 2012/0052535 A1* | 3/2012 | Lange .................. C12N 9/88 435/125 |
| 2012/0311744 A1 | 12/2012 | Sirkowski |
| 2013/0109747 A1 | 5/2013 | Whittle |
| 2014/0088884 A1 | 3/2014 | Friedenberg et al. |
| 2014/0243405 A1 | 8/2014 | Whalley |
| 2014/0245494 A1 | 8/2014 | Cohen |
| 2014/0245495 A1 | 8/2014 | Cohen |
| 2014/0271940 A1 | 9/2014 | Wurzer |
| 2014/0287068 A1 | 9/2014 | Lewis et al. |
| 2014/0298511 A1 | 10/2014 | Lewis |
| 2014/0324660 A1 | 10/2014 | Bolno et al. |
| 2015/0359188 A1 | 12/2015 | Lewis et al. |
| 2015/0366154 A1 | 12/2015 | Lewis et al. |
| 2016/0324091 A1 | 11/2016 | Lewis et al. |
| 2017/0202170 A1 | 7/2017 | Lewis et al. |
| 2018/0064055 A1 | 3/2018 | Lewis et al. |
| 2018/0224411 A1* | 8/2018 | Raber .................. A61K 31/352 |
| 2018/0284145 A1* | 10/2018 | Giese .................. G01N 33/948 |

FOREIGN PATENT DOCUMENTS

| | | |
|---|---|---|
| WO | WO 2013/155553 A1 | 10/2013 |
| WO | WO 2014/145490 A2 | 9/2014 |
| WO | WO 2015/065544 A1 | 5/2015 |
| WO | WO 2016/105514 A1 | 6/2016 |
| WO | WO 2016/123160 A1 | 8/2016 |

OTHER PUBLICATIONS

Aberl and Coelhan, "Determination of Volatile Compounds in Different Hop Varieties by Headspace-Trap GC/MS—In Comparison with Conventional Hop Essential Oil Analysis." J. Agric. Food Chem. (2012); 60 (11): 2785-2792.

Agilent Technologies, Inc. "Consideration for Selecting GC/MS or LC/MS for Metabiomics", Feb. 24, 2007, 4 pages.

American Herbal Pharmacopoeia, Cannabis Inflorescence and Leaf (2013); AHP, Scott's Valley, CA, 15 pages.

Analytical 360 Analysis of Critical Mass on Aug. 25, 2014, http://analytical360.com/m/expired/276599, 5 pages.

Analytical 360 analysis of Sweet & Sour Widow CBD on Nov. 2, 2013, http://analytical360.com/m/expired/131803, 4 pages.

Analytical 360 Analysis of Sweet n' Sour Widow on May 8, 2014, http://analytical360.com/m/expired/230612, 4 pages.

AOAC® Peer-Verified Methods Program, Manual on Policy and Procedures (1998); Arlington, VA, 35 pages.

Bertoli, A., et al., "Fibre hemp inflorescences: From crop-residues to essential oil production", Industrial Crops and Products, Nov. 1, 2010, pp. 329-337, vol. 32, No. 3.

Casano et al., "Variations in Terpene Profiles of Different Strains of Cannabis sativa L." Acta Horticulturae, vol. 925, pp. 115-121, 2011.

CBD Crew "About Us" Printed copy provided as published on Apr. 10, 2012. URL: http://cbdcrew.org/about-us/, 3 pages.

CCD Crew "Varieties" printed copy as published on Mar. 20, 2012 URL: http://cbdcrew.org/varieties/, 2 pages.

CBD Crew Analysis Report; (Critical Mass, Fundacion CANNA; Mar. 21, 2012), pp. 1-2, http://cbdcrew.org/varieties/cbd-critical-mass/.

CBD Crew Sweet and Sour Widow analysis published Nov. 2, 2013, pp. 1-5, http://analytical360.com/m/expired/131803.

CBD Crew variety "Sweet and Sour Widow" retrieved from the internet: https://web.archive.org/web/20120409021918/http://cbdcrew.org/varieties/cbd-sweet-and-sour-widow/, published on Apr. 9, 2012, retrieved on Mar. 10, 2017, 2 pages.

CBD Crew Web Pub; (Critical Mass sample available from Northwest Canna Connection; Feb. 26, 2014, pp. 1-5. http://analytical360.com/m/expired/197158.

CBD-crew front page on Nov. 22, 2014. www.cbdcrew.org, 2 pages.

Da Silva, et al., "Biological Activities of a-Pinene and β-Pinene Enantiomers." Molecules (2012); 17(6): 6305-6316.

Davies, et al., "Metabolome variability in crop plant species—When, where, how much and so what?" Regulatory Toxicology and Pharmacology (2010); 58(3-Supplement 1): S54-S61.

De Backer, et al., "Innovative development and validation of an HPLC/DAD method for the qualitative and quantitative determination of major cannabinoids in cannabis plant material." Journal of Chromatography B (2009); 877(32): 4115-4124.

De Meijer and Hammond, "The inheritance of chemical phenotype in Cannabis sativa L. (V): regulation of the propyl-/pentyl cannabinoid ratio, completion of a genetic model." Euphytica (2016); 210: 291-307.

De Meijer et al., 2003, "The Inheritance of Chemical Phenotype in Cannabis sativa L." Genetics, 163: 335-346.

De Meijer et al., 2005, "The Inheritance of Chemical Phenotype in Cannabis sativa L. (II) Cannabigerol Predominant Plants." Euphytica, 145:189-198.

De Meijer et al., 2009, "The Inheritance of chemical phenotype in Cannabis sativa L. (III) Variation in Cannabichromene Proportion", Euphytica, 165:293-311.

De Meijer et al., 2009, "The Inheritance of Chemical Phenotype in Cannabis sativa L. (IV) Cannabinoid-Free Plants", Euphytica, 168:95-112.

Do Vale, et al., "Central effects of citral, myrcene and limonene, constituents of essential oil chemotypes from Lippia alba (Mill.) N.E. Brown." Phytomedicine (2002); 9(8): 709-714.

Dussy, F.E., et al., "Isolation of $\Delta^9$-THCA-A from hemp and analytical aspects concerning the determination of $\Delta^9$-THC in cannabis products." Forensic Science International (2005); 149(a): 3-10.

Elsohly and Gul, "Constituents of Cannabis Sativa." Handbook of Cannabis (R.G. Pertwee (Eds), Oxford University Press, Oxford, UK. pp. 3-22.

Fischedick, J. et al., "Metabolic fingerprinting of Cannabis sativa L., cannabinoids and terpenoids for chemotaxonomic and drug standardization purposes" Phytochemistry 2010, vol. 71., pp. 2058-2073.

G. of Vancouver Island Seed Company, "How to make Clones", Cannabis Culture Magazine published on Tuesday, Apr. 29, 2009, 58 pages. Available online at http://www.cannabisculture.com/content/how-make-clones.

Grotenhermen, F., "Clinical Pharmacokinetics of Cannabinoids." Journal of Cannabis Therapeutics (2002); 3(1): 3-51.

Halent Laboratories "Test Results for Dougie's Farm H0-21", Test ID# 2960-1, Feb. 14, 2013, 5 pages.

Halent Labs Chemical Analysis for "Pineapple Purps" retrieved from the internet: http://steephilllab.com/thcv-the-sports-car-of-cannabinoids/, retrieved on Mar. 17, 2017, 1 page.

Hazekamp, A., Cannabis: Extracting the Medicine, Proefschrift Universiteit Leiden, Amsterdam, The Netherlands, (2007), pp. 91-106, 187 pages.

International PCT Search Report for PCT/US2014/030267, dated Nov. 7, 2014, 6 pages.

International PCT Search Report for PCT/US2014/046694, dated Jan. 5, 2015, 7 pages International Preliminary Report on Patentability for International Application No. PCT/US2014/030267 dated Sep. 15, 2015, 10 pages.

International Preliminary Report on Patentability for International Application No. PCT/US2014/046694 dated May 3, 2016, 11 pages.

International Preliminary Report on Patentability for International Application No. PCT/US2015/000263, dated Jun. 27, 2017, 8 pages.

International Preliminary Report on Patentability for International Application No. PCT/US2016/015011, dated Aug. 1, 2017, 15 pages.

International Search Report and Written Opinion for International Application No. PCT/US2015/000263, dated Mar. 4, 2016, 8 pages.

(56) References Cited

OTHER PUBLICATIONS

International Search Report and Written Opinion for International Application No. PCT/US2016/015011, dated Apr. 8, 2016, 16 pages.
Kojoma, M. et al., "DNA polymorphisms in the tetrahydrocannabinolic acid (THCA) synthase gene in "drug-type" and "fiber-type" *Cannabis sativa* L", Forensic Science International, Jun. 2, 2006, pp. 132-140, vol. 159, No. 2-3, Elsevier Scientific Publishers Ireland Ltd.
Kulkarni and Rathod, "Mapping of an ultrasonic bath for ultrasound assisted extraction of mangiferin from Mangifera indica leaves." Ultrasonics Sonochemistry (2014); 21(2): 606-611.
McPartland and Russo 2001 "Cannabis and Cannabis Extracts: Greater Than the Sum of Their Parts", Journal of Cannabis Therapeutics vol. 1, No. 3/4,2001, pp. 103-132.
Pertwee, RG. 2008 "The diverse $CB_1$ and $CB_2$ receptor pharmacology of three plant cannabinoids: $\Delta^9$ tetrahydrocannabinol, cannabidiol and $\Delta^9$ tetrahydrocannabivarin" Br. J Pharmacol. 153(2):199-215.
Rao, et al., "Effect of myrcene on nociception in mice." Journal of Pharmacy and Pharmacology (1990); 42(12): 877-878.
Restek ChromaBLOGraphy, https://blog.restek.com/?p=11770, Mar. 25, 2014, accessed Oct. 26, 2017, 7 pages.
Russo and Guy, "A tale of two cannabinoids: the therapeutic rationale for combining tetrahydrocannabinol and cannabidiol", Medical Hypothesis, 2006, 66:234-246.
Russo, E.B., "Taming THC: potential cannabis synergy and phytocannabinoid-terpenoid entourage effects" The British Journal of Pharmacology, 2011, pp. 1344-1364, vol. 163.
Satyal, P. et al. "Chemotyping and Determination of Antimicrobial Insecticidal, and Cytotoxic Properties of Wild Grown Cannabis saliva from Nepal" Journal of Medicinally Active Plants, Dec. 2014, vol. #3, Issue 1, pp. 9-16.
Seedsman Listing of "Sweet and Sour Widow", on May 21, 2013, http://web.archive.org/web/20130521045347/http://www.seedsman.com/en/cbd-sweet-n-sour-widow-regular-5-seeds, 3 pages.
Solon, Olivia, "Medical Marijuana Without the High", Jul. 5, 2012, retrieved from the internet: www.wired.com.
Steep Hill Halent Cannabis Analytics and Research: "Dougs Varin Decarb THCV Std.", Steep Hill Labs, Inc., Reported Jun. 10, 2014, retrieved from the internet: http://steephilllab.com/wp-content/uploads/2014/07/DougsVarinKief_Decarbed.pdf, retrieved on Mar. 17, 2017, 3 pages.
Steep Hill Halent Cannabis Analytics and Research: "Dougs Varin THCVA Std.", Steep Hill Labs, Inc., Reported Jun. 10, 2014, retrieved from the internet: http://steephilllab.com/wp-content/uploads/2014/07/DougsVarinKief.pdf, retrieved on Mar. 17, 2017, 3 pages.
Swift, et al., "Analysis of Cannabis Seizures in NSW, Australia: Cannabis Potency and Cannabinoid Profile." PLOS ONE (2013); 7: 1-9.

The Werc Shop Terpene Profiling Services, Aug. 26, 2012. http://web.archive.org/web/20120826071723/http://thewercshop.com/services/terpene-profiling-services, 4 pages.
Van Bakel, et al. "The draft genome and transcriptome of Cannabis sativa", Genome Biology, Oct. 20, 2011, p. R102, vol. 12, No. 10, Biomed Central Ltd., London, GB.
Waksmundzka-Hajnos and Monika, "High Performance Liquid Chromatography in Phytochemical Analysis (Chromatograhic Science Series)." Published May 14, 2012. p. 582 provided.
Written Opinion for International Application No. PCT/US2014/030267 dated Nov. 7, 2014, 9 pages.
Written Opinion for International Application No. PCT/US2014/046694 dated May 1, 2015, 10 pages.
Analytical 360, Test results for "Nordle", Jun. 22, 2013 (Jun. 22, 2013), retrieved from the internet: http://archive.analytical360.com/m/archived/79871, retrieved on May 29, 2019.
Analytical 360, Test results for "Nordle", Jan. 8, 2014 (Jan. 8, 2014), retrieved from the internet: http://archive.analytical360.com/m/archived/166950, retrieved on May 29, 2019.
Analytical 360 Analysis of Girl Scout Cookie (Patient Solutions) on Jun. 23, 2014, https://web.archive.org/web/20140628182810/http://analytical360.com/m/flowers/251990, 3 pages.
Analytical 360 Analysis of Omrita Rx on Feb. 20, 2014, http://archive.analytical360.com/m/archived/192732, 3 pages.
Booth et al., "Terpene synthases from Cannabis sativa," PLoS ONE (2017) 12(3): e0173911, 20 pages.
Elsohly, M.A., et al., Journal of Forensic Sciences, 1984; vol. 29, No. 2, pp. 500-514, 15 pages.
Gieringer, D., "Cannabis "Vaporization": A Promising Strategy for Smoke Harm Reduction." Journal of Cannabis Therapeutics (2001); 1 (3-4): 153-170.
Grotenhermen et al., "The therapeutic potential of cannabis and cannabinoids", Dtsch Arztebl Int., vol. 109, No. 29-30, pp. 495-501, 2012.
Hazekamp and Fischedick, "Cannabis—from cultivar to chemovar", Drug Testing and Analysis, vol. 4, pp. 660-667, 2012, published online Feb. 24, 2012 (Feb. 24, 2012).
Hillig, "A chemotaxonomic analysis of terpenoid variation in Cannabis," Biochemical Systematics and Ecology (2004), 32:875-891.
Ito et al., "The sedative effect of inhaled terpinolene in mice and its structure-activity relationships," Journal of Natural Medicines, 2013, vol. 67, Issue 4, pp. 833-837, published online Jan. 22, 2013 (Jan. 22, 2013).
Klingeren and Ham, "Antibacterial activity of $\Delta^9$-tetrahydrocannabinol and cannabidiol", Antonie van Leeuwenhoek (1976); 42 (1-2): 9-12.
Okumura et al., "Terpinolene, a component of herbal sage, downregulates AKT1 expression in K562 cells", Oncology Letters, vol. 3, pp. 321-324, 2012.
Pertwee, RG., "Emerging strategies for exploiting cannabinoid receptor agonists as medicines." Br J Pharmacol. (2009); 156 (3): 397-411.

\* cited by examiner n-nonane (a), α-pinene (1), camphene (2), β-pinene (3), myrcene (4), α-phellandrene (5), carene (6), α-terpinene (7), cymene (b), limonene (8), cineole (c) cis-B-ocimene (d), trans-B-ocimine (9), γ-terpinene (10), terpinolene (11), linalool (12), fenchol (13), α-terpineol (14), β-caryophyllene (15), α-humulene (16) and caryophyllene oxide (17).

ibuprofen(a), CBDA (1), CBG (2), CBD (3), CBN(4), THC(5), Δ8-THC(6), CBC(7), THCA (8), CBDVA (9), CBDV (10), CBGA (11), THCV (12), THCVA (13)

(a) α-pinene, (b) camphene, (c) β-pinene, (d) myrcene, (e) α-phellandrene,
(f) carene, (g) α-terpinene, (h) limonene, (i) B–ocimine, (j) γ-terpinene,
(k) terpinolene, (l) linalool, (m) fenchol, (n) α-terpineol, (o) β-caryophyllene,
(p) α-humulene, (q) caryophyllene oxide.

RELIABLE AND ROBUST METHOD FOR THE ANALYSIS OF CANNABINOIDS AND TERPENES IN CANNABIS

CROSS-REFERENCE TO RELATED APPLICATIONS

This application is a National Stage Entry of International Patent Application No. PCT/US2015/000263, filed on Dec. 23, 2015, which claims priority to U.S. provisional application No. 62/095,827, filed on Dec. 23, 2014, and U.S. provisional application No. 62/249,583, filed on Nov. 2, 2015, each of which is hereby incorporated by reference in its entirety for all purposes.

FIELD OF THE INVENTION

The present disclosure relates to methods for the analysis and measurement of cannabis secondary compounds including cannabinoids and terpenes.

BACKGROUND OF THE INVENTION

The requirements for an acceptable cannabis assay have changed dramatically over the years, and the reasons for this appear to be related to its unique status. The political and social climate has contributed to the changing requirements, and legality issues surrounding cannabis have made it difficult to obtain a full spectrum of reference standards and sample material for validation studies. The number of states considering legalization of cannabis, medical or otherwise, is growing rapidly and a number of entrepreneurs have opened facilities to keep up with demand for reliable testing and labeling, however the "grey-market" status of cannabis and rush to open these labs have resulted in a wide array of creative methodologies for analytical testing that have not been validated. While there may be a number of methods suitable for cannabis analysis, as more states are now considering medical cannabis it is even more crucial for labs to perform important assay validation. This systematic evaluation of the scope and limitations of an assay is critical to demonstrate the assay is fit for its intended purpose and is an absolute requirement for the confident use of any methodology.

The present invention addresses many of the shortcomings of the present methods for cannabis analysis, while providing robust and accurate analysis alternatives.

SUMMARY OF THE INVENTION

In some embodiments, the present invention teaches methods for quantifying cannabinoids using ibuprofen, n-nonane, and 4-biphenyl carboxylic acid standards.

In some embodiments, the present invention teaches methods of extracting cannabinoids and terpenes using a bead beater.

In some embodiments, the present invention teaches methods of extracting cannabinoids and terpenes in an extraction solution with a solvent, wherein the solvent is ethanol.

In some embodiments, the present disclosure teaches a method for determining the concentration of at least one cannabinoid and/or at least one terpene in a sample of cannabis tissue, the method comprising: (a) homogenizing the sample of cannabis tissue in an amount of an extraction solution with a bead beater to obtain an analysis sample. (b) optionally diluting the analysis sample in a dilution solution; (c) subjecting the analysis sample to chromatographic separation and detecting the analysis sample with a detector; and (d) determining the concentration of at least one cannabinoid and/or at least one terpene in the sample of cannabis; wherein the extraction solution and the dilution solution each comprises a first internal standard with a known response ratio relative to the at least one cannabinoid in the detector, and a second internal standard with a known response ratio relative to the at least one terpene in the detector, and wherein the dilution solution further comprises a third standard with a known response ratio in the detector.

In any of the various embodiments disclosed herein for cannabinoid detection, the chromatographic separation can be high pressure liquid chromatography.

In some embodiments, the present disclosure teaches methods for determining the concentration of at least one cannabinoid and/or at least one terpene in a sample of cannabis tissue, wherein the moisture content of the cannabis sample is determined via FTIR.

Thus in some embodiments, the present invention teaches methods for determining the concentration of at least one cannabinoid and/or at least one terpene in a sample of cannabis tissue, wherein the dry weight of the cannabis sample is calculated by subtracting the FTIR moisture content from the cannabis sample.

In any of the various embodiments disclosed herein the chromatographic separation can be gas chromatography.

In some embodiments, the present disclosure is directed to methods of determining the concentration of cannabinoids or terpenes, wherein the detector is a flame ionization detector.

In some embodiments, the present disclosure is directed to methods of determining the concentration of one or more cannabinoids, wherein the one or more cannabinoids is selected from the group consisting of: THCA, CBDA, THC, CBD, CBG, CBC, and delta-8 THC.

In some embodiments, the present disclosure is directed to methods of determining the concentration of one or more cannabinoids, wherein the one or more cannabinoid is tetrahydrocannabinol.

In some embodiments, the present disclosure is directed to methods of determining the concentration of one or more terpenes, wherein the one or more terpenes is selected from the group consisting of: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In any of the various embodiments disclosed herein for cannabinoid and/or terpene detection, the extraction solution can be ethanol.

In any of the various embodiments disclosed herein for cannabinoid and/or terpene detection, the dilution solution can be ethanol.

In any of the various embodiments disclosed herein for cannabinoid and/or terpene detection, the first internal standard can be ibuprofen, the second internal standard can be n-nonane, and the third standard can be 4-biphenyl carboxylic acid In some embodiments the present invention teaches a high throughput method for extracting and quantifying cannabinoids and/or terpenes from cannabis tissue, said method comprising the steps of: a) homogenizing a cannabis sample with a bead beater using an extraction solution, said extraction solution comprising a solvent, a first internal standard, and a second internal standard, to produce an analytical extract; and b) performing an HPLC, and/or GC-FID analysis of the analytical extract of step a) to produce a signal for at least one cannabinoid and/or at least one terpene extracted from the cannabis sample, and to produce a signal for each of the standards; wherein the signal for the at least one cannabinoid is normalized based on the signal from the first internal standard to quantify said cannabinoid, and/or wherein the signal for the at least one terpene is normalized based on the signal from the second internal standard to quantify said terpene; wherein the first internal standard is ibuprofen at a known concentration, the second internal standard is n-nonane at a known concentration;

In some embodiments, the present invention teaches that the method of extracting and quantifying cannabinoids and/or terpenes from cannabis tissue, wherein the quantification of cannabinoids is performed via HPLC.

In some embodiments, the present invention teaches that the method of extracting and quantifying cannabinoids and/or terpenes from cannabis tissue, wherein the quantification of terpenes is performed via GC-FID.

In some embodiments, the present invention teaches that the method of extracting and quantifying cannabinoids and/or terpenes from cannabis tissue, wherein the analytical extract is diluted in a dilution solution prior to undergoing the HPLC and/or GC-FID analysis of step b); wherein the extraction solution comprises a third dilution standard comprising, and wherein the dilution solution is identical to the extraction solution except for the presence of the third dilution standard.

In some embodiments, the present invention teaches that the third dilution standard is BPCA.

In some embodiments, the present invention teaches that the method of extracting and quantifying cannabinoids and/or terpenes from cannabis tissue, wherein the signal for the at least one cannabinoid is normalized based on the signal from the first internal standard and the dilution standard to quantify said cannabinoid, and/or wherein the signal for the at least one terpene is normalized based on the signal from the second internal standard and the dilution standard to quantify said terpene.

In some embodiments, the present invention teaches that the method of extracting and quantifying cannabinoids and/or terpenes from cannabis tissue, wherein the solvent in the extraction solution is ethanol.

In some embodiments, the present invention teaches that the method of extracting and quantifying cannabinoids and/or terpenes from cannabis tissue, wherein step a) and step b) are completed within a 24 hour period.

In some embodiments, the present invention teaches that the method of extracting and quantifying cannabinoids and/or terpenes from cannabis tissue, wherein the cannabinoids that are quantified comprise THCA, CBDA, THC, CBD, CBG, CBC, delta-8 THC, and CBN.

In some embodiments, the present invention teaches that the method of extracting and quantifying cannabinoids and/or terpenes from cannabis tissue, wherein the terpenes that are quantified comprise terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In some embodiments, the present invention teaches an improved high throughput method for extracting and quantifying cannabinoids and/or terpenes from cannabis samples, said method comprising the steps of a) homogenizing cannabis with a bead beater using an extraction solvent with a first extraction standard, a second extraction standard, and a third extraction standard; b) diluting the extract of step a) with a dilution solvent comprising a first dilution standard and a second dilution standard; and c) comparing the signal obtained from the sample against the signal of the internal standards to quantify the cannabinoids and terpenes in the sample. In some embodiments the three extraction standards can all be the same, or all be different, or two can be the same while one is different than those two. In some embodiments the two dilution standards can be the same or different. In some embodiments one or more of the three extraction standards can be the same as one or more of the two dilution standards.

In some embodiments, adjustments in raw wt % signals obtained from the samples are compared against the signal of the internal standards in order to obtain a "true" final wt % concentrations for the cannabinoids and terpenes.

In some embodiments, the comparison between sample signals and internal standard signals are performed as described in Example 4 of the present invention.

In some embodiments, the first extraction standard is ibuprofen at a known concentration, the second extraction standard is n-nonane at a know n concentration, and the third extraction is 4-biphenyl carboxylic acid at a known concentration.

In some embodiments, the first dilution standard is ibuprofen at a known concentration, and the second dilution standard is n-nonane at a known concentration.

In some embodiments, the present invention teaches detection methods wherein the quantification of cannabinoids is performed via High Performance Liquid Chromatography (HPLC).

In some embodiments, the present invention teaches detection methods wherein the quantification of terpenes is performed via a Gas Chromatography Flame Ionization Detector (GC-FID).

In some embodiments the concentration of the first extraction standard is the same as the concentration of the first dilution standard.

In some embodiments, the extraction solvent is ethanol.

In some embodiments, the dilution solvent is ethanol.

In some embodiments, the extraction and dilution steps of the methods of the present invention are completed within a 24 hour period.

In some embodiments, the present invention teaches methods for quantifying cannabinoids.

In some embodiments, the cannabinoids that can be quantified comprise THCA, CBDA, THC, CBD, CBG, CBC, delta-8 THC, and CBN.

In some embodiments, the present invention teaches methods for quantifying terpenes.

In some embodiments, the terpenes that can be quantified comprise terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In some embodiments, the present invention teaches a method for determining the moisture content of a cannabis sample, said method comprising the steps of a) chemically desiccating the cannabis sample of known mass, and b) calculating the moisture content of the cannabis sample by the loss of mass after desiccation.

In some embodiments, the present invention teaches methods of chemically desiccating cannabis samples, said methods comprising placing the cannabis sample in a closed container with at least one chemical desiccant until the mass of the sample reaches a steady state.

In some embodiments, the present invention teaches that steady state is defined as the point at which the sample's mass fluctuates less than 5% per 24 hour period.

In some embodiments, the present invention teaches that the chemical desiccant is selected from the group consisting of: alkali metal halides, alkaline earth metal halides, iron halides, and aluminum halides; silica gel, calcium sulfate, calcium fluoride, activated charcoal, molecular sieves, calcium sulfate, calcium chloride, lithium chloride, cobalt chloride, deliquescent compounds, deliquescent salts, hygroscopic compounds, hydrophilic compounds, hygroscopic salts, humectants, absorbents, adsorbents, dehumidifiers, phosphorous oxide, sodium silicate, potassium silicate, potassium acetate, bentonite, montmorillonite clay, and monohydric compounds.

In some embodiments, the present invention teaches that the chemical desiccation methods of the present invention comprise allowing the cannabis samples to dry with the one or more chemical desiccant(s) for at least 72 hours.

In some embodiments, the present invention teaches a method for moisture correcting cannabinoid or terpene measurements of a cannabis sample, said method comprising the steps of a) providing a cannabis sample for analysis, b) measuring the moisture content of the cannabis sample via Fourier Transform Infrared spectroscopy (FTIR), and c) measuring the absolute cannabinoid or terpene content of the cannabis sample without additional drying steps; wherein the dry weight of the cannabis sample is calculated by subtracting the moisture content weight of the cannabis sample from the total weight of the cannabis sample used for measuring the cannabinoid or terpene contents.

In some embodiments, the present invention teaches alternative methods of determining the moisture content of a cannabis sample, including the use of dehumidifiers, auto-desiccators, extractor hoods, or vacuum-desiccators.

In some embodiments, the present invention provides methods which could be adopted as the federal or state standard among regulating agencies as a validated analytic method for cannabinoids and terpenes in cannabis. The methods of the present invention could be used for any federal or state governmental purpose, including but not limited to enforcement (e.g., Drug Enforcement Administration), compliance (e.g., U.S. Office of Drug and Alcohol Policy and Compliance) and/or therapeutic purposes (e.g., U.S. Food and Drug Administration).

DETAILED DESCRIPTION

Figure 1:
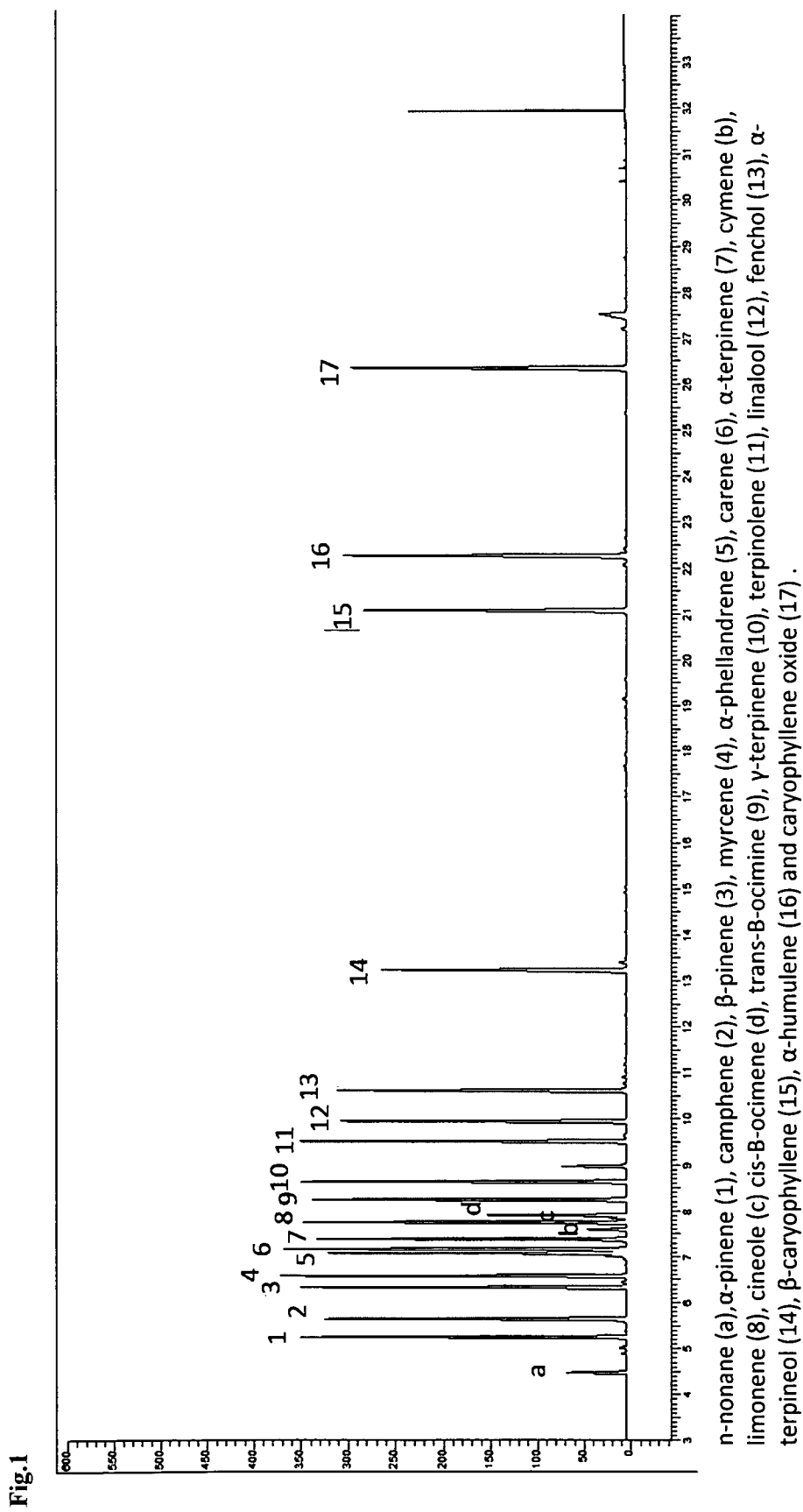
FIG. 1—GC-FID chromatogram of terpenes.

The scientific and technological discoveries surrounding cannabis have also contributed to the changing analytical landscape. Close to 500 chemical moieties have been identified in cannabis (1), and as research continues to shed light on the pharmacology of this array of secondary metabolites, assays have had to keep pace. Early assays focused on the pharmacologically active THC. Later endeavors focused on THC, CBD, and CBN, mainly as a manner to distinguish between drug-type and fiber-type cultivars. As the focus expanded to the plant itself (rather than just the content of the psychoactive THC in the finished flower) assays were needed to identity CBG and the naturally occurring acidic forms of all the cannabinoids, such as THCA, CBGA, and CBDA. As more studies added to the growing list of pharmacological effects of the cannabinoids, CBD(A) and THCV(A) being prime examples, the ability to assay for the "other" cannabinoids has become more important. Most recently attention has turned to the synergistic effects of the terpenes, thereby expanding the criteria for an acceptable assay to include the terpene family (2, 15, and PCT/US2014/030267).

Cannabis culture has also placed changing demands on analytical testing. Cultivators, connoisseurs, and patients have operated in an environment that has fostered an explosion of phenotypes and chemotypes. Indoor cultivation, hybridization practices, refined horticultural techniques, organoleptic preferences, therapeutic needs, and evolving cannabis products have created a situation that is far more complicated than a "single analyte and single matrix" condition that accompanies more phenotypically homogeneous crops. Laboratory oversight of cannabis production and maximized dialogue between cultivators and analysts is essential for proper sampling, statistical analysis, and quality control as cultivators become more educated and leverage technologies derived from traditional crop and plant science.

Due to these changing demands and the lack of a sufficiently validated method, we sought to develop a reliable and relatively high throughput assay that covered a broad range of analytes and concentrations. While there may be other methodologies appropriate for the analysis of cannabis, this work outlines practical procedures any lab should attempt before declaring an analytical assay suitable. The present invention outlines a practical analytical procedure that can be applied by both production model quality control and research oriented laboratories. The validation methods described herein should also be reviewed in detail by analytical labs providing services to the cannabis industry so they can ensure their methods are suited for the intended purpose.

Analyte Quantification

The present invention is based in part on the discovery of new methods for cannabis analyte quantification. In some embodiments, the present invention teaches the use of appropriate internal standards and validation techniques throughout the entire process. The present invention also teaches that the sample preparation procedure must allow for relatively high throughput and not be vulnerable to differences in sample morphology due to the large number of samples and diversity of phenotypes. We also sought to validate the method while keeping the practical aspects of this task in mind. A full validation for such a broad range of analytes and wide range of concentrations was extremely difficult. Therefore, we took an approach similar to Single Laboratory Validation. The assay performance must be acceptable and fully characterized.

While most cannabis testing labs lack rigorous evaluation of their analytical procedures, their experience with a myriad of real-world samples made it possible to understand the scope of an acceptable method. Similarly, a number of academic papers have been released over the years (3, 4, 5, 6, 7) that have presented validated assays for many cannabis analytes. However, very few have covered the desired repertoire of cannabis analytes. Furthermore, none of these methodologies were high throughput, and many never dealt with real-world samples or sample concentrations.

A recent emerging concept is that whole herbal cannabis has additional therapeutic benefits when compared to isolated THC. This has been attributed to the modulating and synergistic effects of the other cannabinoids and the terpenoids (2, 15, and PCT/US2014/030267). These two major classes of analytes are the most appealing at this time because of their combined pharmacological effects and organoleptic properties. The cannabinoids are biosynthesized in the plant as the acids, but most of the known pharmacology is a result of the neutral forms. Over 150 cannabinoids have been identified in the American Herbal Pharmacopoeia® (AHP), but THC(A), CBD(A), CBG(A), and THCV(A) are the most prevalent and the most biologically relevant at this time. There are over 200 terpenoids (1, 2, 7) in cannabis, but most are rarely seen in relevant quantities. After surveying the landscape with qualitative in-house assays across a broad range of cultivars, it was determined that the 17 terpenes analyzed in this work were the most commonly occurring, present in reasonable quantities, and had putative pharmacology (2, 4, FIG. 1 of the present disclosure).

Quantification of Cannabinoids

The two most common methods for analysis of cannabinoids are Gas Chromatography with Flame Ionization Detector (GC-FID) and High Performance Liquid Chromatography with a UV detector (HPLC-UV) (7). While GC-FID has a wide linear range, the present invention teaches that the GC injector coverts all the acidic cannabinoids to their neutral counterparts by decarboxylation, thus the original composition of the plant cannot be determined. Furthermore, the present application teaches that that decarboxylation is not quantitative and is dependent on variables such as injector temperature and configuration (8). In some embodiments, the present application teaches that analyte concentration in the GC vial can also affect the efficiency of conversion. It is because of the aforementioned variability that HPLC has been established as the method most suited for cannabinoid analysis. Hazekamp developed, validated, and shared an HPLC method, however it did not resolve CBG from CBD or CBN from CBGA (3). The most promising HPLC method was first presented by DeBacker et al, and subsequently applied by Swift et al, and published by AHP (5, 6, 7). Apart from the loss of resolution of CBG and CBD at high concentrations (higher than levels naturally occurring in the plant) this provided a good starting point. Both of these methodologies documented a linear range of approximately 1.5 orders of magnitude and while this would require two dilutions for the full range of cannabinoid concentrations (approximately 0.1% to 40%), it is realistic for an HPLC-DAD method and was adopted as our target range.

Quantification of Terpenoids

Although HPLC is the method of choice for cannabinoids, the present invention teaches that GC is the method of choice for small volatile organics such as the terpenoids. The present inventors realized that the large linear range of FID detection makes it possible to cover the extremely wide range of terpene concentrations (approximately 0.01% to 1.5%) with a single injection.

Quantification of Cannabinoids and Terpenoids with FTIR.

In some embodiments, the present invention teaches methods of analyzing cannabinoid and terpene profiles using Fourier Transform Infrared Spectroscopy (FTIR). FTIR is a spectroscopy technique used to obtain the infrared spectrum of absorption, emission, photoconductivity, or Raman scattering of a substance. Unlike atomic absorption, IR spectroscopy examines vibrational transitions within a single electronic state of a molecule, and is not concerned with specific elements, such as Pb, Cu, etc. Such vibrations fall into one of three main categories, i.e., stretching, which results from a change in inter-atomic distance along the bond axis; bending, which results from a change in the angle between two bonds; and torsional coupling, which relates to a change in angle and separation distance between two groups of atoms. Almost all materials absorb IR radiation, except homonuclear diatomic molecules. e.g., $O_2$, $H_2$, $N_2$, $Cl_2$, $F_2$, or noble gases.

IR range is sometimes further delineated by three regions having the wavelength and corresponding wavenumber ranges indicated:

"near-IR" 0.78-2.5 μm 12800-4000 $cm^{-1}$;
"mid-IR" 2.5-50 μm 4000-200 $cm^{-1}$; and
"far-IR" 50-1000 μm 200-10 $cm^{-1}$.

For a molecule to absorb IR, the vibrations or rotations within the molecule must cause a net change in the dipole moment of the molecule. The alternating electric field of the incident IR radiation interacts with fluctuations in the dipole moment of the molecule and, if the frequency of the radiation matches the vibrational frequency of the molecule, then radiation will be absorbed, causing a reduction in the IR band intensity due to the molecular vibration.

Examples of functional groups and their respective energy bands include, for example, hydroxl (O—H) (3610-3640 $cm^{-1}$), amines (N—H) (3300-3500 $cm^{-1}$), aromatic rings (C—H) (3000-3100 $cm^{-1}$), alkenes (C—H) (3020-3080 $cm^{-1}$), alkances (C—H) (2850-2960 $cm^{-1}$), nitrites (C≡N) (2210-2260 $cm^{-1}$), carbonyl (C=O) (1650-1750 $cm^{-1}$), or amines (C—N) (1180-1360 $cm^{-1}$). The IR absorption bands associated with each of these functional groups act as a type of "fingerprint" which is very useful in composition analysis.

By knowing which wavelengths are absorbed by each functional group of interest, an appropriate wavelength can be directed at the sample being analyzed, and then the amount of energy absorbed by the sample can be measured. The intensity of the absorption is related to the concentration of the component.

In some embodiments, the advantage of FTIR analysis is that it does not require samples to be pre-dried to remove moisture. In some embodiments, the advantage of FTIR analysis is that tissue samples can be assayed without first extracting analytes. Thus for example, in some embodiments, the present invention teaches the analysis of cannabinoids and/or terpenes, directly on plant tissue. In some embodiments, the present invention teaches the analysis of whole plant tissue such as leaves or inflorescences. In other embodiments, the present invention teaches the analysis of finely ground plant tissue as described infra.

In some embodiments, the present invention teaches methods of using FTIR to replace traditional moisture content analyses of cannabis samples. For example, in some embodiments, the present invention teaches methods of correcting cannabinoid and terpene content measurements by the moisture content values obtain from FTIR analysis.

In other embodiments, the present invention teaches the analysis of cannabinoids and/or terpenes, of cannabis tissue samples, and/or extracts such as kief, hashish, bubble hash, solvent reduced oils, sludges, e-juice, and tinctures, among others.

Analytical Standards

In some embodiments, the present invention teaches the use of an internal standard to improve the quality of results. The present invention teaches that an internal standard corrects for volume and/or analyte losses during sample processing, but only when added early in a process. The only methodology found that using an internal standard prior to sample processing was the AHP GC method (7). Among other characteristics, an acceptable internal standard must be easily available, stable, and have similar physicochemical properties to the analyte of interest. However, both AHP methods employ controlled substances (androstenedione and prazepam) and labs around California have been utilizing unstable (alpha-tocopherol) and chemically dissimilar (caffeine) standards. Clearly there was a need for more appropriately suited internal standards. The present invention presents a unique approach of employing three internal standards. Two of them are present in both the extraction solution and diluent solution and corrects for variation in terpene and cannabinoid content due to sample processing and extraction. These concentrations are unaffected by dilution and are used to generate the internal standard calibration curves. The third is only present in the extraction solution, and corrects for variability in cannabinoid content due to the dilution process (vide infra).

Extraction and Sample Preparation Methods

Solvent

The first step in any HPLC or GC—based chemical analysis is the extraction of cannabinoids and terpenes. A variety of methods for extracting samples are provided in the literature, and they vary in solvent type, solvent volume, sample mass, and extraction procedures. Both of the AHP methods recommended the use of methanol/chloroform as the solvent, however this generates a halogenated waste stream and methanol is one of the more difficult solvents to use with standard pipetting techniques.

In some embodiments, the present invention teaches the use of Ethanol as the extraction solvent. In some embodiments, ethanol, on the other hand, is easier to handle and a number of researchers have shown it is a suitable solvent for extracting cannabinoids and terpenes so is the solvent of choice for some embodiments of the present invention.

Sampling

Cannabis is an agricultural crop and this means inherent variability in analyte concentrations. Thus, proper sampling is critical. Only one method specified a bulk sample mass required to obtain representative results (3). While the recommended mass of 60 grams would undoubtedly reduce variability in testing different lots of material, this is too high a material demand for a host of reasons including associated cost. As a result, in lieu of being able to randomly sample the actual cultivation site, the present invention teaches in some embodiments a reduction the sample requirement to 5-7 grams.

Homogenizing

The approach of Hazekamp (3) was used to pre-homogenize the bulk samples and the finished flowers were ground to fine pieces in a stainless steel coffee grinder.

Moisture Correction and Chemical Desiccation

Traditionally, cannabinoid and terpene contents are presented in terms of % based on the dry weight of the sample. For example, a 1 gram dried sample of cannabis containing 10% THC and 1% terpenes would contain 100 milligrams of THC and 10 milligrams of terpene oil. In order to reduce the analysis error introduced by the variability in moisture content between cannabis samples, the AHP methods for cannabis analysis recommend drying said samples in a forced air oven prior to HPLC and GC analysis (7). This is the method currently employed by most cannabis analytical laboratories.

The present invention is based in part on the discovery that traditional cannabis analysis methods of oven drying samples are inaccurate because they often lead to the loss of terpenes, particularly that of headspace volatiles. Thus in some embodiments, the present invention teaches against the use of forced air oven drying.

Typical drying procedures, such as those recommended in the AHP monograph, involve an initial drying at for 3 days at 15-21 C until inflorescences lose 75% of their initial mass, followed by 1-2 weeks at 15-21 C in plastic bags following a "burping" procedure. When completely dried using this procedure, inflorescences are reported to contain approximately 10% moisture (AHP monograph). Determination of moisture content is typically done by heating 1.0 g of powdered cannabis in an oven at 105 C for 2 hours (7-AHP monograph).

The recommended procedure for drying and curing is too long for timely determination of secondary metabolite production during "time courses", and the procedure for determining moisture content raises concerns due to the elevated temperature, which can drive off not only moisture but also volatile secondary metabolites produced by cannabis. This is especially true of cannabis, which contains not only green leaf volatiles but also high amounts of monoterpenes. The terpenes can reach levels of 2% by mass, and although boiling points are generally above 150 C, they do have vapor pressures and analyte loss can be observed at room temp. This process can be accelerated at elevated temperatures.

Cannabis also produces the cannabinoids as their acidic forms, and these forms undergo decarboxylation to provide the biologically active neutral forms. This process is much faster at elevated temperatures but also occurs spontaneously at room temp, and cannabis stored for long periods will show larger amounts of THC and CBD relative to THCA and CBDA. The loss of $CO_2$ during this process can amount to significant loss of mass when the cannabinoids constitute as much as 20% by mass of inflorescences. For instance, the present disclosure teaches that 1.0 g of cannabis containing 20% of THCA can lose approximately 2.5% of its mass as $CO_2$ upon heating due to decarboxylation to form THC.

In some embodiments, the present invention teaches alternative methods of chemical drying of cannabis samples. Thus in some embodiments, the present invention teaches methods of drying samples for cannabis analyte measurements with one or more chemical desiccants. A non-exhaustive list of the chemical desiccants suitable for the methods of the present invention include: Drierite® (calcium sulfate); DampRid® (calcium chloride crystals); a salt selected from the group consisting of alkali metal halides, alkaline earth metal halides, iron halides, and aluminum halides; silica gel, calcium sulfate, calcium fluoride, activated charcoal, molecular sieves, lithium chloride, cobalt chloride, among others. Other humidity-attracting substances useful for the methods of the present invention include: deliquescent compounds, deliquescent salts, hygroscopic compounds, hydrophilic compounds, hygroscopic salts, humectants, absorbents, adsorbents, dehumidifiers, phosphorous oxide, sodium silicate, potassium silicate, potassium acetate, bentonite, montmorillonite clay, molecular sieve, monohydric compounds, polyhydric compounds, and polysaccharides such as start and cellulose.

Thus in some embodiments, the present invention teaches methods of drying cannabis samples prior to chemical analysis by placing in a sealed container with one or more chemical desiccants. In some embodiments, the present invention teaches grinding the same prior to drying. In other embodiments, whole cannabis tissues can be desiccated.

In some embodiments, the desiccation time of cannabis samples will depend on multiple factors including the air temperature and humidity, and moisture level of the sample. In some embodiments, the present invention teaches conducting chemical desiccation at room temperature. In other embodiments, the present invention teaches methods of conducting chemical desiccation at temperatures below 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0 degrees Celsius. In some embodiments, the present invention teaches conducting chemical desiccation at temperatures between 10 and 40 degrees Celsius.

In some embodiments, the present invention teaches desiccation of samples until the samples reach substantially steady state mass levels. In some embodiments steady state mass means a mass loss of less than 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% per day.

In some embodiments, the present invention teaches chemical desiccation of cannabis samples for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours. In some embodiments, certain cannabis samples may require up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 or more days.

In some embodiments, the present invention teaches using at least 1×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, 40×, 41×, 42×, 43×, 44×, 45×, 46×, 47×, 48×, 49×, 50×, 51×, 52×, 53×, 54×, 55×, 56×, 57×, 58×, 59×, 60×, 61×, 62×, 63×, 64×, 65×, 66×, 67×, 68×, 69×, 70×, 71×, 72×, 73×, 74×, 75×, 76×, 77×, 78×, 79×, 80×, 81×, 82×, 83×, 84×, 85×, 86×, 87×, 88×, 89×, 90×, 91×, 92×, 93×, 94×, 95×, 96×, 97×, 98×, 99×, or 100× the amount of desiccant chemical than cannabis samples.

In some embodiments, the methods of the present invention desiccate cannabis samples for HPLC or GC analysis at least 16, 15, 14, 13, 12, 11, 10, 9, 8, 7, 6, 5, 4, 3, 2, or 1 day faster than traditional oven drying techniques.

Persons having skill in the art will, after reviewing the present specification, recognize other methods of determining cannabis sample moisture content. In some embodiments the present invention teaches the use of tools capable of reducing relative humidity without heating samples. For example, in some embodiments, the present invention teaches using commercially-available dehumidifiers, auto-desiccators, extractor hoods, or vacuum-desiccators.

Extraction Efficiency

The literature presents a wide range of sample masses for extraction, ranging from 100-200 mg to 500-1000 mg (3, 4, 7). The larger mass is expected to give more representative results so a number of sample masses were evaluated. The literature also presents a wide range of volume/mass ratios for extraction of analytes ranging from 3 mL to 10 mL per 100 mg of sample (4, 7). In some embodiments, the present invention teaches methods of minimizing cost and waste, while also maximizing concentrations of terpenes by using optimal levels of solvent for cannabis analyte extraction. Thus in some embodiments, the present invention teaches the use of 1 mL, 1.1 mL, 1.2 mL, 1.3 mL, 1.4 mL, 1.5 mL, 1.6 mL, 1.7 mL, 1.8 mL, 1.9 mL, 2 mL, 2.1 mL, 2.2 mL, 2.3 mL, 2.4 mL, 2.5 mL, 2.6 mL, 2.7 mL, 2.8 mL, 2.9 mL, 3 mL, 3.1 mL, 3.2 mL, 3.3 mL, 3.4 mL, 3.5 mL, 3.6 mL, 3.7 mL, 3.8 mL, 3.9 mL, 4 mL, 4.1 mL, 4.2 mL, 4.3 mL, 4.4 mL, 4.5 mL, 4.6 mL, 4.7 mL, 4.8 mL, 4.9 mL, 5 mL, 5.1 mL, 5.2 mL, 5.3 mL, 5.4 mL, 5.5 mL, 5.6 mL, 5.7 mL, 5.8 mL, 5.9 mL, 6 mL, 6.1 mL, 6.2 mL, 6.3 mL, 6.4 mL, 6.5 mL, 6.6 mL, 6.7 mL, 6.8 mL, 6.9 mL, 7 mL, 7.1 mL, 7.2 mL, 7.3 mL, 7.4 mL, 7.5 mL, 7.6 mL, 7.7 mL, 7.8 mL, 7.9 mL, 8 mL, 8.1 mL, 8.2 mL, 8.3 mL, 8.4 mL, 8.5 mL, 8.6 mL, 8.7 mL, 8.8 mL, 8.9 mL, 9 mL, 9.1 mL, 9.2 mL, 9.3 mL, 9.4 mL, 9.5 mL, 9.6 mL, 9.7 mL, 9.8 mL, 9.9 mL, or 10 mL, of solvent for every 100 mg of cannabis tissue.

Extraction of Analytes

In some embodiments, most of the analytes of interest reside in the easily disrupted trichomes of the cannabis plant. Procedures for extracting these analytes include passive extraction for 30 minutes (4), sonication for 30 minutes (5), and maceration for one hour followed by sonication for 30 minutes (7). Sonication has been one of the more popular methods for disruption and is very effective for small particles and trichomes. However, this process can be less efficient with solid samples or large particle sizes, such as bulk plant material (13). Sonication baths can improve throughput, however there is variability in power across the bath that depends on sample depth, placement, and number of samples in the bath (12, 13). Using a probe for disruption minimizes variability, but also decreased throughput while increasing the possibility for cross-contamination by the probe.

In some embodiments, the present invention teaches the use of high throughput homogenizers. In some embodiments, the present invention teaches the use of a wide range of grinding, extraction, and milling extraction methods (13). In some embodiments, the present invention teaches the use of a beadbeater homogenizer. In some embodiments the present invention teaches extraction without use of a sonicator. The Examples of the present specification evaluate the use of various homogenizing technologies for extracting cannabis samples, and compares them against the methods taught herein.

Method Validation

Method validation includes all of the procedures that demonstrate a particular method used for the quantitative analysis of analytes in a given matrix is reliable and reproducible. Fishedick et al, performed a very limited validation of their terpene assay by spiking in pinene, linalool, and caryophyllene at a single concentration and verifying acceptable recovery (4), however this did not include all the terpenes of interest nor did it cover the expected range of concentrations. Both Hazekamp and DeBacker et al. had reasonable approaches for validating the HPLC assays for cannabinoids, however they were incomplete (3, 5). Hazekamp used finished cannabis flowers and the method of standard addition to determine recoveries of THCA. THC, CBD, and CBN, however CBDA, CBGA, CBG, THCA, and THCV were not evaluated. Furthermore, since standard addition was employed, analytes were only validated at and above the highest expected concentrations thus the lower quantitation levels remained uncharacterized. For instance THCA was only validated at concentrations of 19%, 22%, and 26% and CBD at concentrations of 6%, 7%, and 8%. DeBacker et al, was able to validate all of the major analytes of interest by spiking cannabis extract into nettle, however this covered narrow concentration ranges of 1.8%-6.1% for THCA, 1.0%-3.3% for CBDA, and 0.1%-0.4% for CBGA. None of these levels reflect those found in most samples in today's marketplace. The present invention teaches methods to validate all the major analytes of interest in ranges that were applicable to real world cannabis samples.

Evaluation of Calibration Curves

A relatively common practice by labs that are evaluating calibration curves is to simply let the instrument's software run a regression analysis without evaluating the data plot or the residuals. Typically, it is then assumed that a correlation coefficient greater than 0.99 indicates the curve is linear and any deviation is simply due to dilution errors. While this may be true for detectors such as FID, it is a dangerous assumption when utilizing UV or MS detection. Furthermore, calibration solutions can give linear responses over two orders of magnitude with FID while the same solutions are linear to just over one order of magnitude with MS or UV detection.

Correlation is not a measure of linearity, and it is easy to generate data with apparently good correlation, but examination of the residuals may indicate the calibration is unfit for the intended calibration or desired concentration range. Simply relying on a correlation coefficient can be misleading and a linear regression over two orders of magnitude can provide a coefficient of 0.999 but still give >35% error at the low end when back calculating results, and this is not necessarily due to dilution error. While most determinations may be made at higher concentrations, the analyst needs to understand the implications of diluting to the lower and less accurate end of the curve. Spike recoveries at high, medium, and low concentrations that bracket the calibration curve would show this error, but many laboratories do not perform this step. Back calculating concentrations of standards from the calibration curve as a way of evaluating the residuals can serve as a leading indicator of the performance of spike recovery studies, and residuals with unacceptably high values or values indicating unacceptable trends suggest the calibration should be repeated and/or the linear range of the assay adjusted.

The present invention teaches methods which not only require a correlation coefficient greater than 0.99, but to also examine the residuals by back calculating the concentrations of each standard from the calibration curve to determine the error in order to evaluate the quality of the linear regression.

Sample Types

While the experimental results presented herein were carried out with flower samples, the present invention can also been applied to water hash, dry sift, kief, and a variety of extracts and shatters. This methodology is suitable as long as the extract does not form a biphasic mixture. Various oils, tinctures, butters, and baked goods have been found to present a biphasic mixture with the extraction solvent and the method cannot be applied to these matrices.

For non-homogeneous agricultural samples, such as flowers, a larger sample size improves reproducibility of measurements from lot to lot. In lieu of being able to sample the actual site, a 5-7 g "random" sample was ground in a stainless steel coffee grinder and a portion of this ground material was extracted.

Plant Variability

The apparent ease of obtaining and publishing analytical testing results has contributed to confusion when it comes to their interpretation. This confusion can arise from two sources, 1) a misunderstanding of the variability characteristic in an agricultural crop, and 2) loss of data integrity during the cultivation, testing, and reporting process.

Agricultural crops inherently have a large amount of natural variation resulting from differences in environmental conditions, genetic background, developmental stage, farming practices, and seasonal changes (17), which result in differences in organoleptic profile, appearance, nutrient composition, shelf life, and crop yield. This variation is important when considering nutritional value or other quality attributes of human food, however it becomes critical when the agricultural crop contains secondary metabolites that are used to treat medical conditions.

The synergistic effects of the cannabinoids and terpenes in cannabis provide its medicinal properties, thus determining the concentrations of both is paramount. In fact, both the chemical fingerprint as well as the potency of these compounds is of primary concern to human consumption (2, 15). The analytical method described herein has been employed not only to determine the chemotype of cannabis preparations destined for human consumption but also to gain a better understanding of the sources of variability associated with the production of cannabis in a state-of-the-art indoor production facility. In some embodiments, additional applications of the methods of the present invention include monitoring chemotype through developmental stages, evaluation of the impact of different environmental conditions and cultivation techniques, and selection of progeny for breeding purposes.

SUMMARY

The present invention teaches optimized and validated methods for the analysis of terpenes and cannabinoids in cannabis that is amenable to relatively high throughput and provides accurate and reliable results. A single sample extraction procedure provides extract that can be analyzed for both terpenes and cannabinoids by GC-FID and HPLC-DAD, respectively.

Both the precision and accuracy of the method were found to be acceptable for all of the terpenes and cannabinoids analyzed and this was demonstrated by spike recoveries at analyte levels that reflect those found in most samples on the market today.

Both intra-day and inter-day precisions of the complete extraction and analysis were demonstrated on five different cultivars containing different cannabinoid and terpene profiles and exhibiting different flower morphologies, and in most cases the RSDs were lower than the PRSDs. While inter-day precision was not satisfactory for the volatile monoterpenes, this proved to be an artifact of the experimental design and highlighted the need for timely analysis of samples once trichomes are ruptured.

It has also been demonstrated that a high throughput homogenizer makes this method amenable to processing a large number of samples with good extraction efficiency and precision, unlike traditional sonication or passive extraction methods. This method is only minimally affected by sample morphology and has been found to be fairly robust from a process standpoint. The instrumental methods also perform reliably with this sample load.

Large sample sizes along with well-characterized analytical assays are the key to obtaining consistent and representative assay results.

Comparisons with other labs suggest many testing facilities do not perform even basic steps to verify the performance of the assays being used. In some cases, such as with missing terpenes or misidentified minor cannabinoids, this results in misleading information. In other cases, such as labeling a Chemotype I cultivar with a Chemotype II test result, this has the potential to cause serious misadventures for the medical or recreational consumer. It is also important to note that these results were not isolated incidents, and consistently poor performance was noted over almost two years.

These results highlight the critical need for complete laboratory integration into any proposed cannabis production facility. Under the current paradigm, analytical laboratories must take the samples provided for testing at face value and assume they are representative of the entire crop. Meanwhile, cultivators and patients must take analytical results at face value and assume they have been obtained with reliable methodologies. As demonstrated above, both of these assumptions can have an additive effect in the propagation of misinformation. A facility staffed with interacting cultivators, plant and crop scientists, and research scientists allows for proper interpretation of data and incorporation of reliable feedback loops required for an efficient production process. This integrated chain of custody leading from plant, to data, to information is also essential for building accurate knowledge cultivators, patients, and legislators can use.

Example 1—Internal Standards, Extraction Solution, and Diluent

Denatured ethanol, nonane, 4-biphenyl carboxylic acid, and ibuprofen were obtained from Sigma Aldrich. The Certificates of Analyses for each lot were used determine the purity, and mass values were adjusted accordingly. Diluent was reagent grade ethanol. To prepare typical extraction solution, nonane, ibuprofen (IBU), and 4-biphenyl carboxylic acid (BPCA) were added to a volumetric flask, which was brought up to volume with reagent grade ethanol and stirred for 3 hours to give a solution that contained 0.1 mg/mL nonane, 0.2 mlg/mL IBU, and 2 mg/mL BPCA. The peak area of BPCA in new batches of extraction solution is verified to be within 2% of previous batches by diluting 1:6 and injecting on the HPLC in triplicate.

The dilution solution was prepared in a similar manner but BPCA was left out of the solution.

To prepare spike solution with both nonane and ibuprofen (IBU) as internal standards, each was added to a volumetric flask and it was brought up to volume with reagent grade ethanol to give a solution that contained 1.5 mg/mL nonane and 288 mg/mL IBU.

Example 2—GC-FID Analysis of the Terpenes

The terpenes were separated on a Perkin Elmer Clarus 680 GC fitted with an FID detector, an Elite 5MS column, and a Restek Precision SkyLiner. The injector temperature was set at 230° C., a 1.5 µL injection volume was used, and the split flow was set at 20:1. The carrier gas was hydrogen and was set at a flow rate of 1.3 mL/min and the oven program was a 3.5 minute hold at 60° C. a ramp to 155° C. at 3.5° C./min. and a ramp to 300° C. at 30° C./min.

Terpene standards were obtained from Sigma Aldrich and the Certificates of Analyses were used to correct mass values. Calibration curves were prepared gravimetrically in diluent solution at concentrations of 1.000, 0.815, 0.655, 0.495, 0.335, 0.175, and 0.015 mg/mL and an internal standard concentration (nonane) of 0.1 mg/mL. The instrument was calibrated according to the manufacturers procedures. The calibration curves were obtained in triplicate on separate days. In addition to requiring correlation coefficients greater than 0.99, the residuals w ere evaluated to verify the quality of the fit. As is typical with standard curve fitting procedures the residuals should show a random distribution with a mean close to zero (2, 32). For laboratories that do not have statistical software, the residuals can be evaluated by calculating the difference of the experimental points from the fitted line and plotting these differences as a function of concentration.

The GC method provided sufficient resolution of all of the terpenes of interest (FIG. 1). Two terpenes, p-cymene and cineole, were identified by both mass spec and authentic standards and resolution was verified, however these terpenes were not found in any significant amounts in the samples analyzed. As a result, these compounds were not added to the methodology. Carene and alpha-phellandrene lost baseline resolution at the highest concentration level, however the software was able to identify and integrate each peak adequately. These are generally only minor components in real samples and are not seen at concentrations high enough to be problematic.

Figure 2:
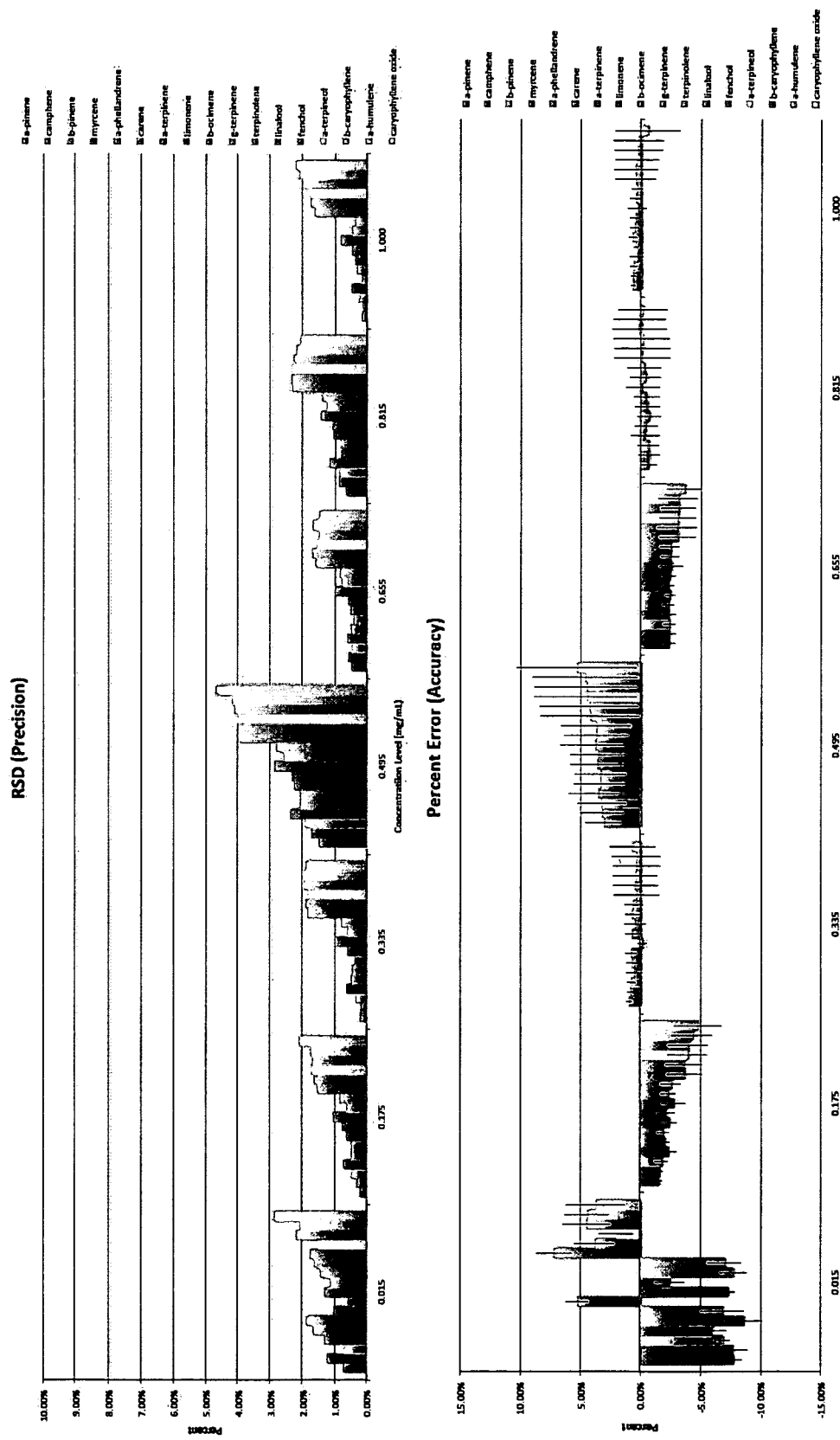
FIG. 2—RSDs and residuals (with ST DEV for error bars) for terpene calibration curves obtained in triplicate.

Each calibration curve (1.000, 0.815, 0.655, 0.495, 0.335, 0.175, and 0.015 mg/mL) was obtained in triplicate and the charts show the precision and accuracy (residuals) for each calibration level (FIG. 2). For a linear range over two orders of magnitude, such as this, it is critical to use equidistant calibration levels to minimize the degree of leverage a point may have.

The curves for each of the terpenes show good precision and accuracy over the entire range. The RSDs were generally less than 2%. The accuracies of the standards were generally within 2% of predicted values at the high end of the curve and within 8% of predicted values at the low end of the curve. The residuals also exhibit a random distribution with no clear undesirable trends present. Clearly, n-nonane is a more suitable internal standard for the monoterpenes than for the sesquiterpenes, but it performs adequately for both. The table shows the $R^2$ values for each of the terpenes are greater than 0.99 (Table I).

Optimization of the oven program and carrier gas flow rate was carried out with solutions of terpene standards. Extensive method development found that a 1.5 µL injection volume and a 20:1 split flow provided the most linear and reproducible calibration curves for all of the analytes. Larger injection volumes resulted in poorer peak shape and loss of resolution. Larger injection volumes also resulted in higher RSDs, presumably from injector back flash due to the use of ethanol as the extraction solvent. Lower split flows resulted in poorer peak shape and loss of resolution while larger split flows resulted in injector discrimination, which reduced the efficacy of the internal standard. It should be noted that we utilized several GCs and they each required slight modification of the split flow and temperatures to achieve similar results.

TABLE 1

Correlation coefficients for the terpene calibration curves

| Terpenoid | $R^2$ |
|---|---|
| alpha-pinene | 0.99926 |
| camphene | 0.99923 |

TABLE 1-continued

Correlation coefficients for the terpene calibration curves

| Terpenoid | $R^2$ |
|---|---|
| beta-pinene | 0.99923 |
| myrcene | 0.99922 |
| alpha-phellandrene | 0.99927 |
| carene | 0.99918 |
| alpha-terpinene | 0.99919 |
| limonene | 0.99920 |
| beta-ocimene | 0.99913 |
| g-terpinene | 0.99916 |
| terpinolene | 0.99915 |
| linalool | 0.99882 |
| fenchol | 0.99880 |
| alpha-terpineol | 0.99872 |
| beta-caryophyllene | 0.99870 |
| alphahumulene | 0.99868 |
| caryophyllene oxide | 0.99821 |

Example 3—HPLC-DAD Analysis of the Cannabinoids

The assay was run on an Agilent 1290 HPLC system equipped with a G4212A diode array detector, a G 1316C temperature controlled column compartment, a G4226A autosampler, and a G4204A quaternary pump. Separation of the cannabinoids was achieved on a Poroshell 120 EC-C18 column (2.7 m, 150 mm×2.1 mm i.d., PN 693775-902) with a Poroshell 120 EC-C18 guard column (2.7 µm, 5 mm×2.1 mm i.d., PN 821725-911) in place (Agilent Technologies, Santa Clara, Calif.). Instrument control, data acquisition and integration was achieved with OpenLab CDS ChemStation Rev C.01.06[61] software (Agilent Technologies). The HPLC method uses a 1.5 µL injection volume for all calibration standards, check standards, and sample analyses. Full spectra were recorded from 200-400 nm, and 214 nm was used for quantification of all analytes.

Mobile phases consisted of 0.1% formic acid (Sigma Aldrich PN 56302-50ML-GL) in HPLC grade water (Sigma Aldrich Chromasolv® PN 270733-4L) on the A side and 0.1% formic acid in HPLC grade acetonitrile (Sigma Aldrich Chromasolv® PN 34851-4L) on the B side. The flow rate was 0.5 mL/min and the assay begins with an 8 minute isocratic hold at 66% B, followed by a linear gradient to 95% B over four minutes, 95% B is maintained for one minute, then returns to re-equilibrate the column at 66% B for four minutes before the next injection. The total run time for the method is 17 minutes.

Cannabinoid standards for THCA, CBDA, THC. CBD, CBG, CBC, delta-8 THC, and CBN were obtained from Restek as 1.0 mg/mL solutions in methanol. Calibration solutions for the acidic and neutral forms were prepared separately. Due to legal issues dictating how these standards are supplied it is the most practical manner to combine multiple cannabinoid standards into a single solution with an internal standard. To prepare the calibration solutions 1000 µL of each was placed in a small amber vial and the solvent was evaporated under a gentle flow of argon, after which the vial placed under gentle vacuum until the theoretical weight (1 mg±0.1 mg) was obtained. The residues were dissolved in a total of 4000 uL of diluent to give a stock cannabinoid solution of 0.250 mg/mL with 0.2 mg/mL ibuprofen as the internal standard. The stock solutions of the neutral and acidic moieties were then diluted to concentrations of 0.250, 0.125, 0.063, 0.031, and 0.016 mg/mL.

Each set of calibration curves was obtained in triplicate on separate days, and the calibrations for the acids and neutrals were merged into a single instrumental method within the ChemStation software. The single raw data set was processed to obtain both internal standard calibration curves (ISTD) that referenced IBU as the internal standard and external standard calibration curves (ESTD). In addition to requiring correlation coefficients greater than 0.99, the residuals were evaluated to verify the quality of the fit. As is typical with standard curve fitting procedures the residuals should show a random distribution with a mean close to zero (2, 32).

For laboratories that do not have statistical software, the residuals can be evaluated by calculating the difference of the experimental points from the fitted line and plotting these differences as a function of concentration. This is a critical process for the cannabinoid calibration curves since the "true" values of the validation samples are determined empirically from the curves and this helps ensure they are not biased by non-linearity of the calibration curves.

Since standards for CBGA, THCVA, and CBDVA were not commercially available, both heated and unheated extracts from cultivars known to contain these analytes were analyzed by GCMS and GC-FID to identify the peaks corresponding to the neutral analytes and the approximate ratios. Both unheated and heated extracts were then analyzed by HPLC to identify the retention times of CBGA, THCVA, CBDVA, THCV, and CBDV. Based on similarities of spectral properties and molar absorption coefficients, these analytes were then quantified by referencing known calibration curves. CBGA and CBDVA referenced CBDA, THCVA referenced THCA. CBDV referenced CBD, and THCV referenced THC. Standards for THCV. CBDV, and CBGA eventually became available from Cerilliant and they were used to verify the retention times and calibrate the instruments.

Figure 3:
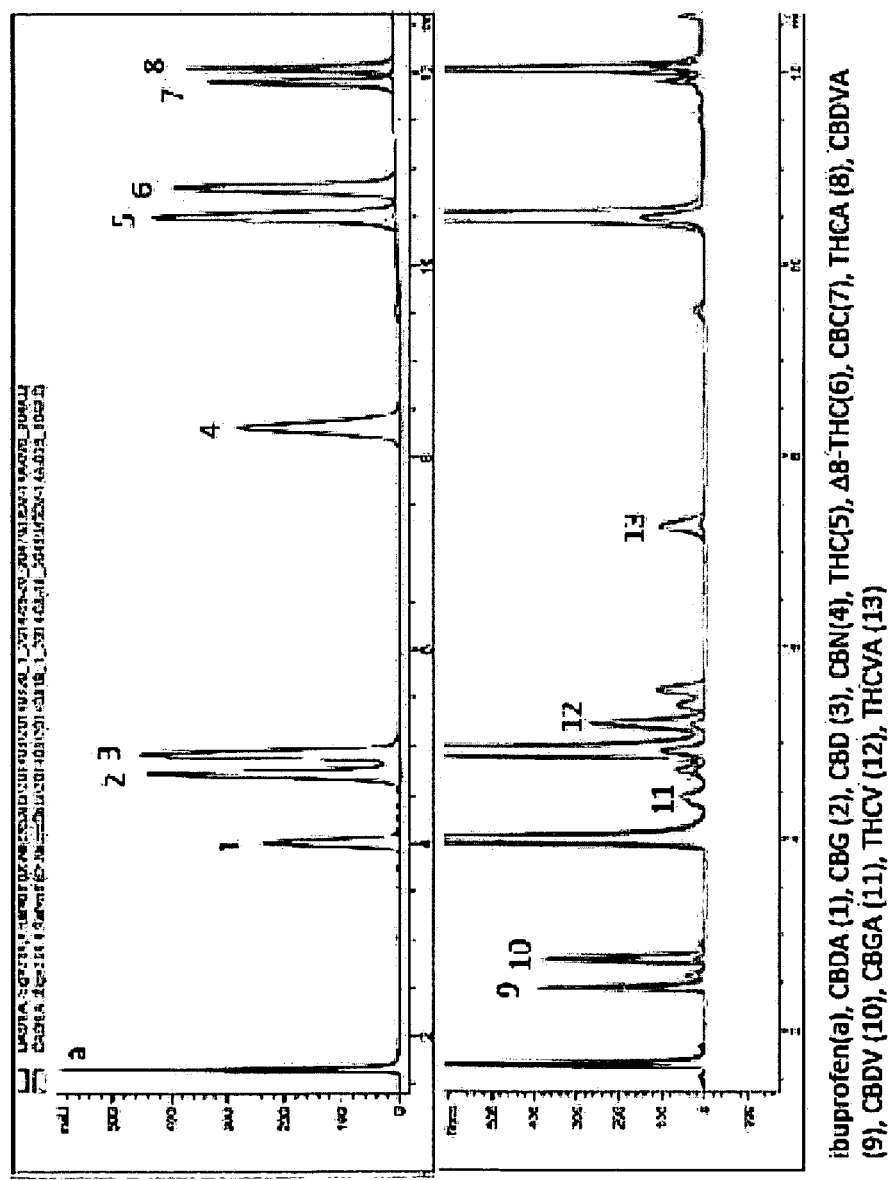
FIG. 3—HPLC-DAD chromatograms of cannabinoid standards (top) and extracts (bottom).

The HPLC method provided sufficient resolution of the major cannabinoids of interest in 17 minutes (FIG. 3). The tipper chromatogram is an overlay of the neutral cannabinoid standards (blue) and the acidic cannabinoid standards (red). Baseline resolution of CBG/CBD and THCA/CBC is lost at the highest calibration level, but the software does an excellent job of identifying and integrating the peaks, as illustrated by the good linearity and RSDs at all concentration levels. The lower chromatogram is an overlay of unheated (blue) and heated (red) extract containing CBDVA, CBGA, and THCVA. This was done to identify the retention times of these analytes and their neutral counterparts. The sample is clearly overloaded with respect to the major THC(A) and CBD(A) analytes, which results in loss of baseline resolution, however this is generally not an issue at the working concentrations of the assay. Quantifying trace amounts (<0.15%) of analytes in very concentrated extracts (dilutions <6x) should be approached with caution on a case by case basis since the presence of a closely eluting major analyte can result in column overload and loss of resolution. CBCA is conspicuously missing form our analyses due to the lack of a readily available standard. Based on other analyses (3) CBCA likely elutes after THCA near the end of the run so a slight extension of the run may be required.

Figure 4:
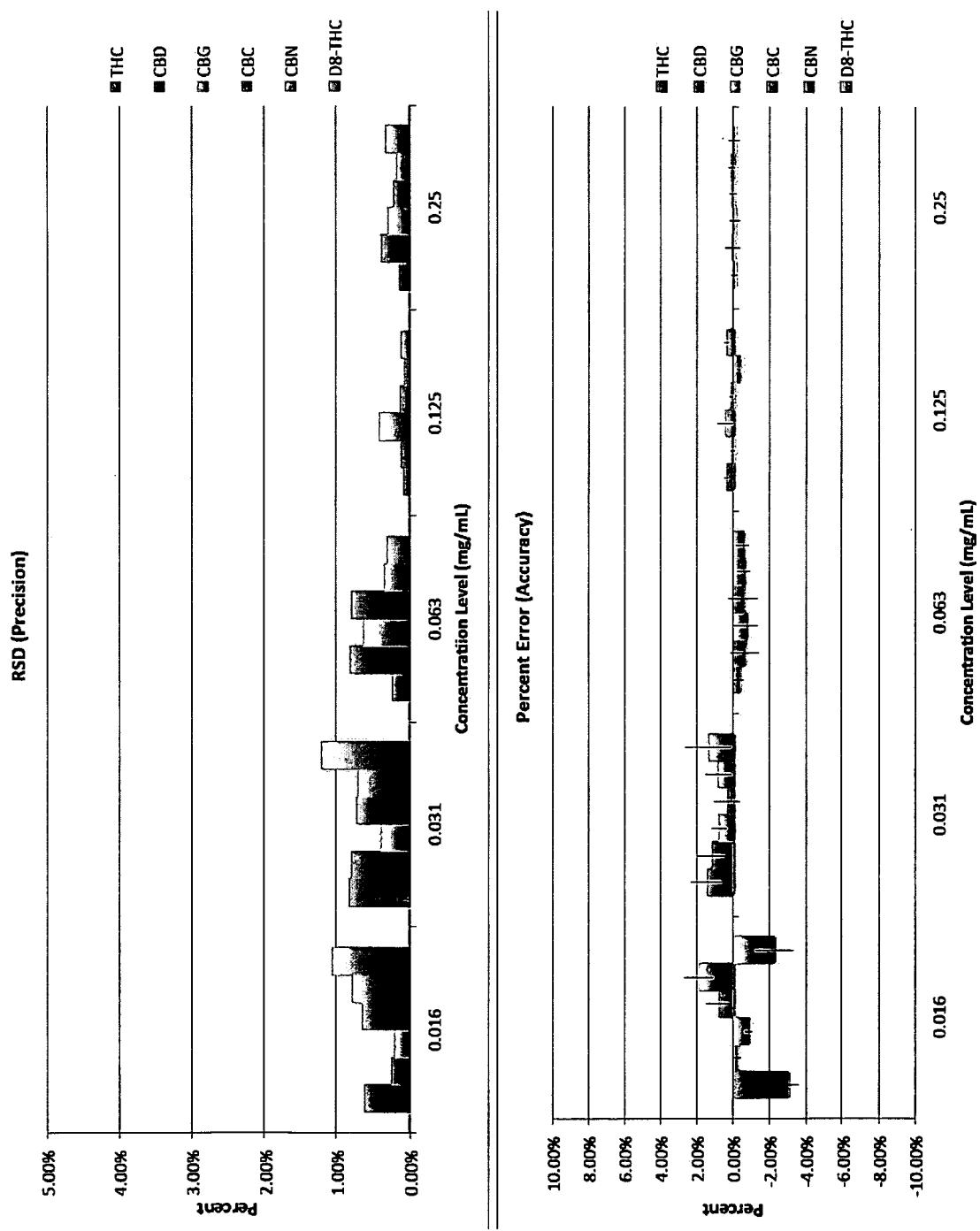
FIG. 4—RSDs and residuals (with ST DEV for error bars) for neutral cannabinoid calibration curves obtained in triplicate.
Figure 5:
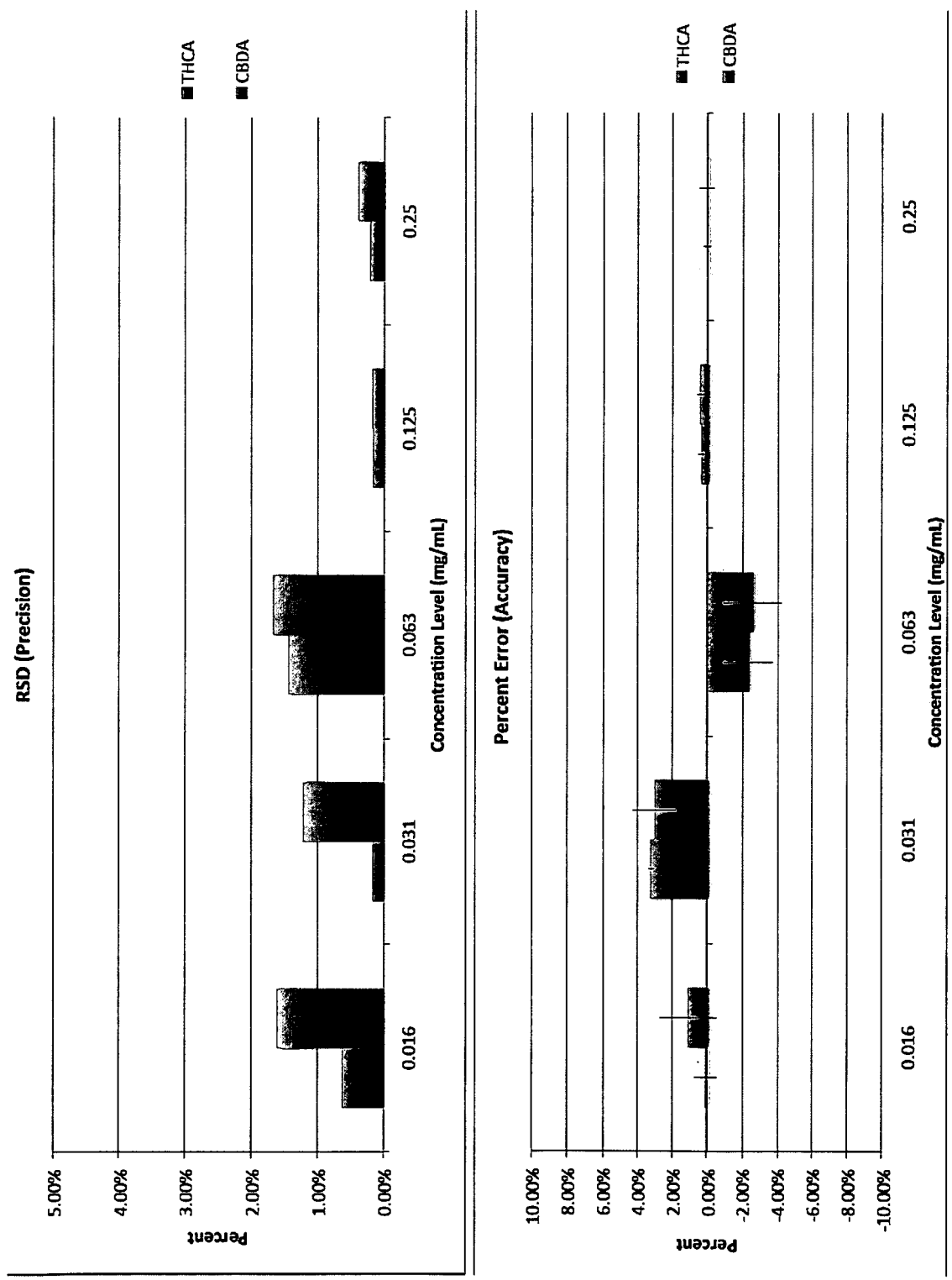
FIG. 5—RSDs and residuals (with ST DEV for error bars) for acidic cannabinoid calibration curves obtained in triplicate.

The charts in FIGS. 4 and 5 show the precision and the accuracy (residuals), determined by back-calculating the concentrations from the calibration curves. RSDs are typically around 1%, and error is less than 1% at the higher concentrations and less than 2% at the lower concentrations. The decision to use calibration levels based on equal percentages rather than equal distances (as in the terpene assay)

was a practical one based on the cost of the cannabinoid standards and the quantities in which they are supplied. When preparing this type of calibration curve proper technique is critical since the higher calibration level has a considerable degree of leverage that can strongly influence the low end of the calibration curve. Table 2 shows the $R^2$ values for each of the analytes and all are >0.999.

Extensive method development and day-to-day application found that the lower calibration levels (0.016-0.250 mg/mL) and smaller injection volumes (1.5 uL) maintained resolution in real samples, eliminated retention time drift, and prolonged column life. Typically, close to 1000 injections can be performed before the guard column needs to be replaced.

TABLE 2

Correlation coefficients for the cannabinoid calibration curves

| Cannabinoid | $R^2$ |
|---|---|
| THCA | 0.9999 |
| CBDA | 0.9999 |
| THC | 0.9999 |
| CBD | 0.9999 |
| CBG | 0.9999 |
| CBC | 1.0000 |
| CBN | 0.9999 |
| D8-THC | 0.9999 |

Example 4—Calculations and Reporting

All instrumental assays for terpenes and cannabinoids at a single dilution ratio were configured to use the associated software packages (ChemStation C.01.06[61] on the Agilent 1290 and TotalChrom 6.3.2 on the Clarus 680) to calculate wt % values based on ISTD calibration curves, which was nonane (0.1 mg/mL) for the terpenes and IBU (0.2 mg/mL) for the cannabinoids. For analysis of both major and minor cannabinoids, which required two dilution factors, the intermediate values were obtained from ESTD calibration curves and reported as Raw wt %. In order to correct for recovery in the sample preparation and dilution process the final weight percent for each dilution factor, y, was calculated according to the following equation (vide infra):

$$\text{Final wt } \%_{DFy} = \text{Raw wt } \%/(1 + \% \Delta) \quad (1)$$

where:

$$\% \Delta = \frac{(A_{BPCA})_{Sample} - (A_{BPCA})_{Known}}{(A_{BPCA})_{Known}} \quad (2)$$

where:

and; $(A_{BPCA})_{Known}$ is the experimentally determined peak area of BPCA at dilution factor y and $(A_{BPCA})_{Sample}$ is peak area of BPCA found in the sample at dilution factor y PRSDs were calculated according to the equation:

$$PRSD = 2C^{-0.1505}$$

where C is the analyte concentration expressed as a mass fraction.

These correction factors were also programmed into ChemStation for automated reporting of both the raw results and the corrected values.

Thus, the present disclosure teaches methods of measuring cannabinoids and terpenes using three standards. The Ibu (0.2 mg/mL in initial extraction solution and dilution solution) and n-nonane (0.2 mg/mL in initial extraction solution and dilution solution) internal standards are present at known concentrations throughout the analysis process. These internal standards are thus independent of changes in dilution, because the concentrations remain unchanged. The third external standard, BPCA (e.g. 2.0 mg/mL only in extraction solution) is present at a known initial concentration, but is allowed to vary during processing or subsequent dilutions. In this way, the ratio of the first two standards to the third standard can be used to determine how much of the original extraction is actually measured.

Example 5—Sample Extraction

The null hypothesis for evaluating sample extraction was taken as 1000 mg of pre-ground sample, 15 mL of extraction solvent, and dilutions of Ix (neat), 6× and 96×. These parameters were chosen based on literature reviews (3, 4, 5, 6, 7), expected analyte concentration levels, and instrument calibration levels. These values allowed quantification of analytes in the ranges of 0.02%-1.5% for terpenes (1×), 0.14%-2.3% for minor cannabinoids (6×), and 2.3%-36% for major cannabinoids (96×). All extractions were performed with the 1600 MiniG reciprocating vertical disrupter (OPS Diagnostics) using 50 ml, polypropylene conical vials.

The extraction procedure was optimized for bead type, bead size, bead volume, and homogenization time (n=3). The robustness of the procedure with respect to solvent volume and sample size was evaluated (n=3). The robustness of the method with respect to sample phenotype/chemotype was evaluated by extracting five different cultivars (n=3), and these results were compared to typical sonication methods.

Example 6—Limit of Quantitation (LOQ)

The LOQ was determined experimentally by injecting standard solutions in triplicate. The LOQ was the concentration that provided results that were within 20% of the nominal value. The LOQ was 0.008 mg/mL for both the cannabinoids and the terpenes.

Example 7—Analysis

Precision

The instrumental precision was evaluated by injecting all standards in triplicate. The intra-day precision was evaluated by extracting and analyzing five different cultivars with different cannabinoid and terpene profiles five times on one day, while the inter-day precision was determined by extracting and analyzing the same cultivars on separate days.

Use of Check Standards

Check standards are a critical component to monitoring assay performance. The terpene check standard consists of a mixture of two monoterpenes, a terpenol, and a sesquiterpene with 0.1 mg/mL nonane. The cannabinoid check standard is a mixture of CBD, CBDa, THC, and THCA with 0.2 mg/mL ibuprofen. These are analyzed at the start, middle, and end of every sample set and the values are control charted. Values deviating by five percent indicate re-evaluation of the results and/or assay is required, however variation over the course of a run is typically less than one percent.

Application of the Method

As an example of the utility of this method, plants from a state-of-the-art production facility were sampled at the cultivation site to illustrate the variability that occurs with this agricultural crop. This method was also used to generate results that were compared to those obtained by other California analytical labs using different methodologies.

Example 8—Extraction Solvent, Diluent, and Internal Standards

The use of nonane as the internal standard for terpene analysis is analytically rigorous and compensates for variability in recovery and peak area in typical fashion. The use of both ibuprofen and BPCA in the cannabinoid assay, however, requires some discussion.

The method of using two different internal standards for different purposes was the result of several factors encountered during method development and sample analysis, 1) The availability, stability, cost, and supplied form of cannabinoid analytical standards can make it impractical for many labs to prepare multiple calibration solutions with different concentrations of internal standards. 2) The linear range of the cannabinoid assay was approximately 1.5 orders of magnitude (0.016-0.250 mg/mL), however analyte concentrations can span over 2 orders of magnitude (0.1%-40% by weight), and this requires separate dilution ratios for both the minor and major cannabinoids to remain in the linear range of the calibration curve. 3) When testing unknown samples (especially water hash and extracts), the cannabinoid concentrations are unpredictable and can be even higher (as high as 80% by weight). Since the sample has already been processed, the only way to bring the properly stored extraction slurry (4 C for no longer than 24 hours) into the linear range for reanalysis is to use a larger dilution factor.

When an assay and calibration curves are developed with an internal standard present, the concentration of the internal standard in the final aliquot for analysis must remain fixed at the level used to generate the calibration curves. If it is anticipated a sample is "typical" and only the major cannabinoid profile is desired (2.5%-36% by weight with the given mass and solvent ratios), only a single 96-fold dilution is needed. In this case, spiking the sample with 1 mL of internal standard spike solution, adding 14 mL of diluent, extracting the sample, and then diluting 96-fold provides an aliquot for analysis with a theoretical 0.2 mg/mL IBU for analysis with the HPLC method that utilizes the ISTD curve.

While the use of IBU as the internal standard in the aforementioned manner is analytically rigorous and is employed by our laboratory at times, we typically use the method described herein where BPCA is used as the internal standard. In this case the surrogate is added to the sample at a fixed concentration via the extraction solution and variation in analyte recovery due to sample preparation and/or dilution is estimated by the recovery of the surrogate, which can then be used as a correction factor for the raw result. The instrument parameters are set to use the ESTD calibration curves, and a correction factor given by Equation 1 is applied to the raw result. This procedure is also analytically rigorous, and while it does not benefit generation of the calibration curves as with the first method, careful method development to ensure linearity and injection precision mitigates this issue. This procedure has the added benefits that it does not rely on the precision and/or accuracy of internal standard spikes by different lab technicians, and it can be applied to any dilution ratio needed by comparing the experimental peak area of the surrogate to the known peak area of the surrogate determined at each concentration.

In this specific case, the extraction solution with BPCA at 2.0 mg/mL is diluted 6-fold (0.333 mg/mL) and 96-fold (0.021 mg/mL) in replicate and the average peak areas are determined. The correction for recovery is then given by Equation 1 for each of those dilution factors. If a processed sample is found to be outside the linear range of the calibration curve a correction factor can quickly be determined at a different dilution ratio, and the properly stored extract re-diluted for analysis. This process is much faster than preparing new calibration solutions of expensive cannabinoid standards with internal standards at the appropriate concentrations and recalibrating the instrument. Typically, the reporting methods and appropriate correction factors for several dilution factors are stored in the ChemStation software and simply applied to the individual sample dilutions as needed.

Figure 6:
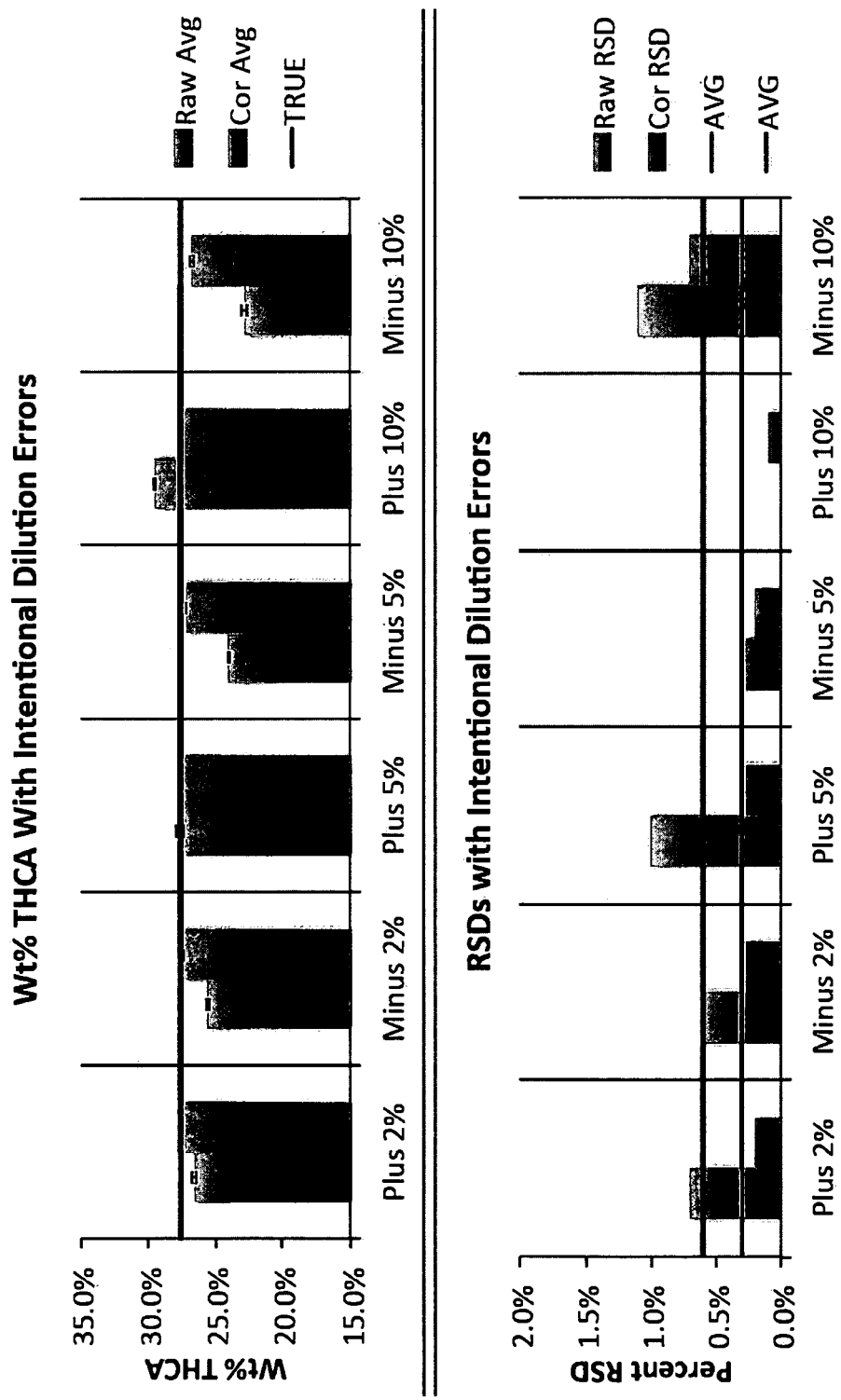
FIG. 6—Accuracy (with 95% CI) and precision for corrected and uncorrected THCA values.

FIG. 6 shows the result of this correction (at a 96-fold dilution) for an extract subjected to intentional dilution errors in replicate (n=5). In all cases the raw value is corrected to the true value and the average RSD is less than 0.5%. This has been verified for a number of other dilution factors as well and the amount of BPCA present in the working solution can be changed to levels more suited to different ratios (data not shown).

To demonstrate the use of this correction again, a $CO_2$ wax was analyzed for THCA by dissolving the wax in a suitable volume of extraction solution in a volumetric flask as to not require any dilution for analysis (n=2) and the average was taken as the "true" value. The wax was then reanalyzed by dissolving in 267 mg 10 mL of extraction solution and diluting 96-fold in the typical manner, as well as intentionally adding 20% more and 20% less of the extract (n=5 for each). The process was then repeated by dissolving in 168 mg is 100 mL of extraction solution and diluting 6-fold in the typical manner, as well as introducing the same intentional dilution errors (n=5 for each).

Table 3 shows the results for both corrected and uncorrected values. In all cases the corrected values are much closer to the true value, RSDs are reduced by half, and the relative error is also greatly reduced. While gross errors such as an error of 20% in sample volumes still show some deviation from the true value, they are still reasonable and typical dilution errors are easily compensated for as shown by the first set of dilutions. This also demonstrates the ability of a single BPCA concentration to compensate for recovery at both a 6-fold (169 mg in 100 mL) and 96-fold (267 mg in 10 mL) dilution.

TABLE 3

Error correction with internal standards

| | Raw | | Corrected | | Relative Error | | RSD | |
|---|---|---|---|---|---|---|---|---|
| | Avg | ± | Avg | ± | Raw | Corr. | Raw | Corr. |
| "True" | 73.8% | 1.56% | 73.8% | 1.56% | 0.0% | 0.0% | 2.1% | 2.1% |
| 96-fold | 68.3% | 0.69% | 73.6% | 0.24% | −7.4% | −0.2% | 1.0% | 0.3% |

TABLE 3-continued

| | Raw | | Corrected | | Relative Error | | RSD | |
|---|---|---|---|---|---|---|---|---|
| | Avg | ± | Avg | ± | Raw | Corr. | Raw | Corr. |
| 6-fold | 72.2% | 0.61% | 75.7% | 0.29% | −2.2% | 2.6% | 0.8% | 0.4% |
| 96 + 20% | 83.28% | 1.02% | 73.88% | 0.25% | 12.8% | 0.1% | 1.2% | 0.3% |
| 6 + 20% | 84.15% | 0.93% | 77.40% | 0.14% | 14.0% | 4.9% | 1.1% | 0.2% |
| 96 − 20% | 56.77% | 1.06% | 73.14% | 0.38% | −23.1% | −0.9% | 1.9% | 0.5% |
| 6 − 20% | 59.26% | 1.07% | 73.54% | 0.38% | −19.7% | −0.4% | 1.8% | 0.5% |

Figure 27:
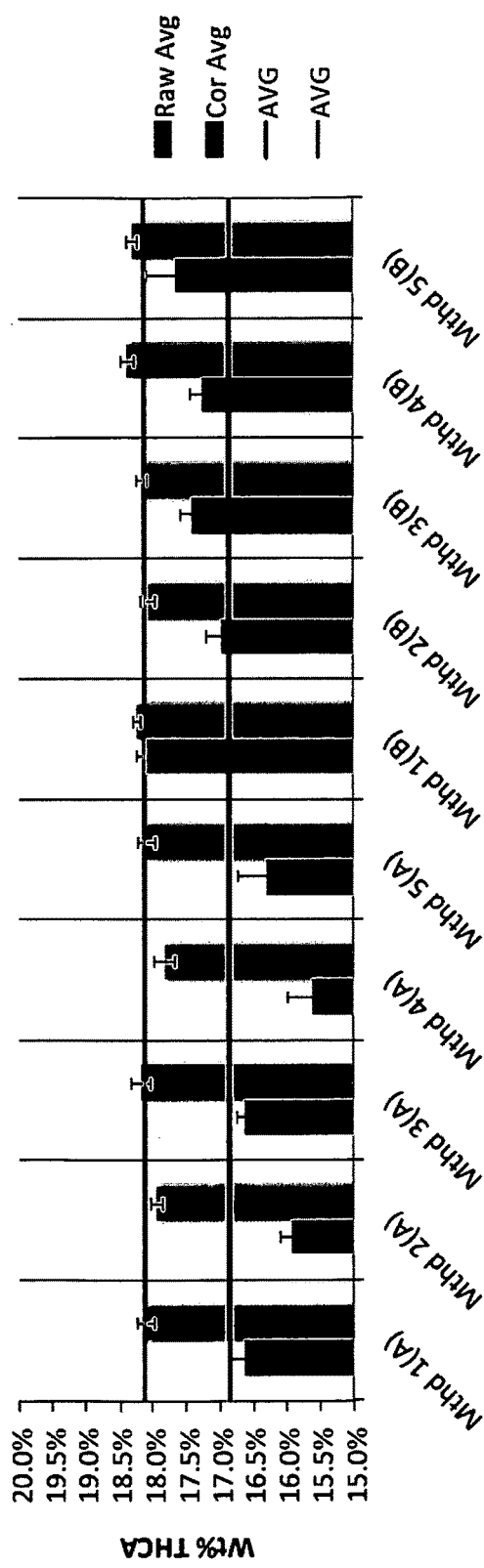
FIG. 27—Comparison of "measured" THCA content as obtained by two technicians (A and B) using various methods for pipetting samples in a blind experiment. The methods presented in this experiment include standard with pre-wetting the tip (1), reverse pipette (2), standard with rinsing the pipette tip in the diluent (3), multichannel pipette (4), and serial dilution (5). Values for raw data and corrected average using the methods of the present invention are shown for each method and technician. Corrected average corrects for technical errors to produce more precise results.
Figure 27:
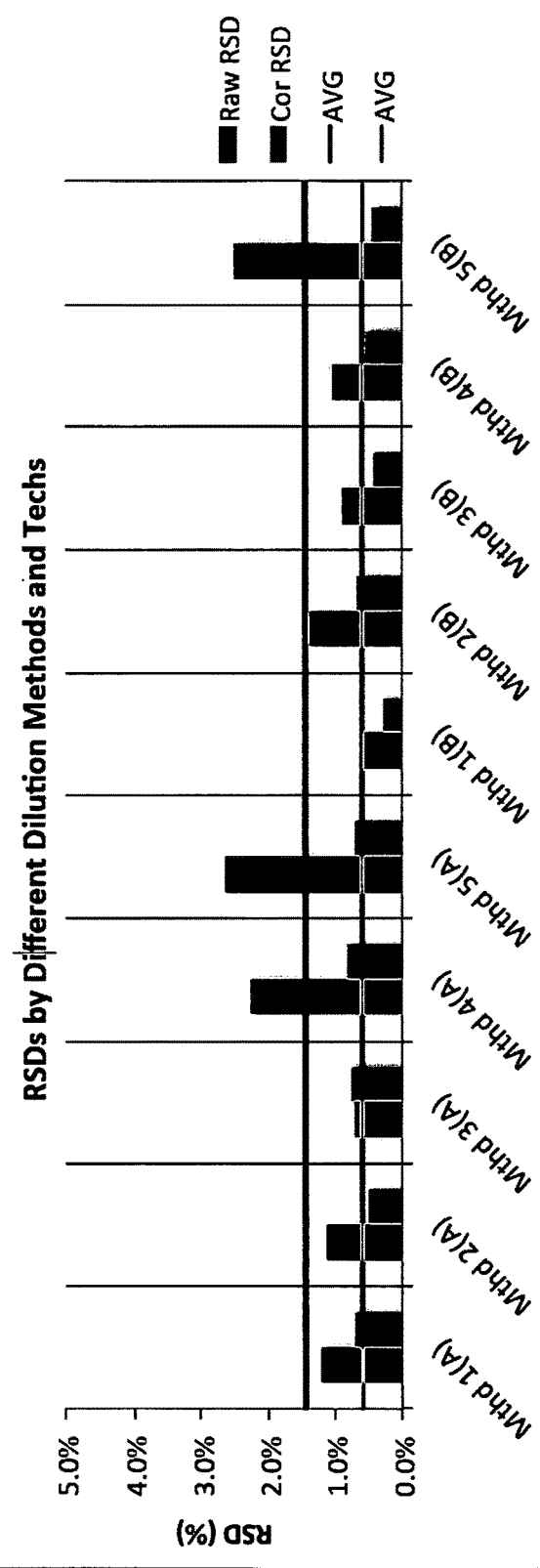

To demonstrate the applicability to typical sample processing, a sample of flowers was homogenized in a stainless steel coffee grinder and two different technicians each analyzed five separate samples in replicate (n=5) using a different pipette technique for diluting each sample. The techniques were standard with pre-wetting the tip (1), reverse pipette (2), standard with rinsing the pipette tip in the diluent (3), multichannel pipette (4), and serial dilution (5). They were specifically instructed to show "less care", so this was not an evaluation of the various pipetting techniques. In this case the "true" value is not known since it is being determined by the analyses so the average values are represented as the lines in FIG. 27. For the uncorrected wt % values the overall average is lower and there is a clear systematic error related to the technician, with technician A always generating lower values than technician B. The corrected wt % values, however, are all very similar regardless of the pipette technique used or the technician. The RSDs are shown in the lower chart and on average the RSDs using the correction factor are half that of those not using the correction factor. This suggests that using BPCA as a surrogate to correct for recovery is quite applicable to the typical workflow in the laboratory.

If the samples generally have known analyte concentrations and ranges, the linear range of the assay, volumes of spike solution with IBU, and dilution ratios can be tailored to use a single internal standard (IBU) in the typical fashion with the ISTD calibration curves. Verifying a wider linear range for a single calibration curve would simplify the situation, however a linear calibration range (as determined via analysis of both correlation coefficients and residuals) on an HPLC-UV assay over 2 orders of magnitude (for concentrations of THCA from 0.1% to almost 40%) can be difficult to attain. Likewise, once cannabinoid standards are made available in pure solid forms it will become easier to prepare multiple calibration solutions with different internal standards and concentrations. However, for a lab processing a large amount of unknowns, having a second method that used a surrogate (BPCA) to correct for recovery at any dilution factor provided a pragmatic solution that minimized variability and systematized the process while still accommodating the wide range of analyte concentrations. There are some well-known limitations to using a single surrogate at a single concentration to approximate the behavior of a number of analytes with a wide range of concentrations, however method development and validation suggest this process performs adequately for this assay.

Example 9—Optimization of the HTH Parameters

High Throughput Homogenizers (HTH) have been used for homogenizing microorganisms, plant tissues, and animal tissues using a variety of grinding media and formats that range from 96-well plates to 125 mL plastic serum bottles (13). The key to effective homogenization is to find the optimal combination of sample mass, solvent volume, bead type, bead volume, and vessel volume for the sample being extracted in order for the grinding media to freely impact the sample. More sophisticated homogenizers allow for a wider range of variables to be manipulated to ensure optimal extraction. Based on expected analyte concentrations and the desire to use relatively larger sample masses to improve reproducibility, initial parameters for sample mass and extraction volume were 1000 mg and 15 mL, respectively. These sizes required 50 mL polypropylene conical vials, and bead material, bead size, bead volume, and extraction time were evaluated.

The absolute quantities extracted and the RSDs were evaluated for each analyte and for the overall totals. Only the totals will be discussed in the interest of brevity since, with very rare exception, they closely mirrored the results for the individual analytes.

Figure 7:
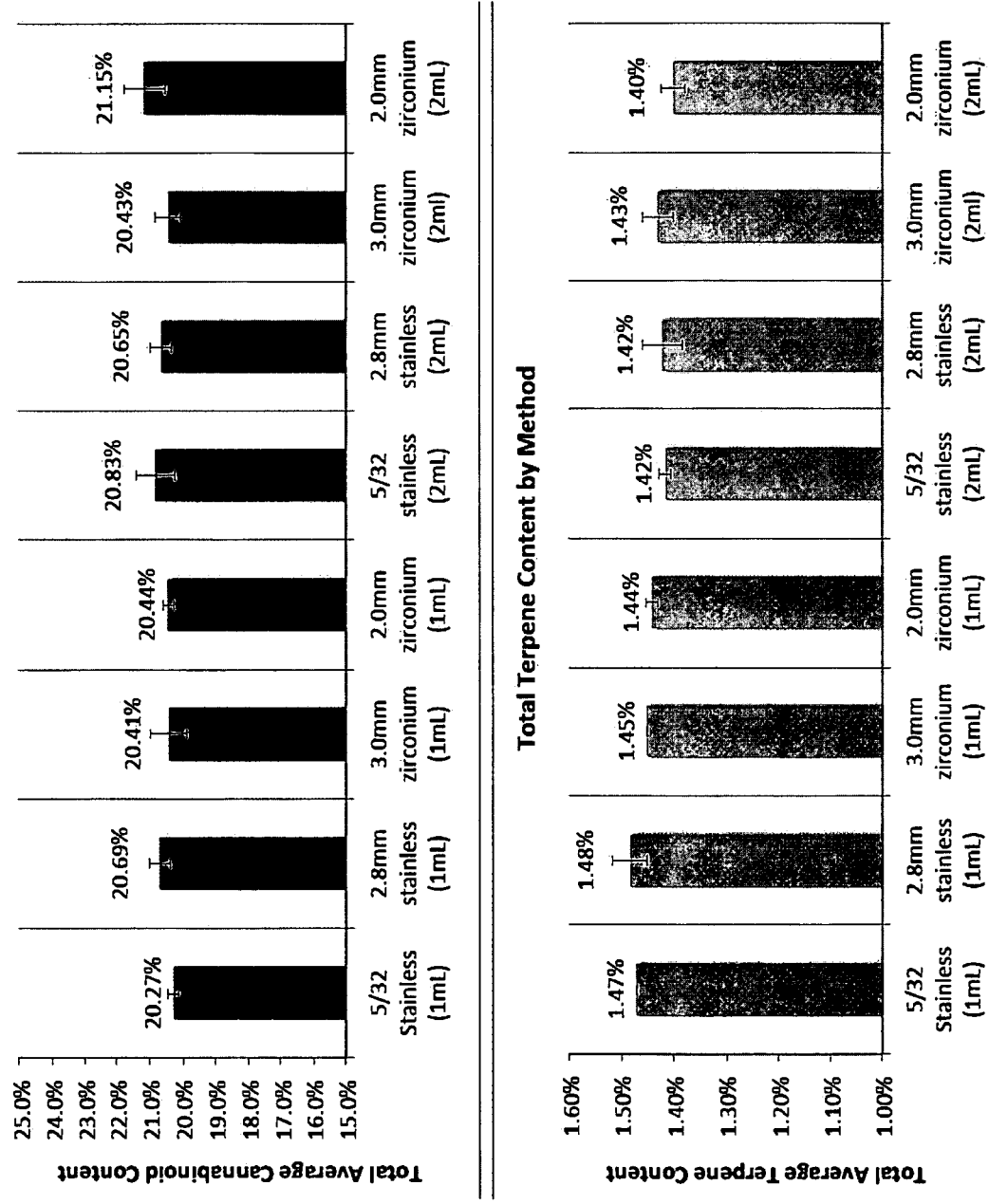
FIG. 7—Extractions (with 95% CI) with different bead variables.
Figure 8:
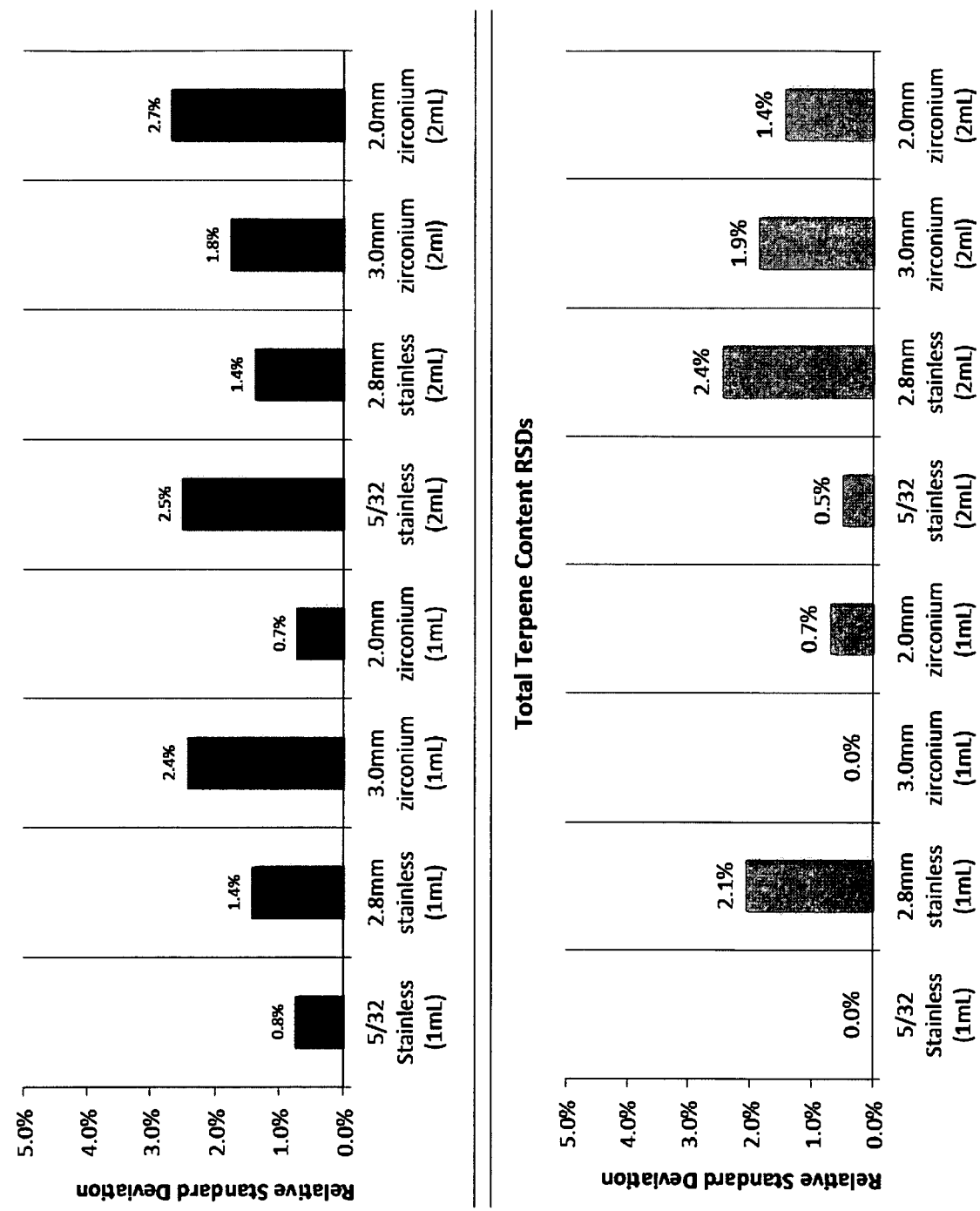
FIG. 8—RSDs with different bead variables.

First, bead type and size were assessed using 1 mL or 2 mL volumes of beads and four different bead sizes and materials. FIG. 7 shows the absolute quantities of terpenes and cannabinoids extracted by the different methods and FIG. 8 shows the RSDs for the different methods. While there were no clear overall trends, in general it appeared the smaller volume of beads provided better RSDs in both types of analytes, and slightly improved total recovery for terpenes. A volume of 1 mL of 2.0 mm zirconium beads provided the lowest RSD for all analytes and was selected as the bead type.

Figure 9:
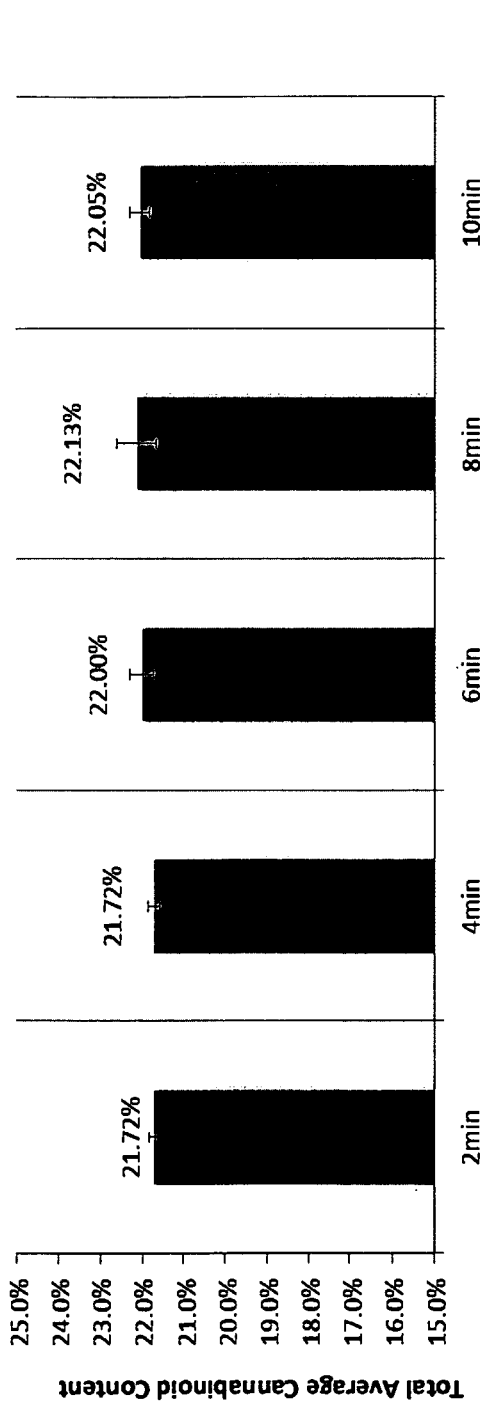
FIG. 9—Extractions (with 95% CI) with different times.
Figure 9:
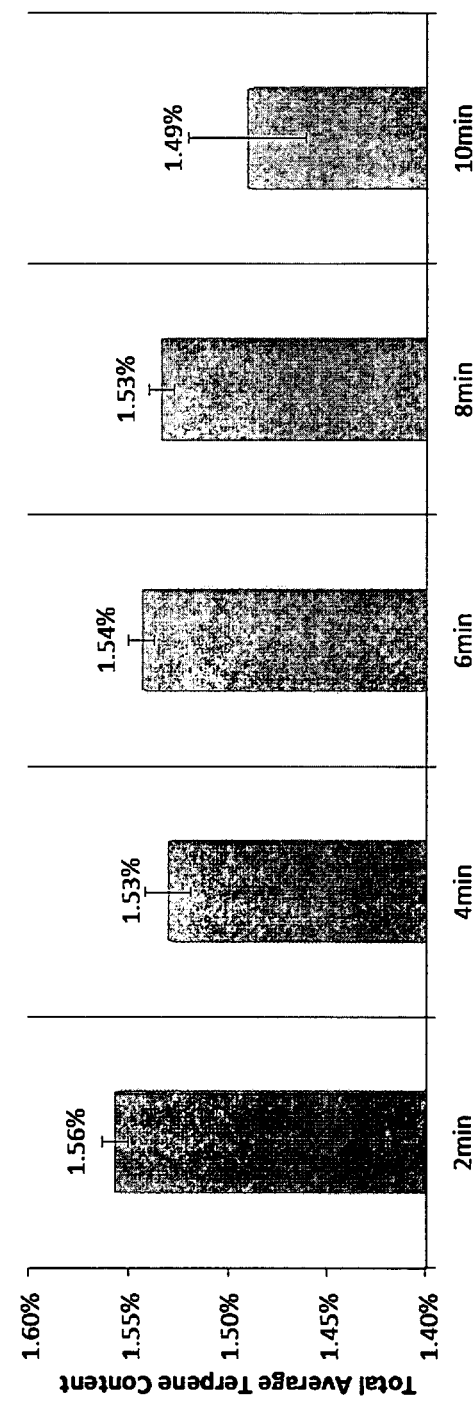
Figure 10:
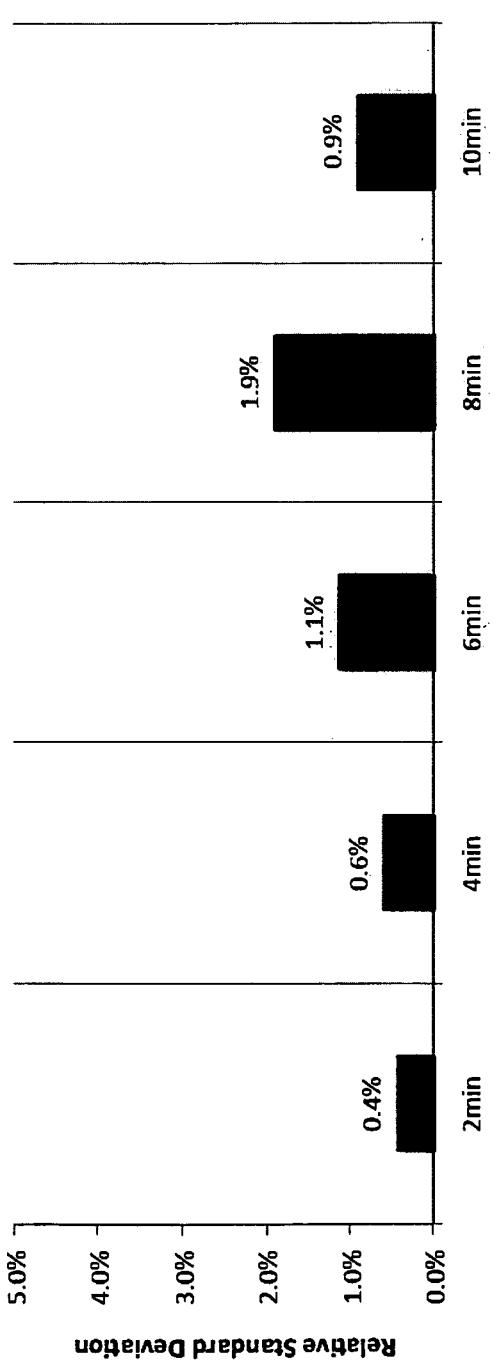
FIG. 10—RSDs with different times.
Figure 10:
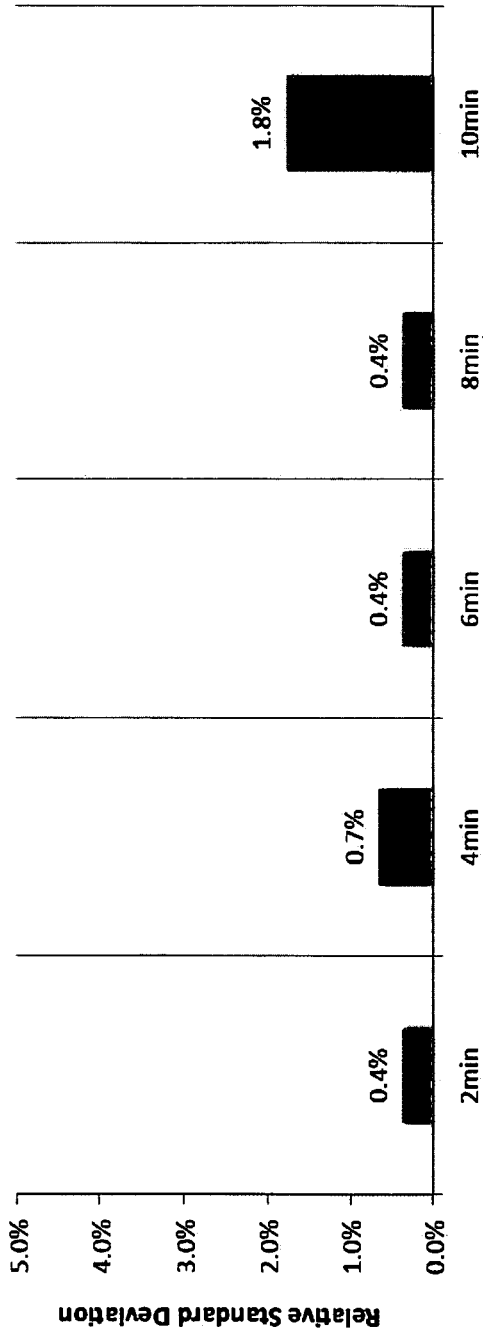

Second, the effect of homogenization time on the total amount extracted and the RSDs was evaluated. FIGS. 9 and 10 show the results of this evaluation. Although there was little effect on total cannabinoid content, there was a very slight decrease in the total terpene content extracted with increasing time. This was mainly driven by a decrease in the content of myrcene. Furthermore, the cannabinoid RSDs trended upwards with increased extraction time. Considering the extraction totals and RSDs for each analyte class, six minutes was chosen as the optimal extraction time.

Example 10—Robustness of HTH Extraction

The robustness of the HTH extraction process was evaluated with respect to solvent volume, sample mass, and sample moisture. The robustness was also evaluated with respect to cultivar and was compared to sonication procedures (sonication for 30 minutes). As with optimization of the HTH parameters, each analyte was examined but only the totals are shown as they closely mirrored the individual analytes.

Figure 11:
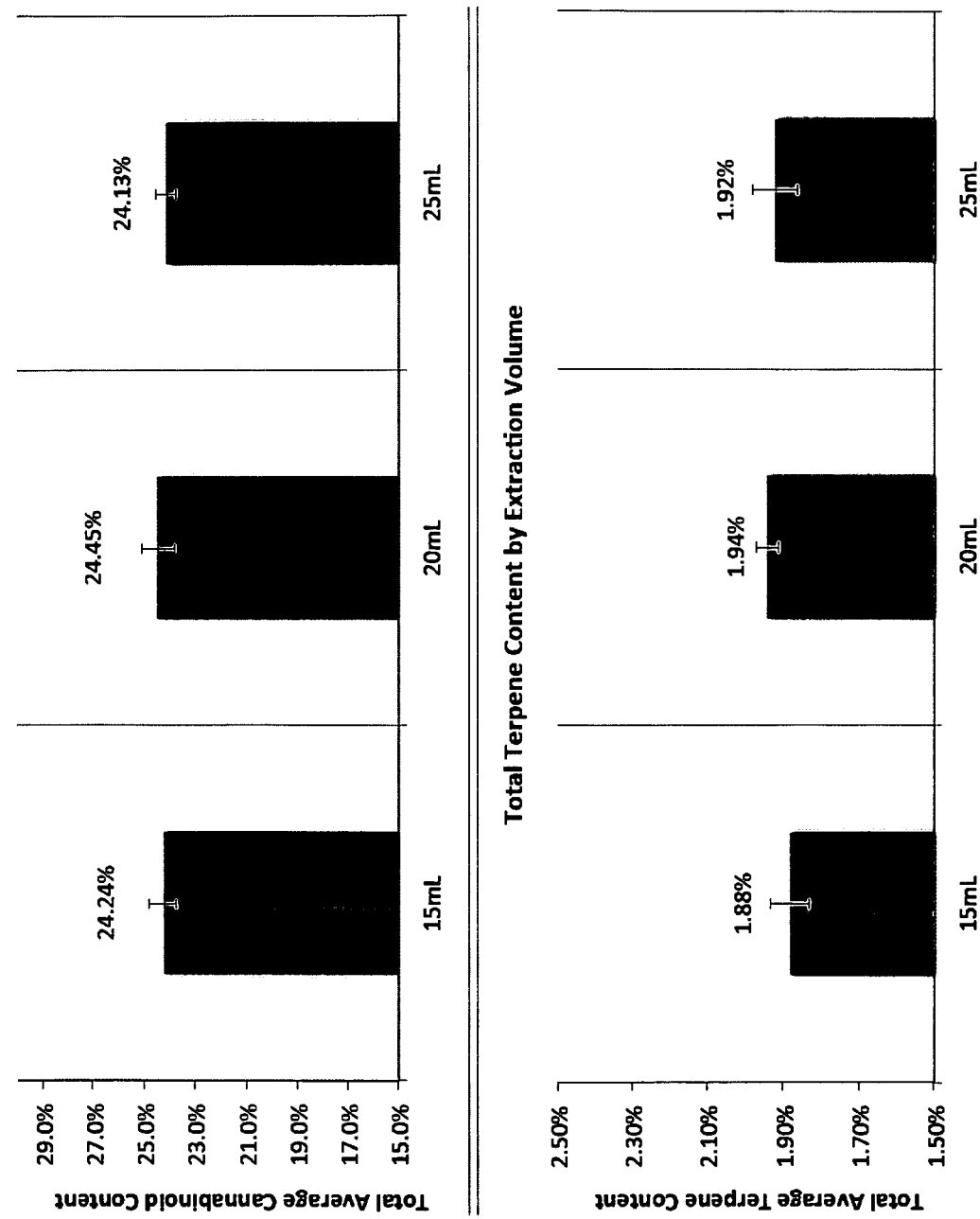
FIG. 11—Extractions (with 95% CI) with different volumes of extraction solution.
Figure 12:
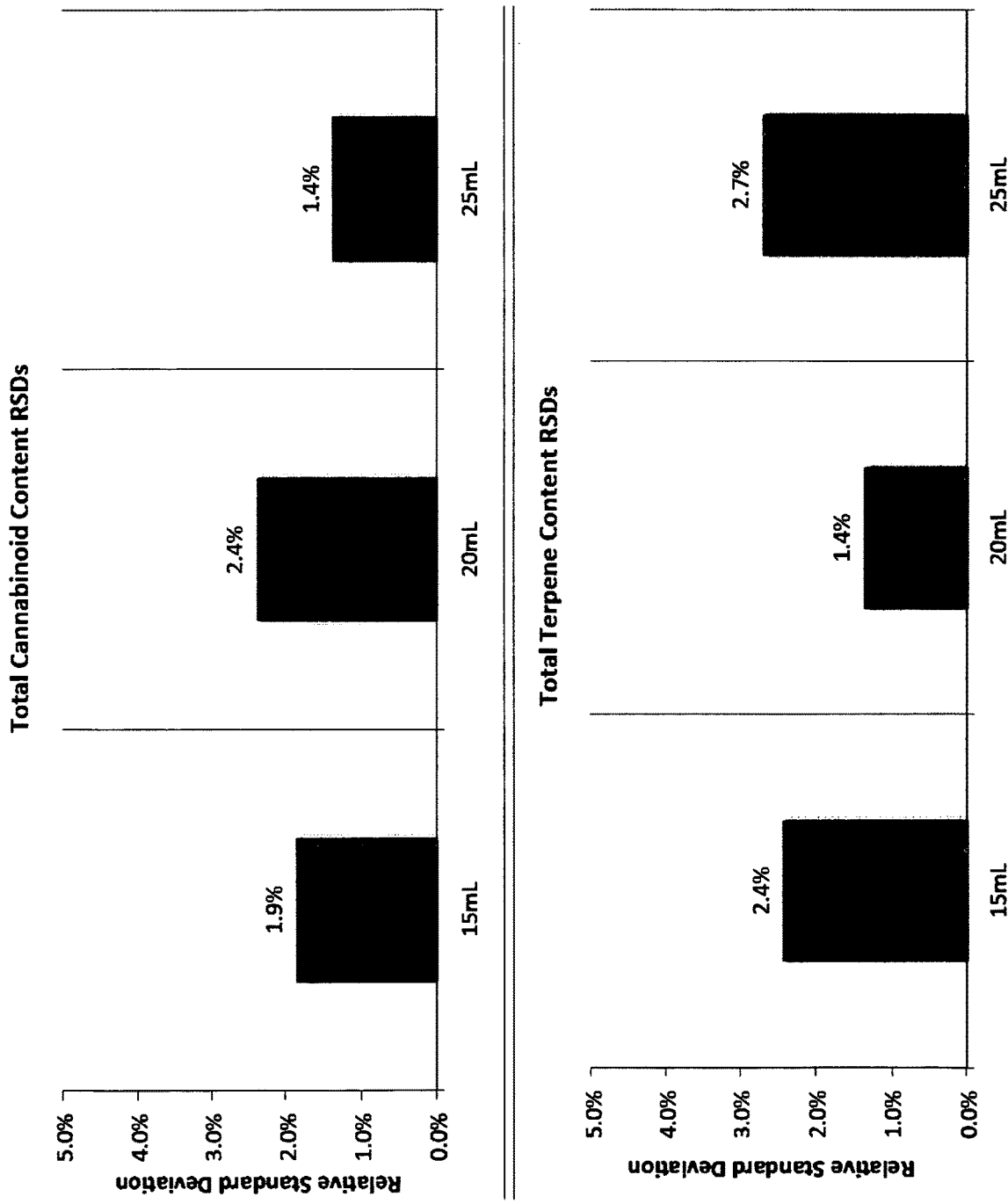
FIG. 12—RSDs with different volumes of extraction solution.

FIGS. 11 and 12 show the results for increasing the volume of the extraction solvent in an attempt to improve extraction efficiency. Increasing the solvent volume did not appear to affect either the extraction totals or the RSDs for either class of analytes, therefore 15 mL was chosen as the extraction volume in order to maintain a higher concentration of terpenes in the extract. Since the extraction was quite robust with respect to solvent volume, it can be increased or decreased to accommodate higher or lower anticipated levels of analytes, respectively.

Figure 13:
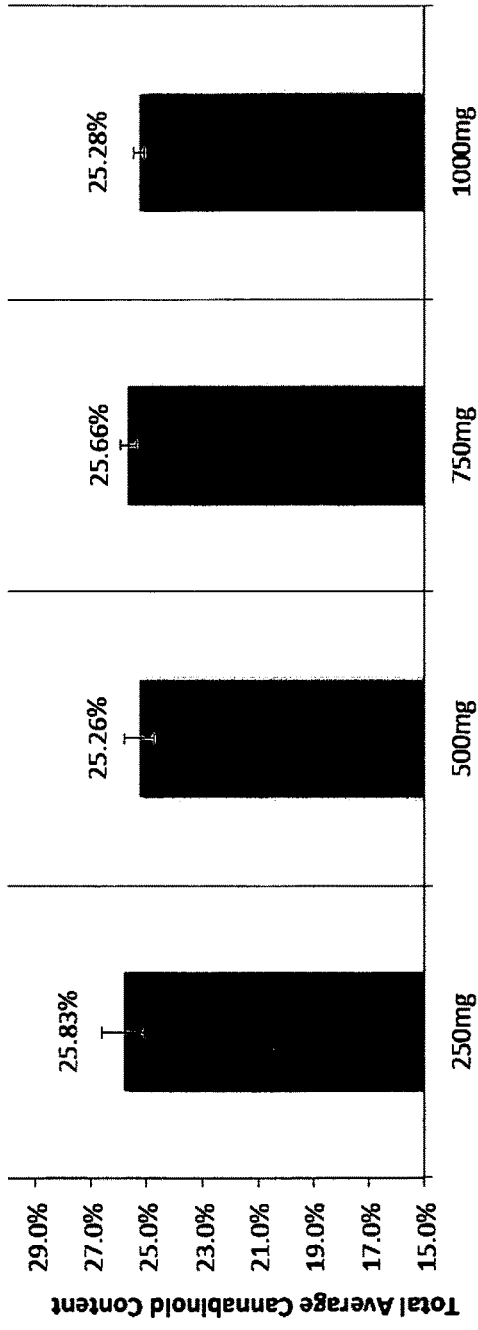
FIG. 13—Extractions (with 95% CI) with different masses of cannabis samples.
Figure 13:
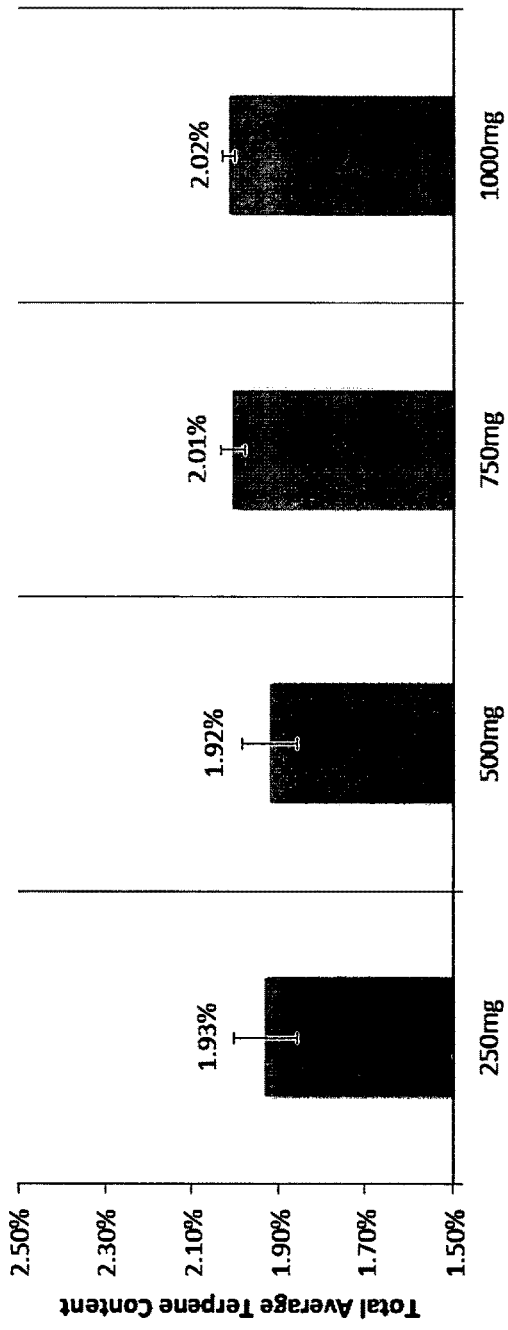
Figure 14:
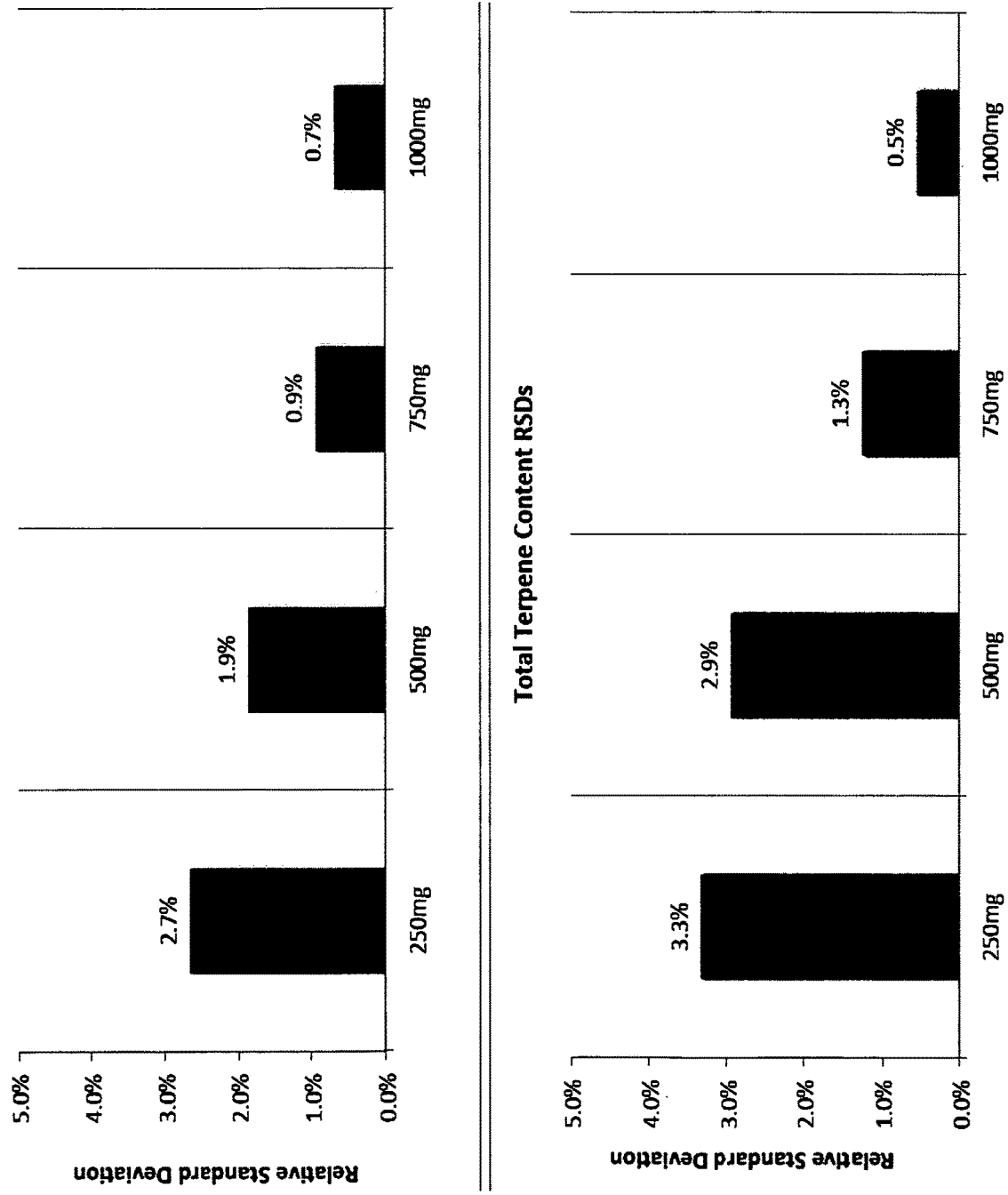
FIG. 14—RSDs with different masses of cannabis samples.

FIGS. 13 and 14 show the results of altering the sample mass that is extracted while maintaining the same ratio of solvent and grinding beads to sample mass. It can be seen that the smaller sample size results in larger RSDs, and this can be expected from non-homogeneous samples such as ground flowers. Increasing the amount of ground material extracted to 1000 mg reduced variability in sampling of the cultivar. No significant trends were seen in the total content of either analyte class.

The robustness of the procedure with respect to cultivar was also evaluated. This is an important step since there is a very wide range of morphologically different flowers that very often contain distinct analyte profiles. While it is not possible to do this for every different cultivar, five cultivars (Pincher's Creek, Canna-Tsu, a proprietary hybrid. Classic Trainwreck and Master Kush) were chosen to cover varying flower morphologies, from loose to compact, and a variety of cannabinoids and terpenes. These same five cultivars were also extracted by traditional sonication procedures and the results were compared to the HTH procedure.

Figure 15A:
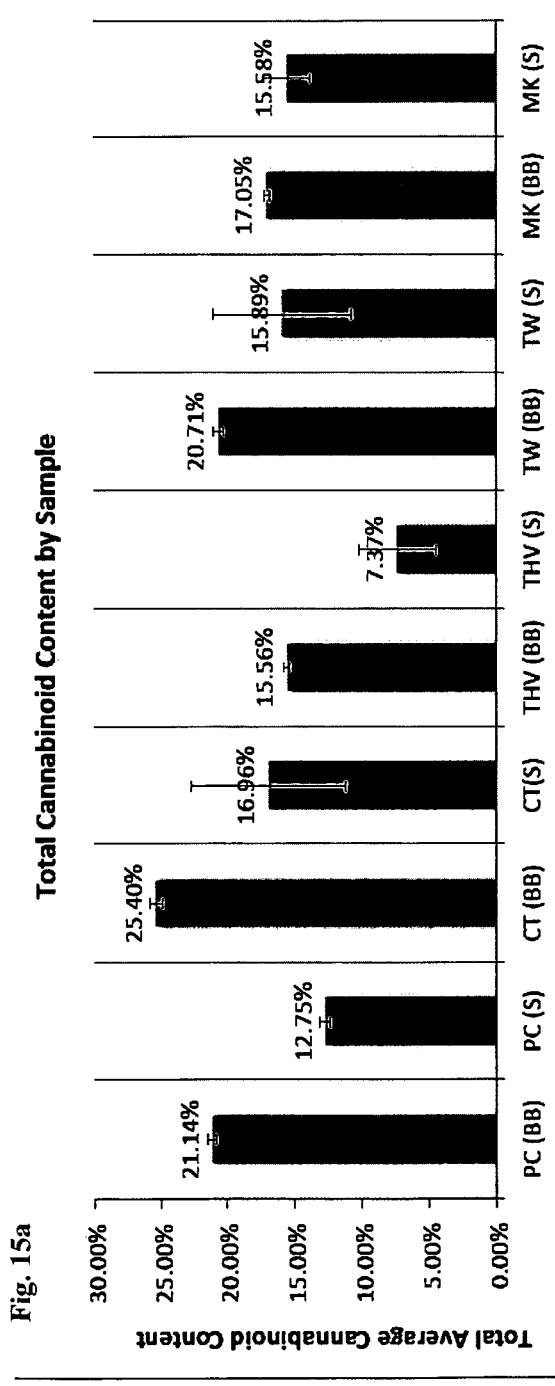
FIG. 15—(A)—Cannabinoid and terpene extraction totals (with 95% CI) and (B)—RSDs for five different cultivars (n=5 each) extracted by bead beating (BB) and sonication (S).
Figure 15B:
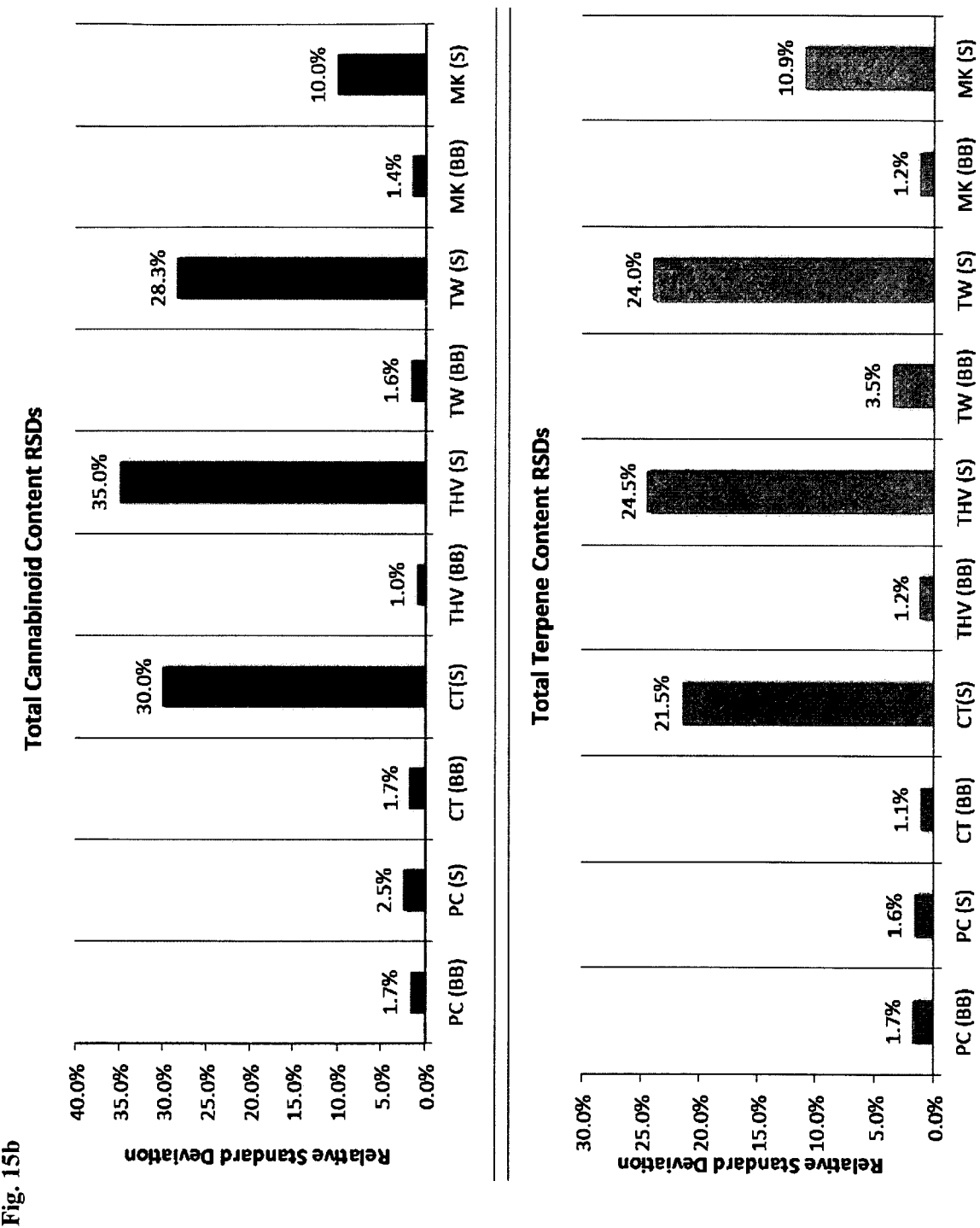

The results for bead beating (BB) and sonicating (S) the five cultivars are shown in FIG. 15. Total extraction for both cannabinoids and terpenes was significantly higher with bead beating than with sonication, almost double for some cultivars. The RSDs were also significantly lower with bead beating than with sonication and average bead beating RSDs across all cultivars was 1.5% for cannabinoids and 1.7% for terpenes, opposed to 21.2% and 16.5% (respectively) for sonication.

It's important to acknowledge that recommended sonication parameters in the literature for the extraction of cannabinoids typically use much larger solvent to sample mass ratios, which undoubtedly improves extraction efficiency. However, these larger ratios not only increase the amount of solvent needed for analysis but also reduce the concentrations of many terpenes in the resulting extract to levels that result in unacceptable detection limits, so parameters that were optimized for bead beating were employed. The higher RSDs noted with sonication may also have been due to different locations of sample tubes within the sonication bath, as well as differing flower morphologies. The HTH mitigates all of these issues and this is a critical feature of a high throughput method.

Example 11—Terpene Spike Recovery

Precision and relative bias for the terpenes was evaluated by spiking standards at low, medium, and high concentrations (n=5) into cannabis that had been stripped of all terpenes by pentane extraction. Rather than spike in each terpene individually, a solution of all of the terpenes in working solution was made at a concentration of 5 mg/mL. This solution was then used to spike the terpenes into 1000 mg of blank cannabis, giving terpene concentrations of approximately 0.025%, 0.175%, and 1.500% in the blank matrix. A volume of extraction solvent was then added such that the total volume (extraction volume plus spike volume) equaled 15 mL. Table 4 shows the exact weight percent of each terpene added to the matrix by the spikes.

Figure 16:
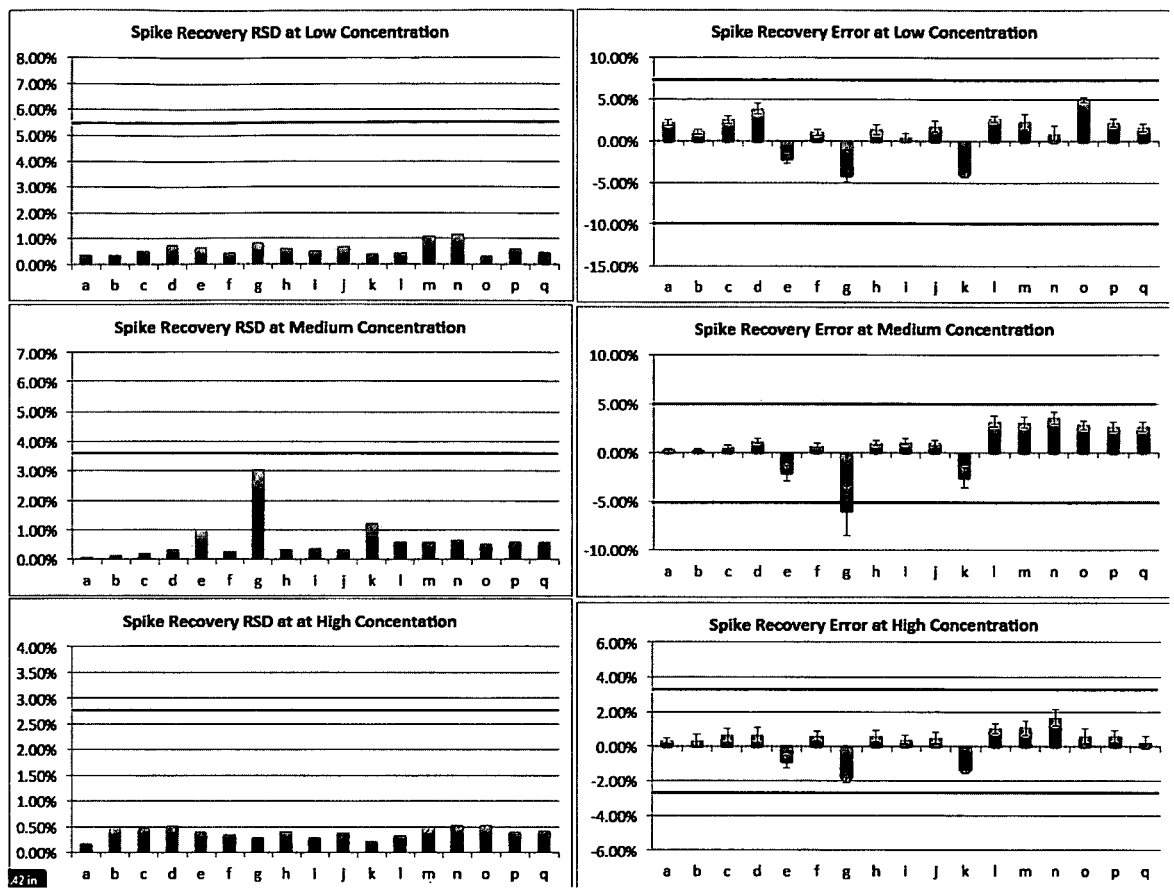
FIG. 16—Terpene precision and spike recovery (with 95% CI) error at high, medium, and low concentrations (n=5). The horizontal red lines on the charts indicate the accepted PRSDs and errors in recovery at the respective orders of magnitude.

In order to evaluate the precision and relative bias of the terpene assay, a solution was used to spike nominal values of 0.24 mg, 1.88 mg, or 15 mg of the terpenes into 1000 mg of blank cannabis, giving terpene concentrations of approximately 0.024%, 0.188%, and 1.500% in the blank matrix (see Table 4). The charts in FIG. 16 show the precision and spike recovery error (along with 95% confidence intervals) for each of the terpenes at low, medium, and high concentrations (n=5). The red lines on the charts indicate the accepted PRSDs and errors in recovery at the respective orders of magnitude (14). In all cases the values meet accepted limits with exception to alpha-terpinene error at the medium level.

Note that all three terpinenes (Alpha-phellandrene, alpha-terpinene, and terpinolene) exhibit low recoveries. This is a real effect and has been found to occur in extracts kept in clear vials, as was the case for these spike recovery studies. This does not occur with standards kept in clear vials, and the rate of decomposition in extracts is reduced dramatically when amber vials are used (data not shown). If extracts are not to be analyzed immediately, they should be placed in amber vials while awaiting analysis in order to ensure accurate results for these analytes.

TABLE 4

Average (n = 5) terpene concentrations spiked into matrix

| Terpene | Low (Wt %) | Med (Wt %) | High (Wt %) |
|---|---|---|---|
| terpinolene | 0.025 | 0.182 | 1.440 |
| α-phellandrene | 0.025 | 0.182 | 1.535 |
| β-ocimene | 0.025 | 0.180 | 1.443 |
| Δ3-carene | 0.025 | 0.179 | 1.423 |
| limonene | 0.025 | 0.180 | 1.458 |
| γ-terpinene | 0.024 | 0.181 | 1.461 |
| α-pinene | 0.025 | 0.178 | 1.455 |
| α-terpinene | 0.023 | 0.176 | 1.474 |
| β-pinene | 0.025 | 0.177 | 1.443 |
| fenchol | 0.024 | 0.172 | 1.428 |
| camphene | 0.026 | 0.175 | 1.513 |
| α-terpineol | 0.025 | 0.173 | 1.452 |
| α-humulene | 0.025 | 0.174 | 1.451 |
| β-caryophyllene | 0.024 | 0.174 | 1.414 |
| linalool | 0.025 | 0.172 | 1.412 |
| caryophyllene oxide | 0.023 | 0.174 | 1.400 |
| myrcene | 0.025 | 0.179 | 1.462 |

Example 12—Cannabinoid Spike Recovery

Since analytical standards are not available in quantities required for evaluating spike recovery at realistic concentrations, three separate pentane extracts (A, B, and C) were generated, the acidic cannabinoids were quantified, and they were spiked back into 1000 mg of the extracted blank matrix at low, medium, and high concentrations (n=5). The extracts were then heated at 240° C. for 15 minutes to provide three more extracts (D, E, and F) with the neutral cannabinoids. Since there was not a clearly dominant CBGA cultivar available for extraction, evaluation of CBG(A) was carried out with the same extract used for evaluating THC(A). Table 5 shows the weight percent of each cannabinoid added to the matrix by the spikes.

It should also be noted that two separate blank matrices (X and Y) were used. Repeated passive pentane extraction always left residual amounts of the cannabinoids in the blanks when analyzed after bead beating. In order to minimize the effects of this residual background, the blank with the lowest amount of residual analyte corresponding to the analyte being spiked was used. The combinations are also shown in Table 5. The residual background amount of each analyte was subtracted from each of the spike recovery results. Table 6 shows the residual analyte remaining in each of the blank matrices.

To evaluate the precision and relative bias for cannabinoids, concentrated extracts were made containing THC(A), CBD(A), THCV(A), and CBG(A) and were spiked back into the blank matrix. Levels found in each extract determined the high, medium, and low levels for each analyte. THC(A) and CBD(A) were more concentrated and could be spiked in at higher levels than THCV(A) and CBG(A) (see Table 5).

TABLE 5

Average spiked cannabinoid concentrations

| Cannabinoid | Spike | Low (Wt %) | Med (Wt %) | High (Wt %) | Blank Matrix |
|---|---|---|---|---|---|
| THCA | A | 0.21 | 9.4 | 33.64 | Y |
| CBDA | B | 0.26 | 9.89 | 31.48 | X |
| CBGA | A | 0.17 | 3.16 | 7.56 | Y |
| THCVA | C | 0.21 | 4.54 | 15.57 | Y |
| THC | D | 0.41 | 8.84 | 30.08 | Y |
| CBD | E | 0.22 | 15.63 | 33.37 | X |
| CBG | D | 0.18 | 2.75 | 6.03 | Y |
| THCV | F | 0.28 | 5.54 | 19.15 | Y |

TABLE 6

Residual analyte background

| Cannabinoid | Matrix X (Wt %) | Matrix Y (Wt %) |
|---|---|---|
| THCA | 0.048 | 0.009 |
| CBDA | 0.004 | 0.263 |
| CBGA | 0.020 | 0.044 |
| THCVA | ND | ND |
| THC | 0.006 | 0.001 |
| CBD | ND | 0.009 |
| CBG | ND | ND |
| THCV | ND | ND |

Figure 17:
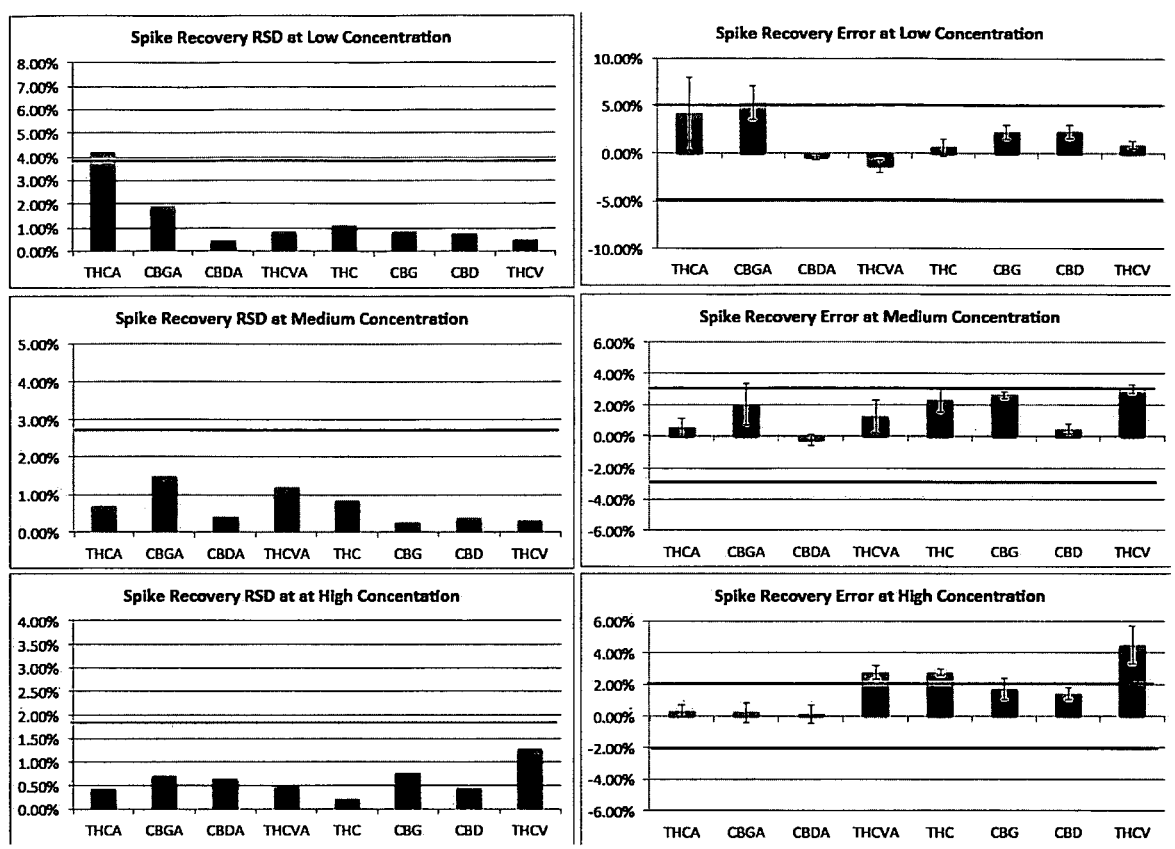
FIG. 17—Cannabinoid precision and spike recovery (with 95% CI) error at high, medium, and low concentrations (n=5). The horizontal red lines on the charts indicate the accepted PRSDs and errors in recovery at the respective orders of magnitude.
Figure 18A:
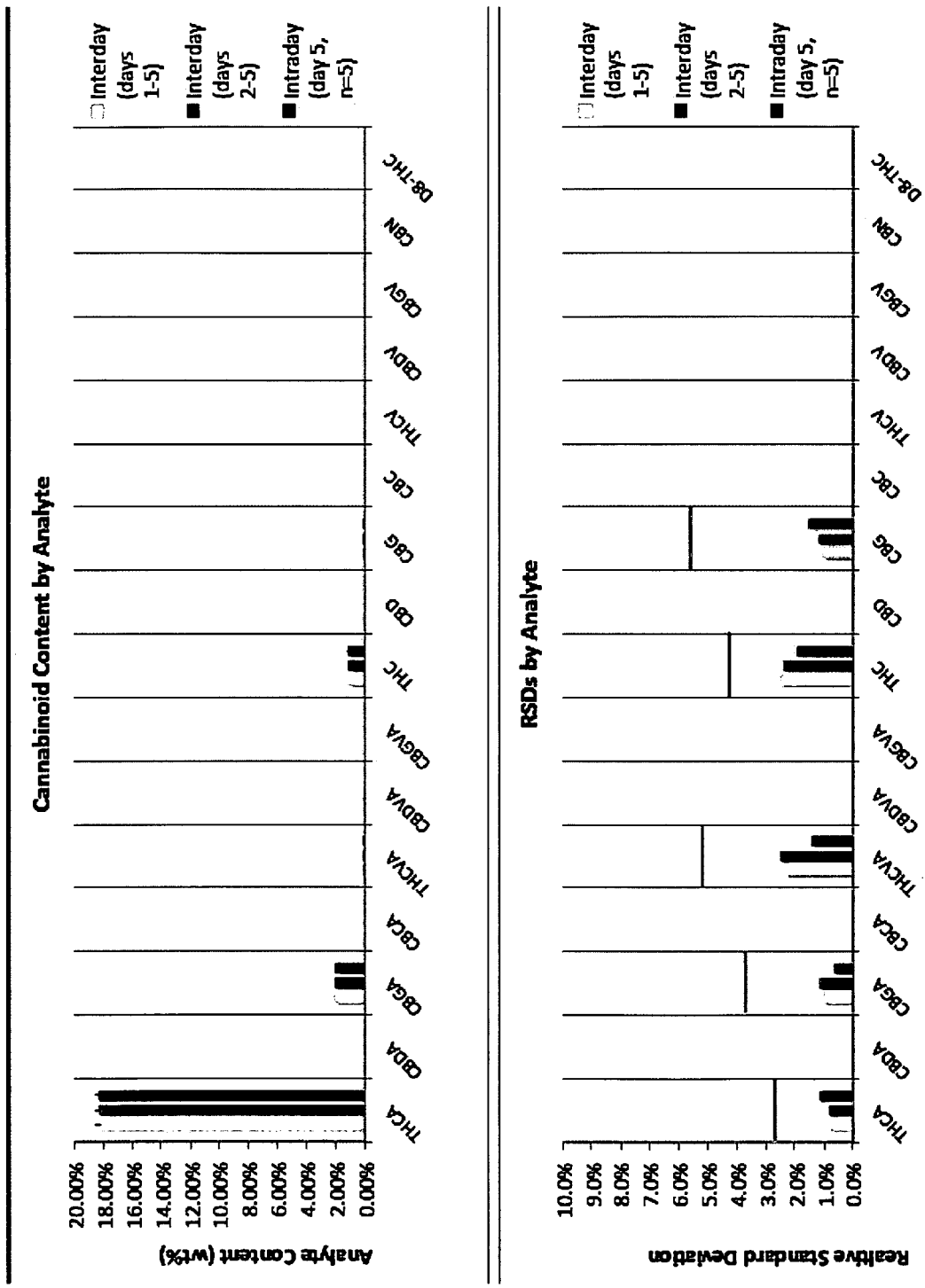
FIG. 18—Intra-day and inter-day analyte content and precision for Pincher's Creek variety. (A)—Inter-day and intra-day cannabinoid content. (B)-Inter-day and intra-day terpene content. The PRSDs for each analyte at the determined concentrations are also indicated on the chart by horizontal red lines.
Figure 18B:
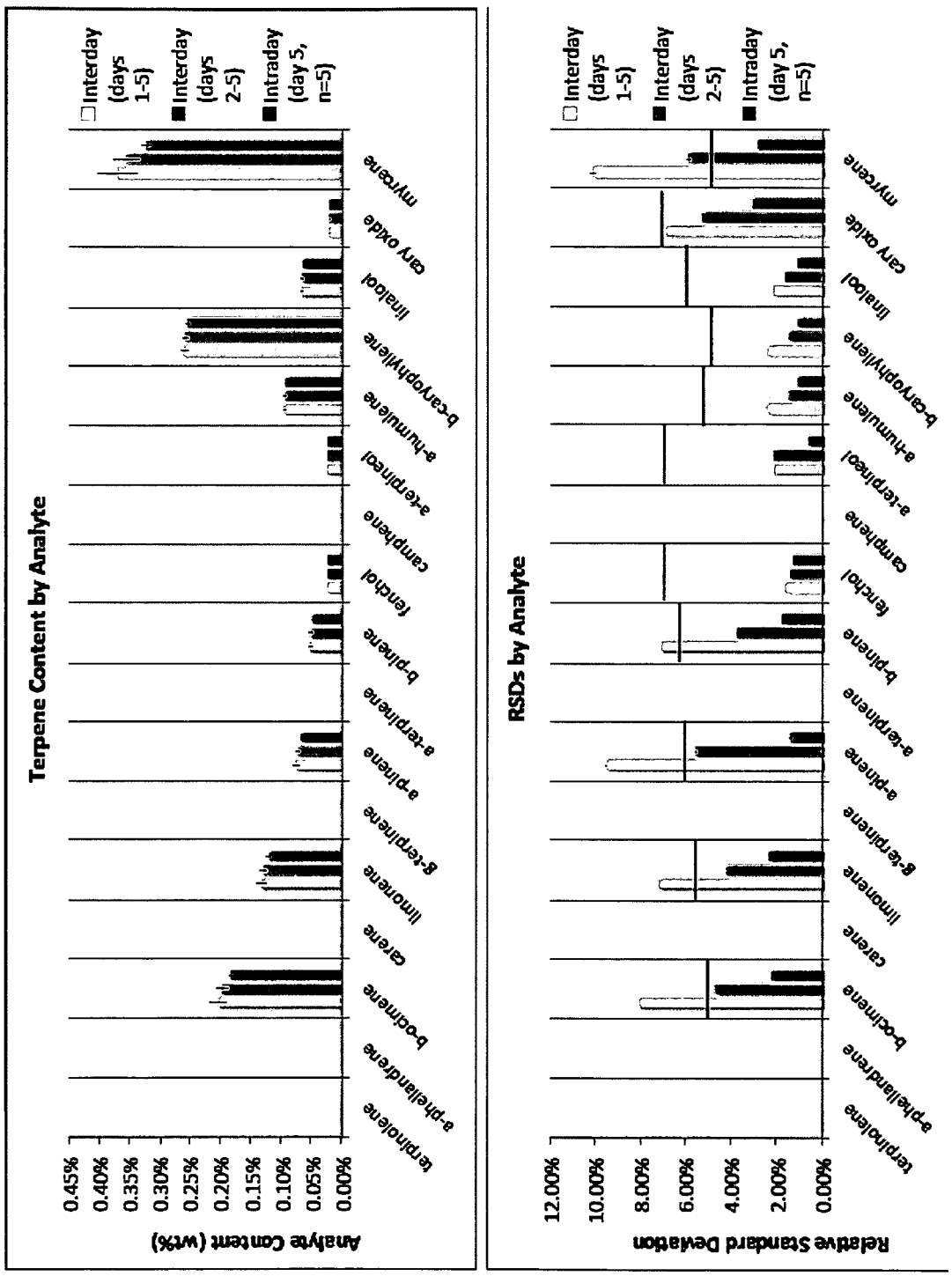
Figure 19A:
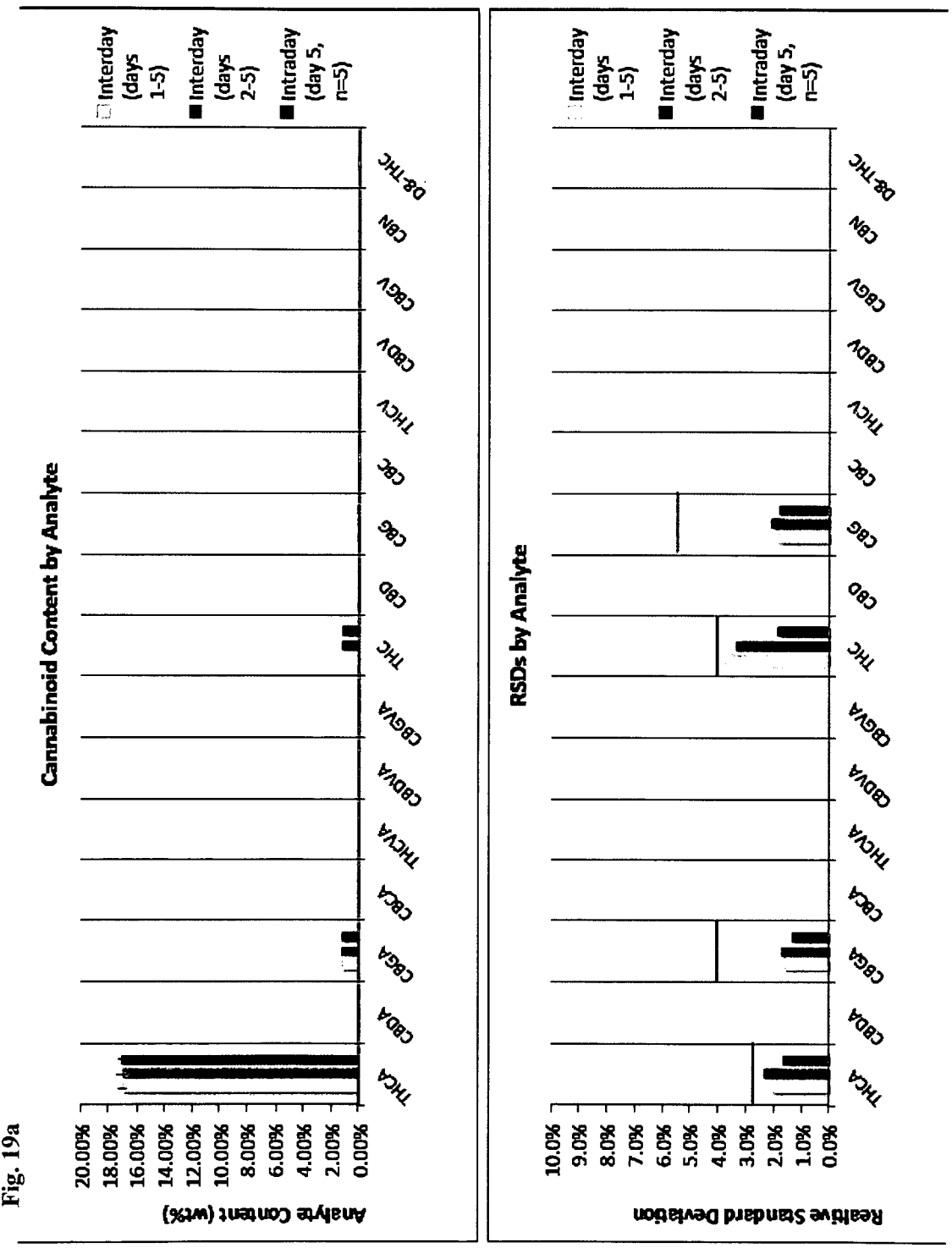
FIG. 19—Intra-day and Inter-day analyte content and precision for Classic Trainwreck variety. (A)—Inter-day and intra-day cannabinoid content. (B)-Inter-day and intra-day terpene content. The PRSDs for each analyte at the determined concentrations are also indicated on the chart by red lines.
Figure 19B:
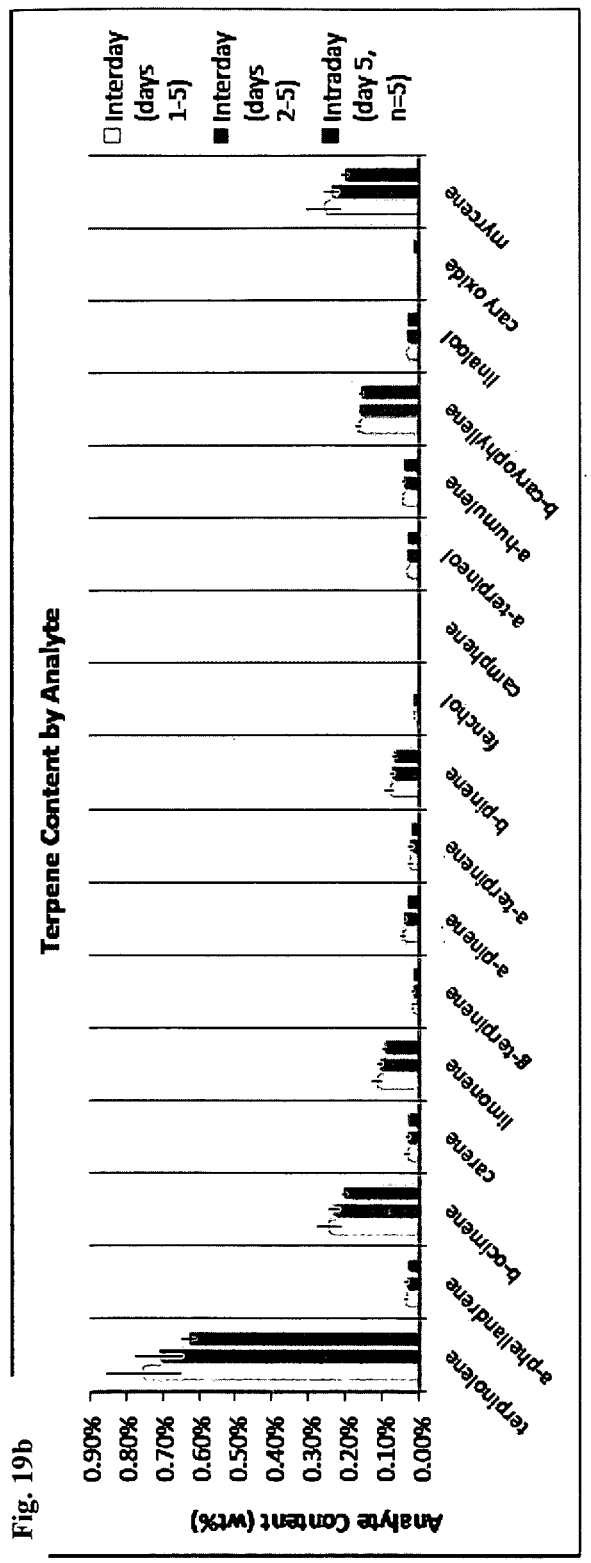
Figure 19B:
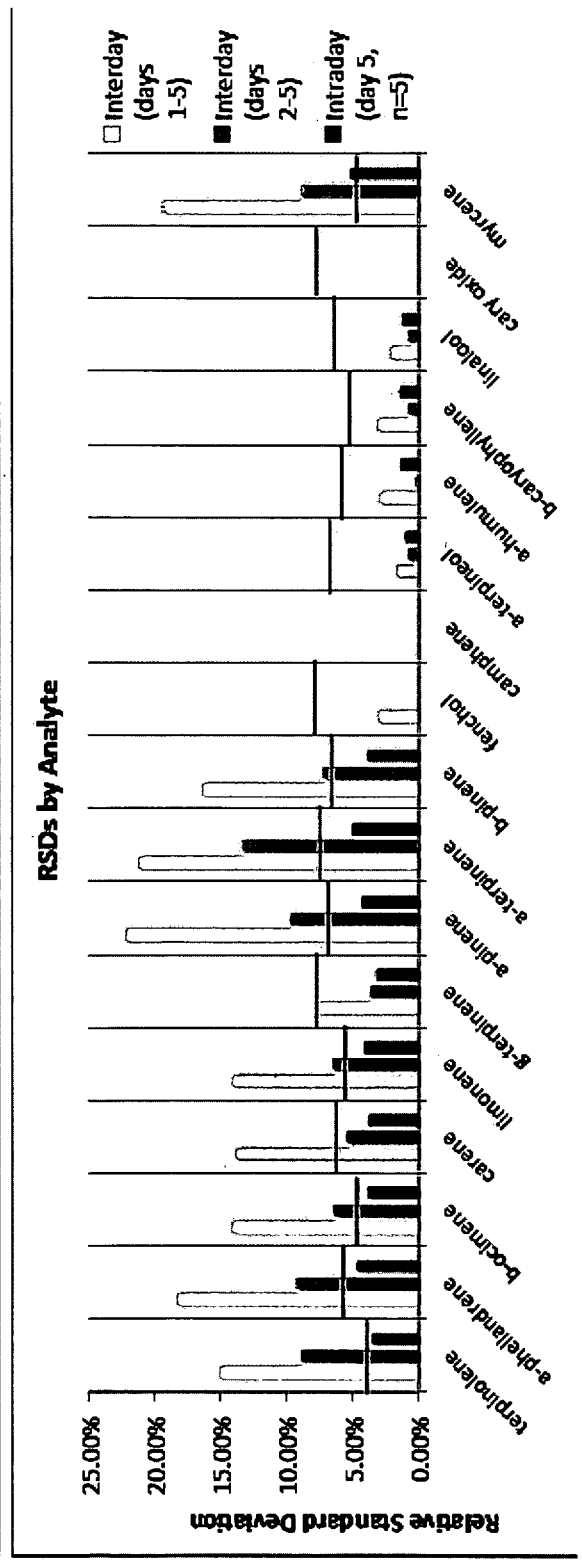
Figure 20A:
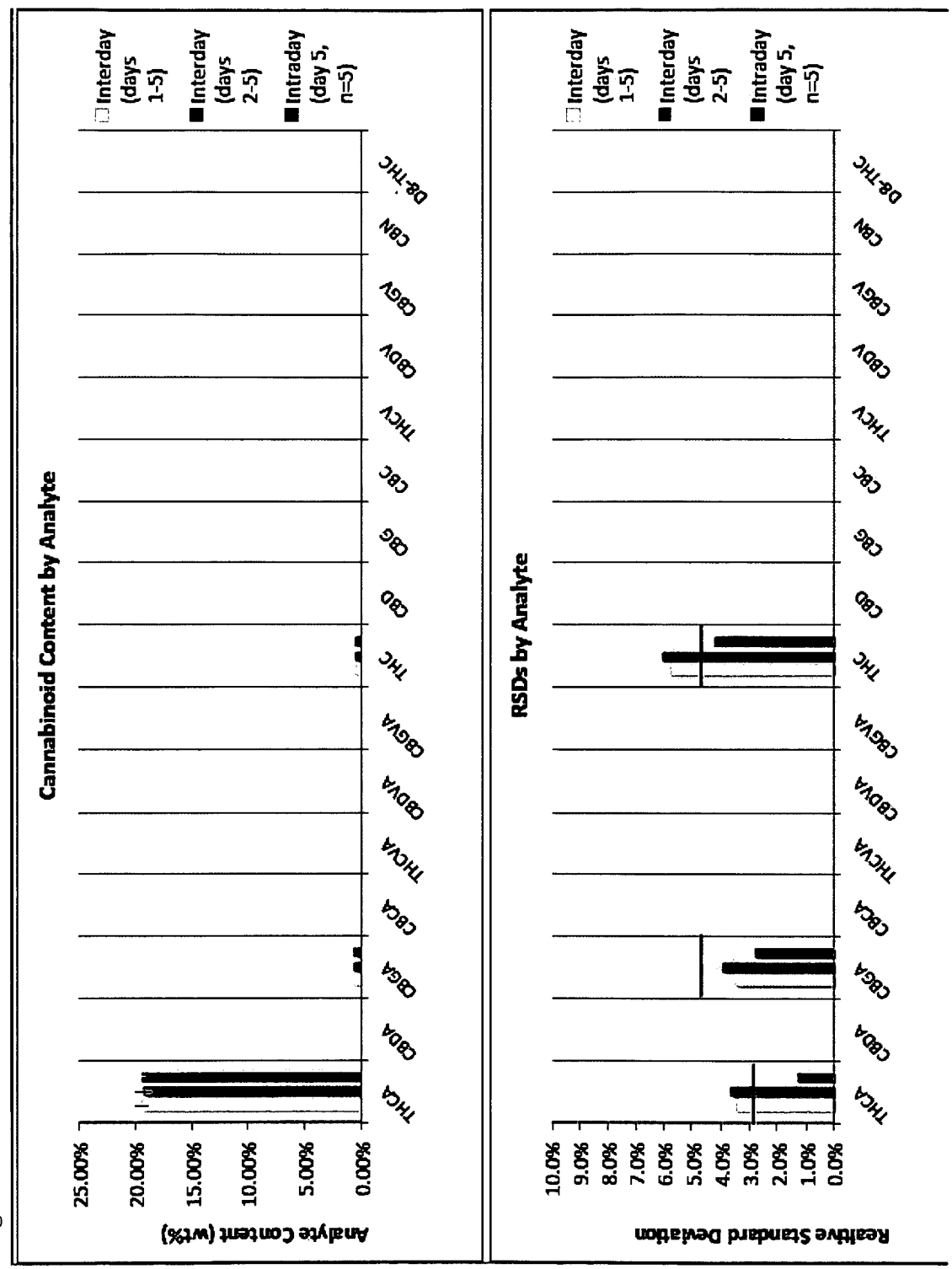
FIG. 20—Intra-day and Inter-day analyte content and precision for Master Kush variety. (A)—Inter-day and intra-day cannabinoid content. (B)-Inter-day and intra-day terpene content. The PRSDs for each analyte at the determined concentrations are also indicated on the chart by red lines.
Figure 20B:
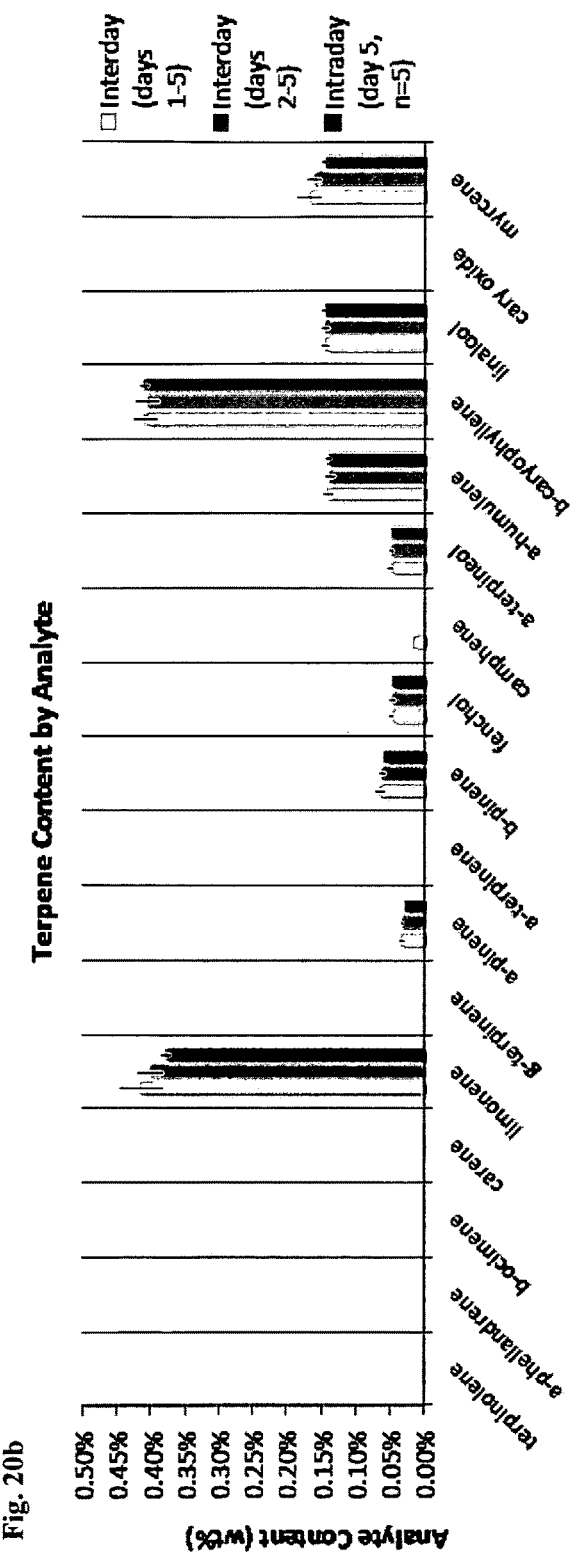
Figure 20B:
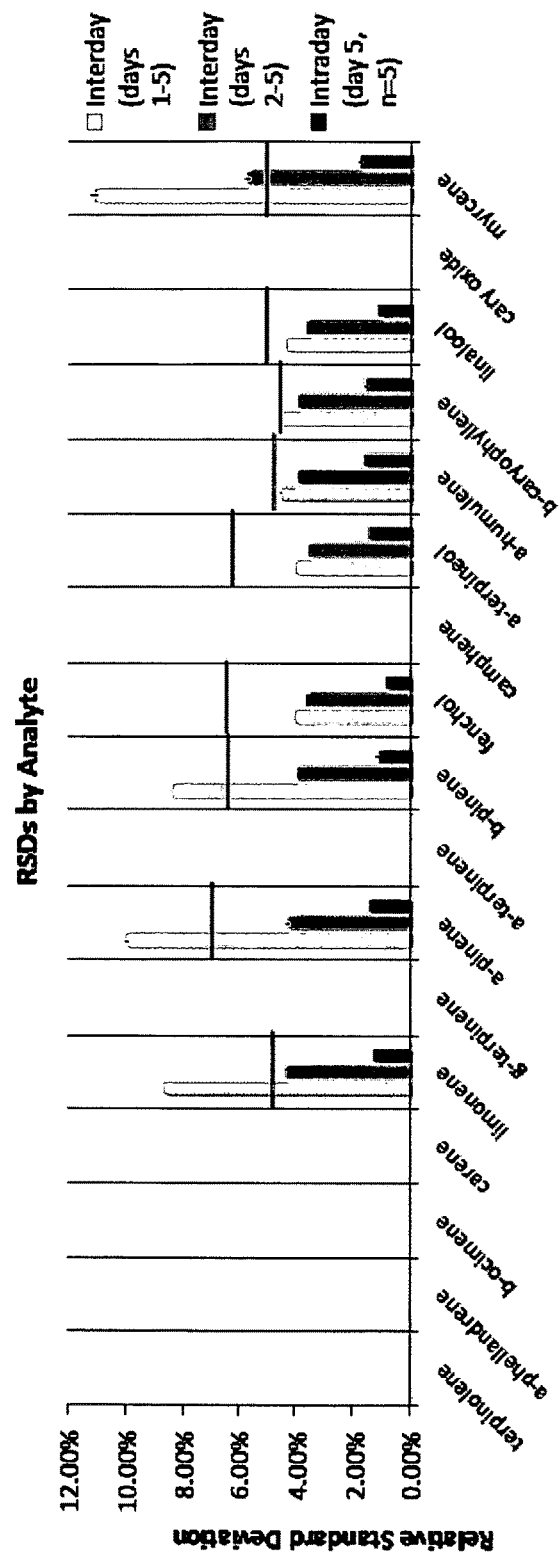
Figure 21A:
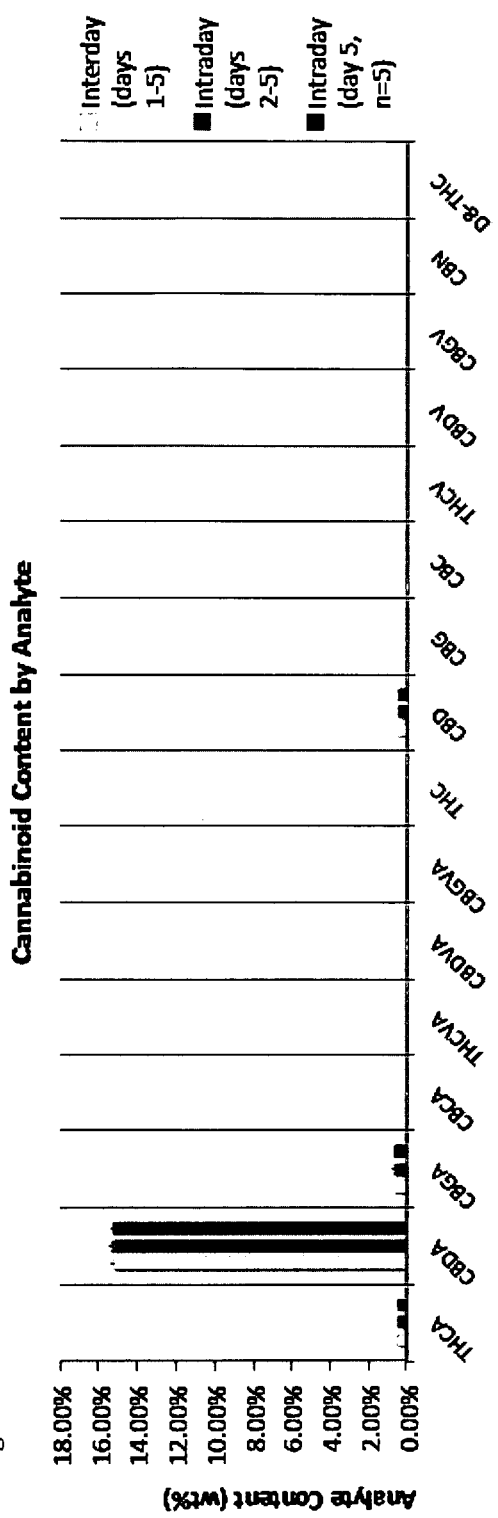
FIG. 21—Intra-day and Inter-day analyte content and precision for ACDC variety. (A)-Inter-day and intra-day cannabinoid content. (B)-Inter-day and intra-day terpene content. The PRSDs for each analyte at the determined concentrations are also indicated on the chart by red lines.
Figure 21A:
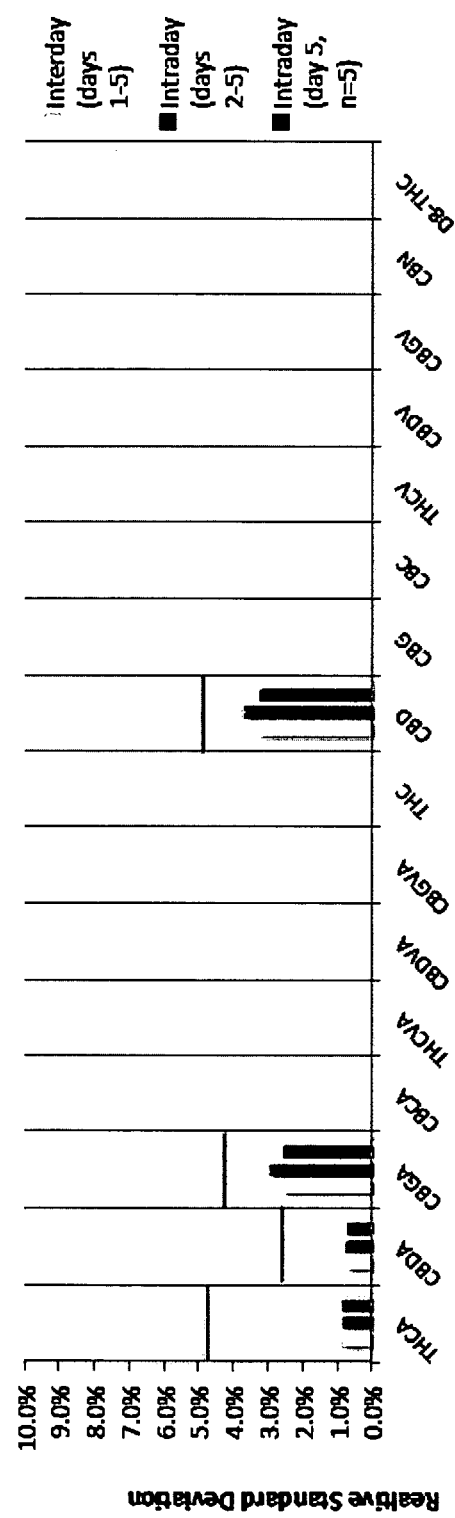
Figure 21B:
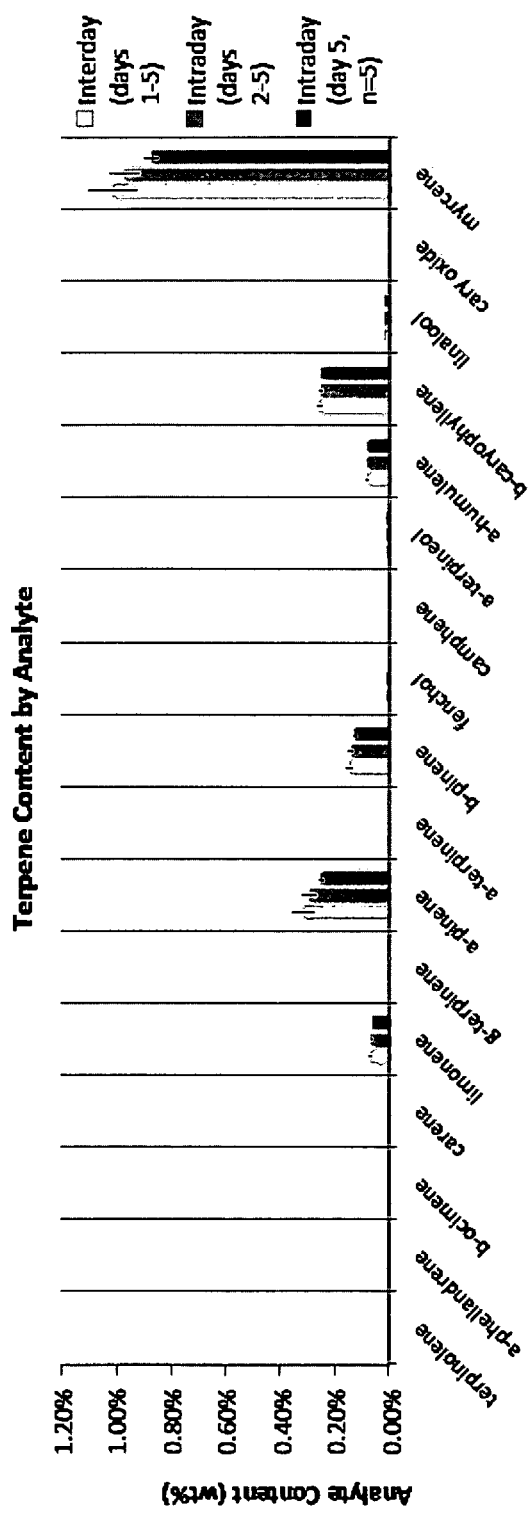
Figure 21B:
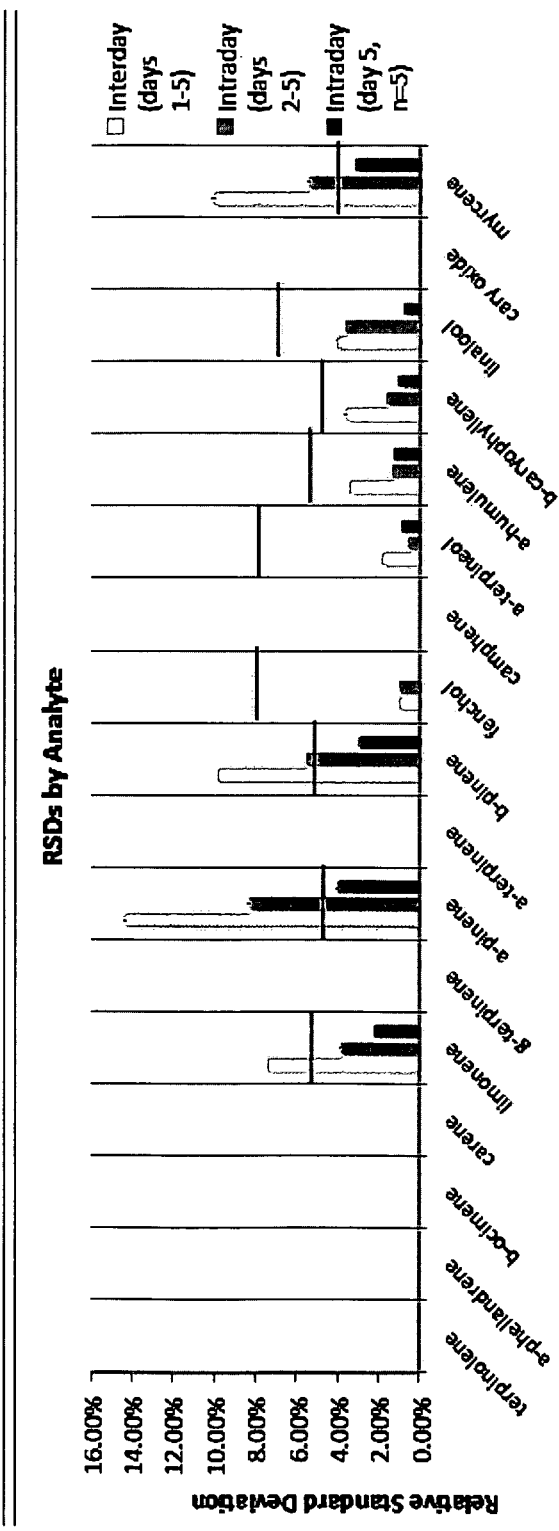
Figure 22A:
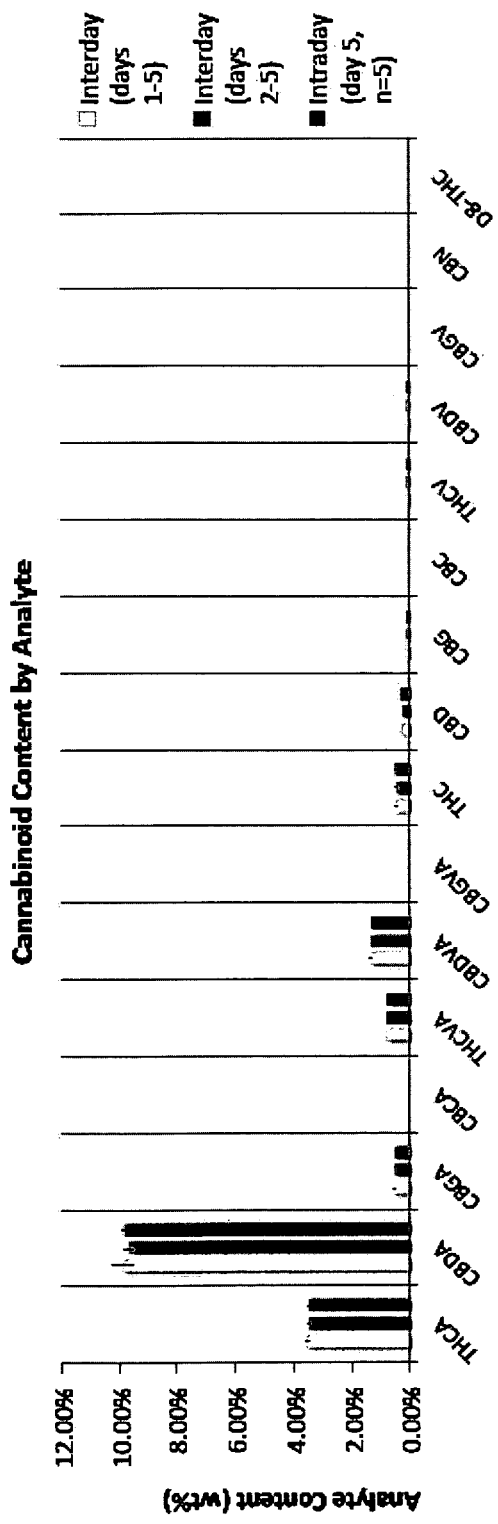
FIG. 22—Intra-day and Inter-day analyte content and precision for Proprietary Hybrid variety. (A)—Inter-day and intra-day cannabinoid content. (B)-Inter-day and intra-day terpene content. The PRSDs for each analyte at the determined concentrations are also indicated on the chart by red lines.
Figure 22A:
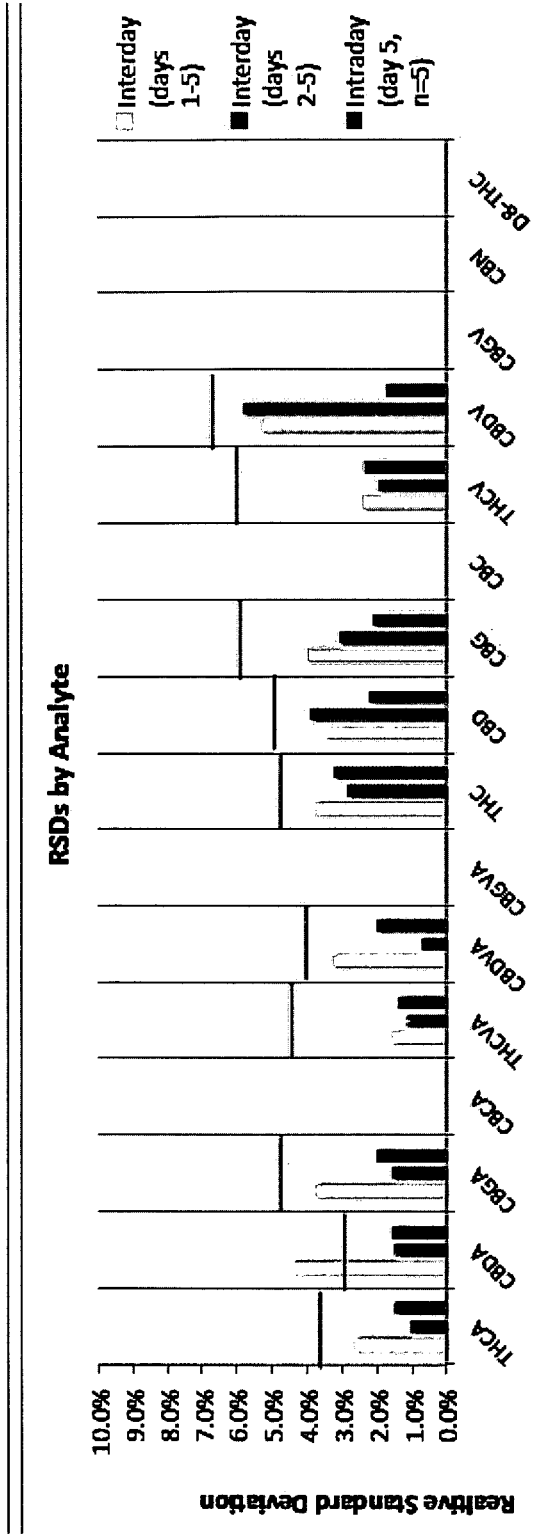
Figure 22B:
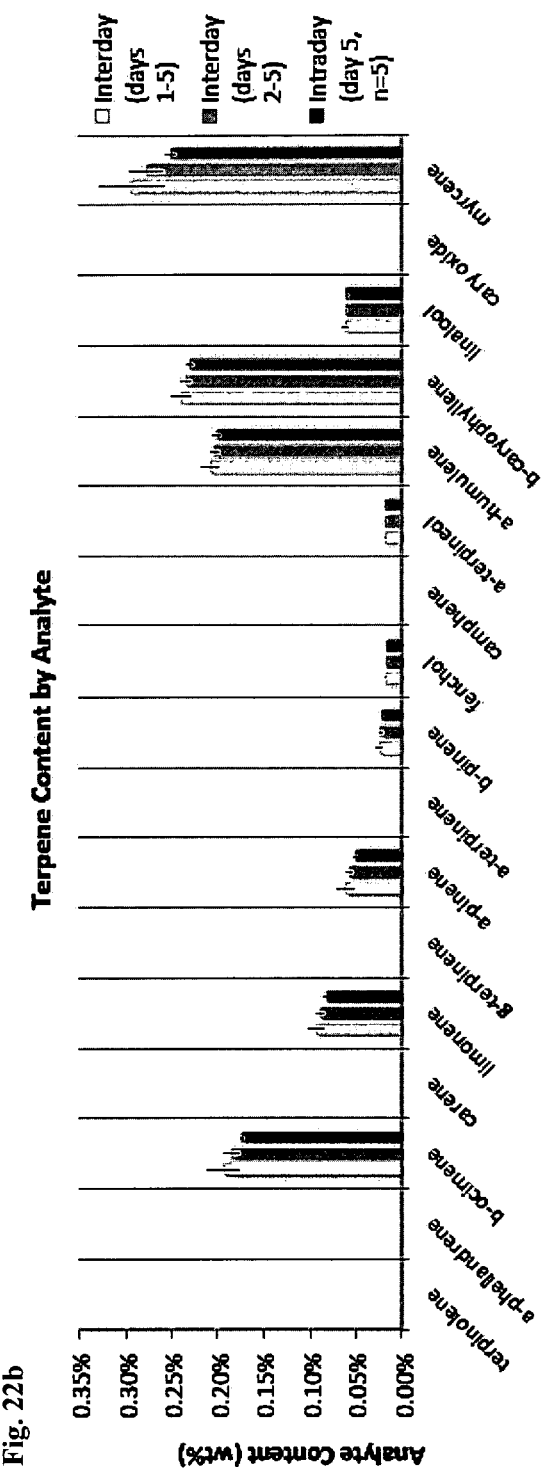
Figure 22B:
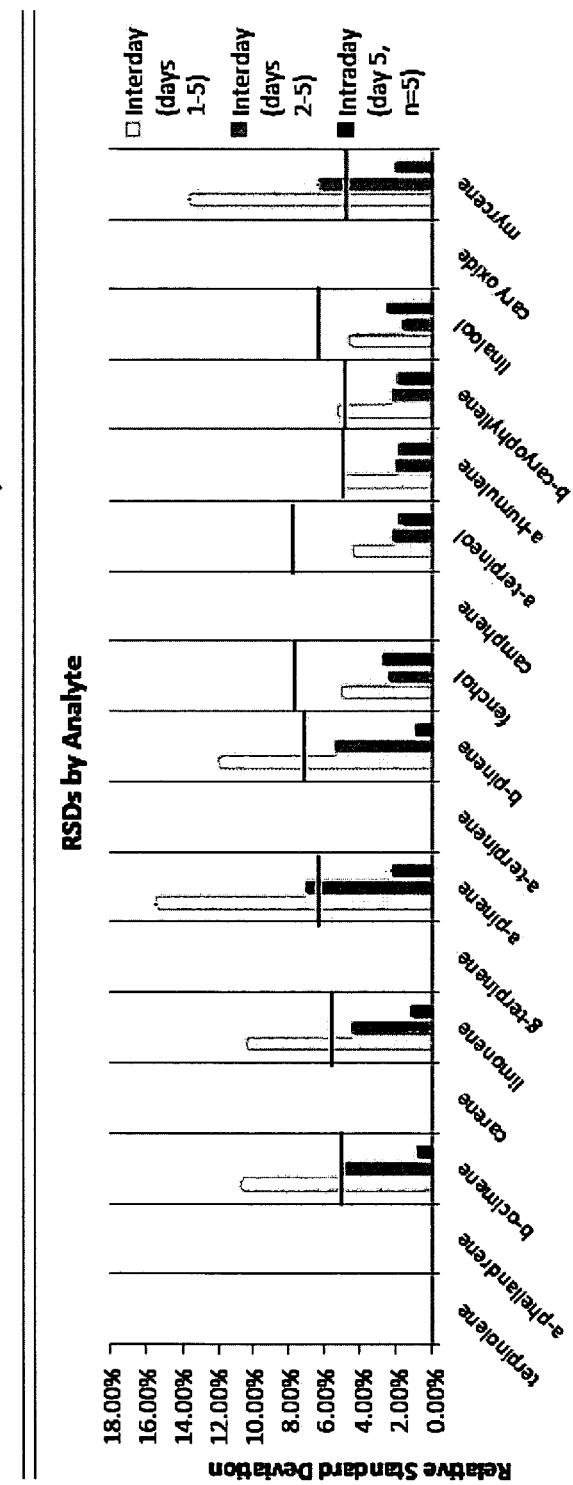

The charts in FIG. 17 show the precision and spike recovery error (along with 95% confidence intervals) for each of the cannabinoids at low, medium, and high concentrations (n=5). The red lines on the charts indicate the accepted PRSDs and errors in recovery at the respective orders of magnitude (14). The precision was acceptable for all the cannabinoids except for THCA at the low concentration range. This was undoubtedly due to the variable residual amounts of THCA present in the blank matrix (see Table 6). Note CBGA also exhibited a higher RSD and this analyte was also present in the blank matrix at a higher level. In terms of spike recovery error, 20 of the 24 points exhibited acceptable recoveries, while the others were only slightly over the limits but still acceptable for such a diverse assay. The larger error seen with THCV at the high 19% level was most likely due to the fact that this extract contained an even larger amount of CBD, which overloaded the column and resulted in some loss of baseline resolution of those two analytes (see chromatogram in FIG. 3).

Example 13—Precision

Instrumental precision was determined by injecting each calibration level in triplicate over different days. This was shown in FIGS. 2, 4 and 5 and the RSDs for the both the cannabinoids and the terpenes were generally less than 2%.

A robust assay should be applicable to a wide range of cultivars and analytes, and give similar precision and recovery when performed multiple times on one day and over different days. Both intra-day and inter-day precisions for the entire extraction and analysis process were determined by extracting five cultivars (Pincher's Creek, Classic Trainwreck, ACDC, Proprietary Hybrid, and Master Kush) five times over the course of five days, and five times on a single day. These cultivars were chosen to obtain a broad representation of analyte profiles and flower morphologies. In order to start with a homogeneous sample, a 20 g sample of flowers was homogenized on the first day for extraction and the remainder of the ground flower was stored at −20° C. in between extractions. The inter-day analyses were carried out on days 1-5, while the intra-day analyses were all carried out on day five (n=5).

FIGS. 18-22 show the concentrations of the individual cannabinoids and terpenes in the samples along with the RSDs. The PRSDs for each analyte at the determined concentrations are also indicated on the chart by red lines. As a general rule, both inter-day and intra-day precisions of the cannabinoid assay were well within accepted limits for all analytes and were generally less than 2%. It is also seen that intra-day precision is generally slightly better than inter-day precision. The most notable deviations were seen with CBDA in the THV Hybrid and THCA/THC in Master Kush. The outliers found in Master Kush are most likely related to sample morphology, as this flower was the most "difficult" to handle. It was very dense, sticky, had a larger proportion of stem material, and was difficult to homogenize and sample.

Approximately half of the terpenes failed to meet acceptable inter-day precision limits while they passed intra-day precision criteria. This was a consequence of our sampling methodology, where large amounts of flowers were pre-ground and stored at −20° C. to ensure a more homogenous sample for testing over the course of the study. After grinding there is a rapid decrease of the more volatile monoterpenes once flowers are homogenized in a grinder and the trichomes are ruptured. This loss occurs even when stored at −20° C. This decrease is most significant on day one after the initial homogenization, and this can be seen in FIGS. 18-22. The inter-day (days 1-5) results contain day one so the absolute values are the highest as are the RSDs since the decrease is the greatest. The inter-day (days 2-5) results are the same results with day one removed from the analysis, and the absolute values are slightly lower due to analyte loss, but the RSDs are also lower since the rate of loss slows. The final intra-day (day 5, n=5) results were all acquired on day five so the absolute values are the lowest, but so are the RSDs since all the extractions were performed on the same day. Note the cannabinoids and less volatile terpeneols and sesquiterpenes had comparable results for both intra-day and inter-day analyses. This strongly suggests that once large sample sizes are homogenized they must be extracted the same day to obtain representative assay results for the monoterpenes.

In general, this terpene assay provides intra-day precisions of less than 2% for all major analytes. Presumably the inter-day precisions would also satisfy requirements if fresh flowers were used for every analysis, and this can even be seen for most analytes if Day 1 is eliminated from the analysis.

Example 14—Plant Variability

In order to better understand the variability associated with medical cannabis production, a state-of-the-art production facility was subjected to extensive sampling and chemotype analyses. All plants were genetically identical, at the same stage of development, planted in the same potting mix, situated together on one table, and all watering, fertilizing, and other routine maintenance had been performed in the same manner for all of the test subjects. One third of the total population was randomly chosen across the growing area for sampling. Samples of flowers were taken from each plant at three vertical locations within the plant canopy. The samples were allowed to dry to approximately 10% moisture at ambient temperature, and then trimmed to mimic medical cannabis flowers. Flowers were stored at −20° C. in sealed plastic containers until analyses.

Figure 23:
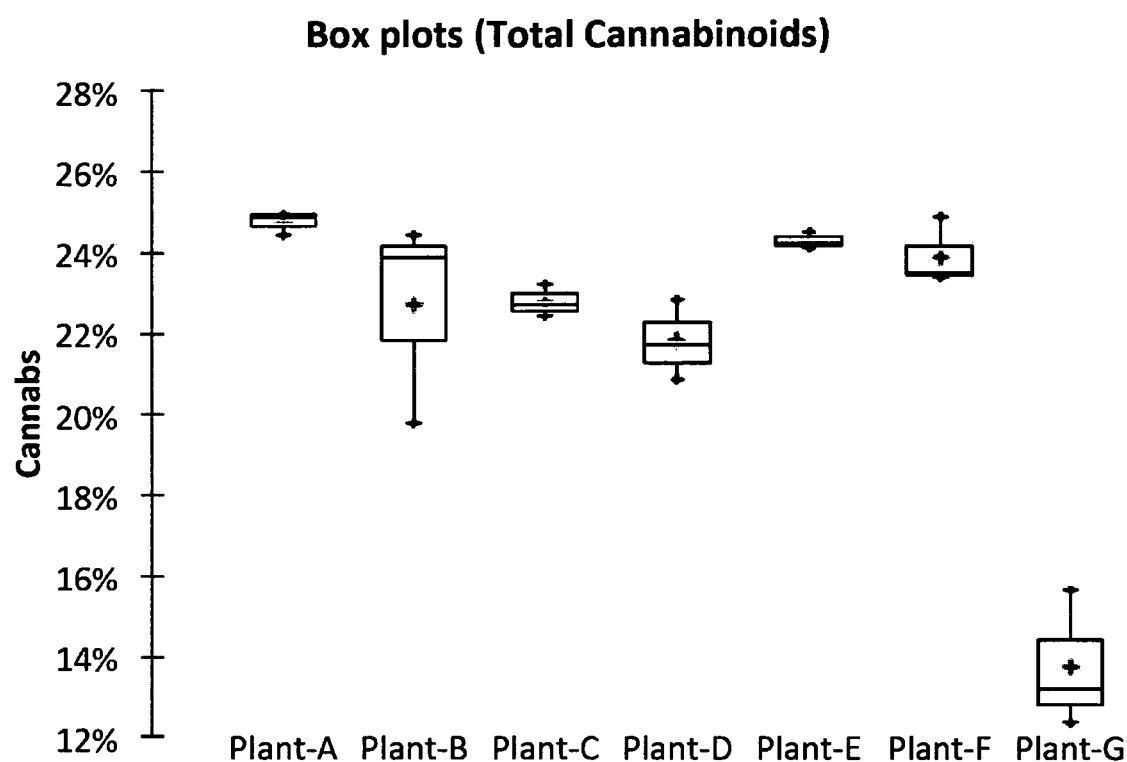
FIG. 23—Cannabinoid content from plants sampled at high, medium, and low positions within the canopy. Comparison between box plots for plants A-G shows measured inter-plant variability. Comparison of box plots within each plant shows intra-plant variability.

The total cannabinoids in the flowers ranged from 12.4-25.0% (w/w) of the dried plant material. FIG. 23 shows a boxplot of total cannabinoid content of each plant that was sampled, with three samples per plant at high, medium, and low heights within the canopy. Generally speaking the intra-plant variability of total cannabinoids is much lower than the inter-plant variability, however this does not hold true for every individual as plant B and G both show significantly higher variation than the others.

Figure 24:
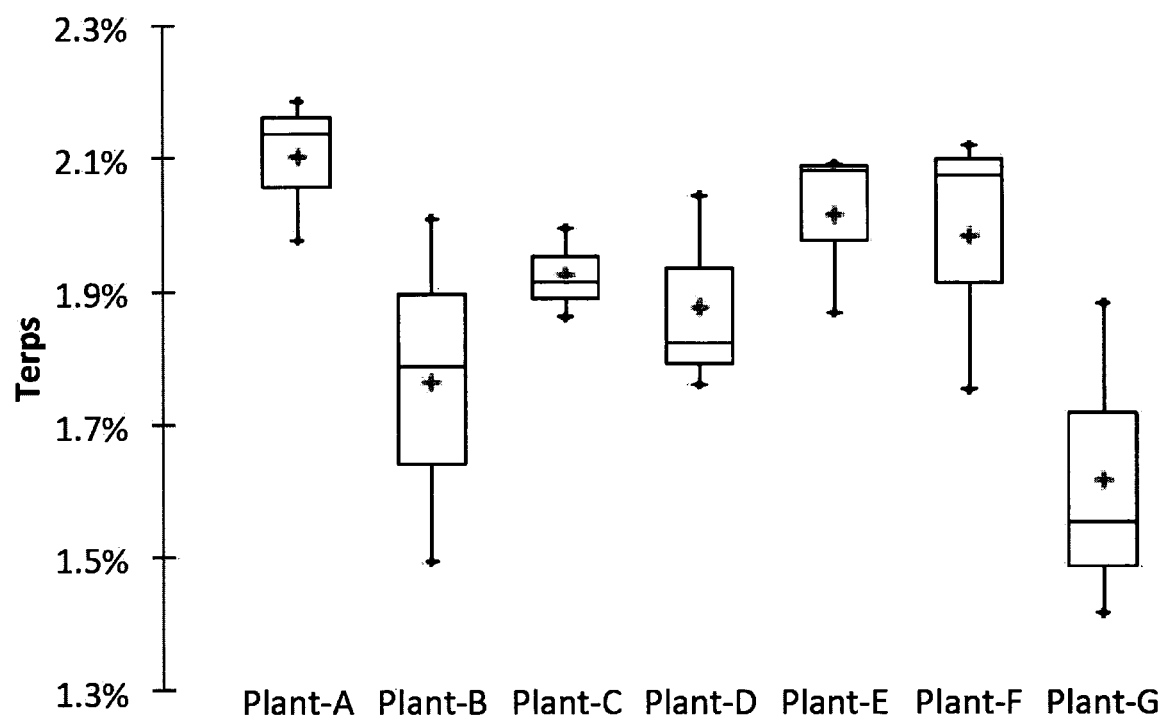
FIG. 24—Terpene content from plants sampled at high, medium, and low positions within the canopy. Comparison between box plots for plants A-G shows measured inter-plant variability. Comparison of box plots within each plant shows intra-plant variability.

The range of total terpenes in the plants was 1.42-2.19% (w/w). FIG. 24 shows a boxplot of the total terpene content by plant. The intra-plant and inter-plant variability of total terpene content are of similar orders of magnitude, however plants B and G still stand out as having more variation than the other individuals.

Figure 25:
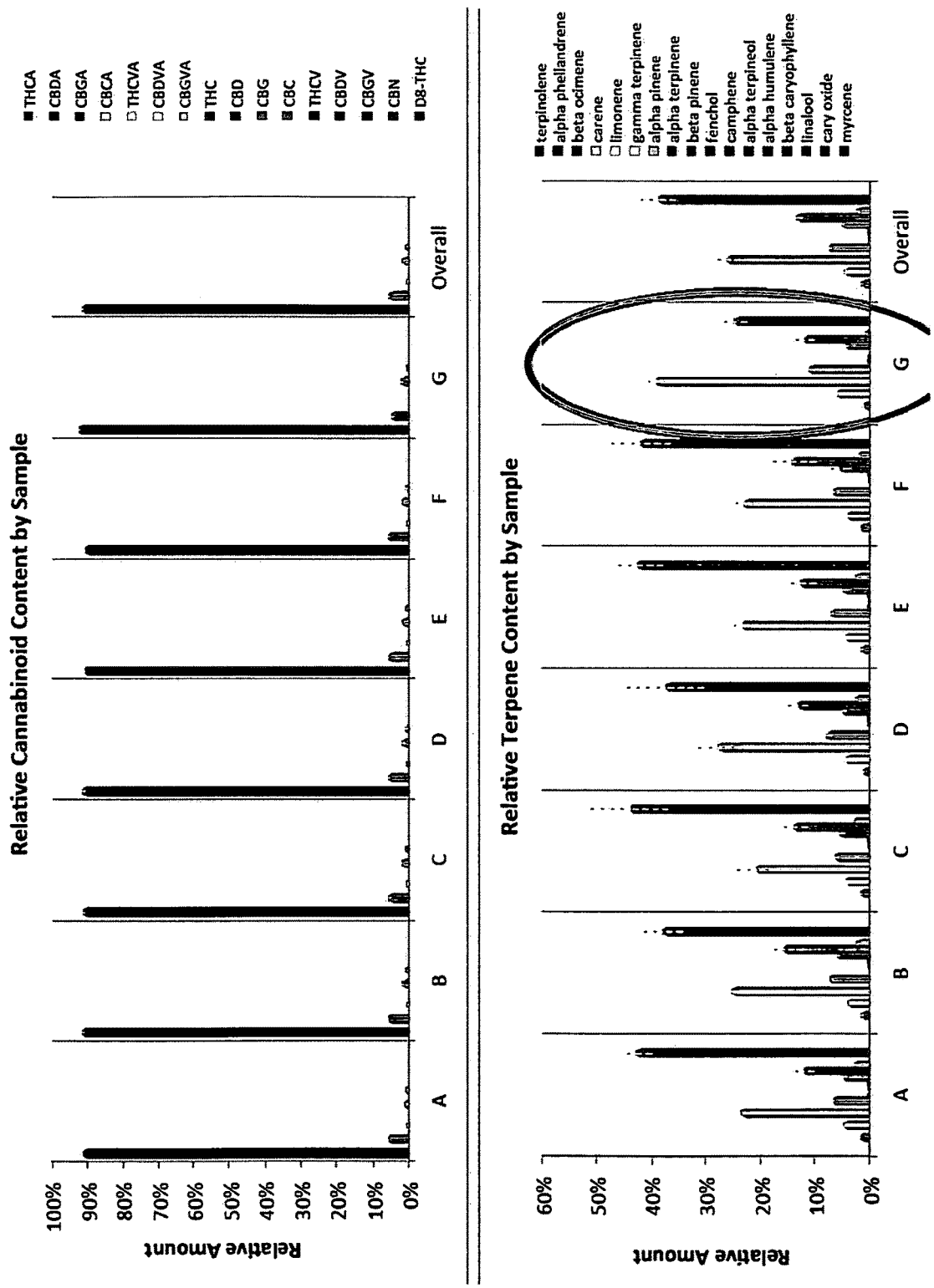
FIG. 25—Relative analyte content of the seven plants sampled.

Variability is inherent in agricultural crops and not due to any special causes, however in this case a detailed analysis suggested plant G was indeed an outlier. The relative content of the individual terpenes is shown as a bar chart in FIG. 25. The last terpene profile, labeled 'overall', contains the average for all relative amounts of terpenes in every plant. Error bars represent a 95% confidence interval. The dominant terpene in most of the plants is myrcene, while plant G is indeed set apart as a different chemotype altogether, with alpha-pinene as its dominant terpene. The source of this remains unclear but can most likely be attributed to a mislabeled plant with similar phenotypic characteristics.

These results demonstrate the potential for differences in secondary metabolite levels in plants with identical genetic background, grown in the same environment, and handled with the same care and maintenance. Understanding plant variability is critical when obtaining a "representative" sample of flowers that will be used to determine the content of pharmacologically active compounds. In this case, if only one or two flowers had been sampled from the table and plant G had been included an erroneous chemotype and potency for that lot would have been reported, even from a lab using validated methodology. The potency of plant G with respect to THCA was about half that of the other plants, so labs testing different flowers from this lot would have obtained different results and this could conceivably have led to difficulties with patients attempting to self-titrate their dosage. In addition, if patients wanted the effects of myrcene (sedative, antinociceptive (18, 19)) and unexpectedly got alpha-pinene (stimulant, bronchodilator, anti-inflammatory (20)) this may have caused some discomfort and concern.

While "outliers" may be rare, even testing only one or two flowers from normal population distributions can give quite different results for absolute content. A completely random sample and a large sample mass are both critical to obtaining representative analytical results for any given lot of medical cannabis. Skilled cultivators and plant scientists are also essential for preventing and/or recognizing outliers, such as plant G, in the plant population prior to reaching the patient.

Example 15—Comparison with Other Analyses

While cultivation may contribute to the variability of test results, the analytical lab itself can be another contributing factor. A number of samples were obtained from dispensaries and analyzed both in house and sent out for testing by other laboratories in California. The results ranged from minor differences in absolute analyte levels to complete misidentification of analytes. Given the variability inherent in this crop, as discussed above, this section focuses on the latter cases, which are more difficult to attribute to plant variability.

Unlike flowers, extracts are homogeneous and it is not unreasonable to expect similar results from different laboratories. Table 7 shows the analytical results obtained for an extract tested in-house using the methods of the present invention compared to the results from the same samples from different laboratory for analysis. While the outsourced testing provided slightly lower values for both THCA and THC the most interesting result is the lack of any CBGA and the presence of CBDA, which contrasts with our findings and the common observation that typical Chemotype I cultivars contain CBGA (the precursor to THCA) and no CBDA. Presumably, due to the very close retention times of CBGA and CBDA in many assays, CBGA has been misidentified as CBDA by this testing facility. The results of the terpene analyses by the two labs are also shown in Table 7. A number of the results such as limonene, linalool, and humulene are quite close, however there are substantial errors with both myrcene and caryophyllene and these are two of the more commonly occurring terpenes in cannabis.

TABLE 7

Analytical results for an extracted tested in-house and sent to an external lab.

| Analyte | In-house (Wt %) | External Lab A (Wt %) |
| --- | --- | --- |
| THCA | 26.0 | 20.4 |
| THC | 25.7 | 71.1 |
| CBGA | 2.4 | ND |
| CBN | 0.5 | 0.6 |
| CBDA | 0.3 | 1.1 |
| CBD | 0.1 | 0.1 |
| terpinolene | 0.02 | NT |
| α-phellandrene | ND | ND |
| β-ocimene | 0.07 | NT |
| Δ3-carene | ND | ND |
| limonene | 0.46 | 0.42 |
| γ-terpinene | ND | NT |
| α-pinene | 0.10 | 0.09 |
| α-terpinene | ND | ND |
| β-pinene | 0.10 | NT |
| fenchol | 0.25 | 0.22 |
| camphene | 0.02 | NT |
| α-terpineol | ND | 0.22 |
| α-humulene | 0.85 | 0.72 |
| β-caryophyllene | 2.26 | 0.40 |
| linalool | 0.37 | 0.33 |
| caryophyllene oxide | ND | 0.31 |
| myrcene | 0.40 | 0.09 |

Table 8 shows the terpene profiles of three flowers from different cultivars that were divided and tested in-house and sent to a different California testing facility.

TABLE 8

Comparison of terpene profiles in three different samples.

| | Cultivar | | | | | |
|---|---|---|---|---|---|---|
| | Purple Trainwreck | | Kryptonic | | OG Legend | |
| Lab | In-house (Wt %) | External Lab B (Wt %) | In-house (Wt %) | External Lab B (Wt %) | In-house (Wt %) | External Lab B (Wt %) |
| terpinolene | 0.781 | 0.08 | 0.055 | 0.08 | ND | 0.16 |
| alpha-phellandrene | 0.039 | | ND | | ND | |
| beta-ocimene | 0.342 | | 0.055 | | ND | |
| delta3-carene | 0.031 | | ND | | ND | |
| limonene | 0.174 | 1.3 | 0.628 | 0.36 | 0.529 | 0.35 |
| gamma-terpinene | ND | | ND | | ND | |
| alpha-pinene | 0.075 | 0.03 | 0.073 | 0.56 | 0.051 | 0.50 |
| alpha-terpinene | 0.029 | | ND | | ND | |
| beta-pinene | 0.110 | | 0.103 | | 0.106 | |
| fenchol | 0.027 | | 0.05 | | 0.068 | |
| camphene | ND | | 0.016 | | 0.017 | |
| alpha-terpineol | 0.049 | | 0.076 | | 0.07 | |
| alpha-humulene | 0.038 | | 0.144 | | 0.067 | |
| beta-caryophyllene | 0.147 | ND | 0.595 | 0.85 | 0.234 | 0.13 |
| linalool | 0.065 | 0.09 | 0.052 | 0.11 | 0.271 | 0.51 |
| caryophyllene oxide | ND | ND | ND | 0.03 | ND | ND |
| myrcene | 0.25 | 0.42 | 0.124 | 0.35 | 0.38 | 0.30 |

The first example is a cultivar designated Purple Trainwreck. Terpinolene is the defining terpene of the Trainwreck class of cultivars, yet it was conspicuously absent in the out-sourced test results. Similarly, Kryptonic is typically defined by a limonene and caryophyllene dominant terpene profile with very small amounts of pinene and myrcene, yet the test results from the other facility indicated a pinene and caryophyllene dominant profile. OG Legend is another limonene dominant cultivar followed by caryophyllene, linalool, and myrcene at similar concentrations. However, the outsourced testing indicated linalool and pinene dominance. These examples were chosen because although changes in absolute concentrations may be seen due to handling, these types of large-scale changes in the relative profiles are not observed if the sample is treated properly. Admittedly, the samples may have been mixed up during the "intake" process and this may be an issue with the laboratories inventory management and reporting structure and not the assays, but the end result of inaccurate reporting is still problematic.

Figure 26:
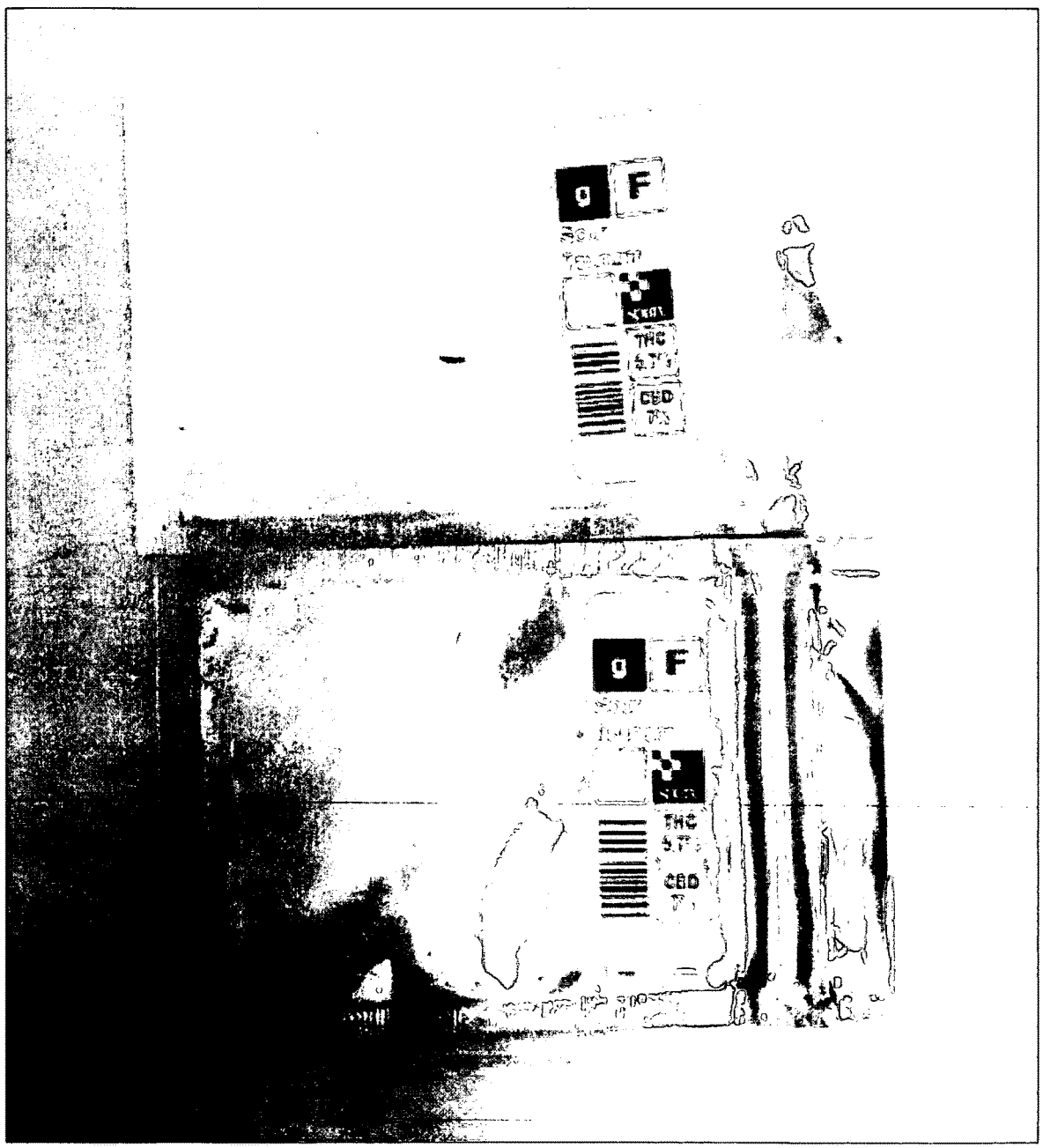
FIG. 26—Dispensary labels of chemotype I THC-producing flowers labeled as chemotype II flowers (THC-CBD) producing flowers. Sample mislabeling is common among U.S. dispensaries and analytical services.

The final example is arguably the most egregious of the offenses. The photo in FIG. 26 shows two samples of "Sour Tsunami" purchased from a local dispensary. Sour Tsunami is reported to be a Chemotype 11 cultivar with a mixture of THCA and CBDA, and the label on the packaging clearly states 5.7% THC and 7% CBD. Our analysis of this sample indicated it was a Chemotype I cultivar with only 18% THCA present. It is not known at what point in the process between cultivation, testing, packaging, and labeling this error occurred but it is a potentially dangerous mistake.

Example 16—Chemical Desiccation of Samples

Cannabis samples designated for cannabinoid and terpene analysis were chemically desiccated. Samples were placed in either a lidded plastic storage container 665.5 cm$^3$ (samples #3-8) or screw top glass jars 752.3 cm$^3$ (samples 1-2) (Table 9). Wet flowers were harvested and were immediately placed under a watch glass until harvest of the plant was complete. The fresh weight of each sample was measured and recorded while on a plate. Weight of each plate was also separately measured. The samples and plates were then placed inside their respective container as described above.

Various amounts of DampRid® were tested in teach sample as shown in Table 9 below to test ratios of desiccant that could dry the flowers within 72 hours. After 96 hours, samples were placed in an oven and were heated.

TABLE 9

Chemical desiccation of cannabis samples.

| Plate # | Ratio of Damp-Rid:Flower | Container type | Plate mass (g) | Plate + Flwr (g) | Wet Flwr (g) | Target Damp-Rid mass(g) | Actual Damp-Rid mass (g) | Mass (g) after 24 h time | Mass (g) after 48 h time | Mass (g) after 72 h time | Mass (g) after 96 h time | Final mass after oven dry (g) |
|---|---|---|---|---|---|---|---|---|---|---|---|---|
| 1 | 10:1 | glass | 18.434 | 21.89 | 3.456 | 34.6 | 34.52 | 20.188 | | 19.225 | 19.209 | 19.165 |
| 2 | 20:1 | glass | 18.241 | 21.161 | 2.92 | 58.4 | 58.58 | 19.586 | | 18.895 | 18.889 | 18.827 |
| 3 | 30:1 | tupper | 18.545 | 22.285 | 3.74 | 112.2 | 112.4 | 20.112 | | 19.383 | 19.377 | 19.339 |
| 4 | 40:1 | tupper | 18.464 | 21.285 | 2.821 | 112.8 | 112.9 | 19.693 | | 19.076 | 19.071 | 19.041 |
| 5 | 50:1 | tupper | 18.309 | 22.572 | 4.263 | 213.2 | 213.000 | 20.113 | | 19.221 | 19.213 | 19.178 |
| 6 | 10:1 | tupper | 18.418 | 20.593 | 2.175 | 21.75 | 22.1 | 19.495 | 18.981 | 18.888 | 18.88 | |
| 7 | 20:1 | tupper | 18.244 | 20.981 | 2.737 | 54.74 | 54.9 | 19.749 | 19.045 | 18.862 | 18.839 | |
| 8 | 30:1 | tupper | 18.362 | 21.309 | 2.947 | 88.41 | 89.1 | 19.747 | 19.107 | 19.000 | 18.99 | |

The results of this experiment showed that 72 hours was sufficient to reach a steady state moisture level for the samples tested. While the period between 24 and 72 hour resulted in an average of 40-50% mass loss due to moisture removal, the period between 72, and 96 hours only saw an average of 2-4% additional mass loss.

Moreover the results showed that ratios of 10:1 of Damp-Rid® $CaCL_2$ desiccant to sample was sufficient to dry the samples.

Example 17—Comparison of Cannabinoid and Terpene Measurement Accuracy for Oven-Dried and Chemically Desiccated Samples The inventors of the present invention suspected that sample drying using ovens, or other heat or forced air processing, was skewing the results of downstream cannabinoid and terpene analysis. Without wishing to be bound to any single theory, the present inventors believed that oven drying resulted in the loss of mass via loss of cannabinoid and terpenes. The ultimate consequence was believed to be that oven-dried analyses of cannabis samples were not representative of the non-analyzed cannabis tissue sold to the consumer at dispensaries (which had not been subjected to the same heat treatment).

In order to test their hypothesis, the inventors compared the moisture content of various cannabis samples as measured by complete chemical desiccation vs oven drying against a "true" moisture content measured by FTIR.

Cannabis samples for 18 different cannabis varieties were obtained for this analysis. These samples had been previously cured for consumption. The process of curing typically involves hanging the harvested inflorescences in a dry environment for 10-30 days. These specific samples were pulled directly from dispensary shelves, and were thus in their "consumer" state.

5 grams of each sample were ground in a coffee grinder to produce a homogenous cannabis tissue powder according to the methods described herein. The ground tissue was separated into three parts for moisture analysis via oven drying, chemical desiccation, and FTIR, 1 gram of from ground sample was separated and dried via standard oven drying procedures. According to procedures recommended in the AHP monograph, 1000 mg of sample is placed in an oven at 105 C for 2 hours. A second gram from the ground sample was separated and dried via the chemical desiccation methods of the present invention as described in Example 16. For this chemical desiccation, samples were placed in a sealed container with a 20:1 mass ratio of DampRid® (calcium chloride) to sample.

The chemical desiccation was considered complete when the mass of each sample reached a steady-state. Typically this is after 96 hours, but in this case the samples were allowed to stand for two weeks. Table 10 below shows the calculated moisture contents of each sample as determined via oven drying and chemical desiccation.

TABLE 10

Estimated moisture content of 18 cannabis samples as determined by oven drying and chemical desiccation.

| Sample Name | Oven | Chemical desiccation. |
|---|---|---|
| A | 13.83% | 6.15% |
| B | 14.90% | 6.61% |
| C | 13.52% | 6.78% |
| D | 12.90% | 6.70% |

TABLE 10-continued

Estimated moisture content of 18 cannabis samples as determined by oven drying and chemical desiccation.

| Sample Name | Oven | Chemical desiccation. |
|---|---|---|
| E | 12.76% | 6.71% |
| F | 13.59% | 7.06% |
| G | 15.18% | 6.56% |
| H | 11.80% | 5.20% |
| I | 10.87% | 5.69% |
| J | 12.84% | 7.26% |
| K | 12.60% | 5.37% |
| L | 11.55% | 5.81% |
| M | 10.63% | 4.86% |
| N | 12.50% | 6.91% |
| O | 21.68% | 6.08% |
| P | 12.15% | 5.59% |
| Q | 12.98% | 6.37% |
| R | 12.72% | 6.87% |

A third portion from the ground sample was analyzed for moisture content by FTIR. The above-calculated moisture contents of each sample from Table 10 were compared against the moisture content values from the FTIR. The values were plotted in a graph and a correlation coefficient for was calculated for the IR moisture values vs the oven and chemical desiccation values. The R2 correlation coefficient for the moisture content of FTIR vs. oven drying was 0.52. The R2 correlation coefficient for the moisture content of FTIR vs. chemical desiccation was 92.2.

These results suggested that chemical desiccation moisture content calculations were more accurate than those obtained via oven-drying procedures. This is also evidence that the additional loss of mass calculated for oven drying samples, included non-moisture losses, including potentially cannabinoids and terpenes.

These results also suggest the possibility that current protocols for sample drying could be replaced by FTIR measurement of moisture content.

Figure 28:
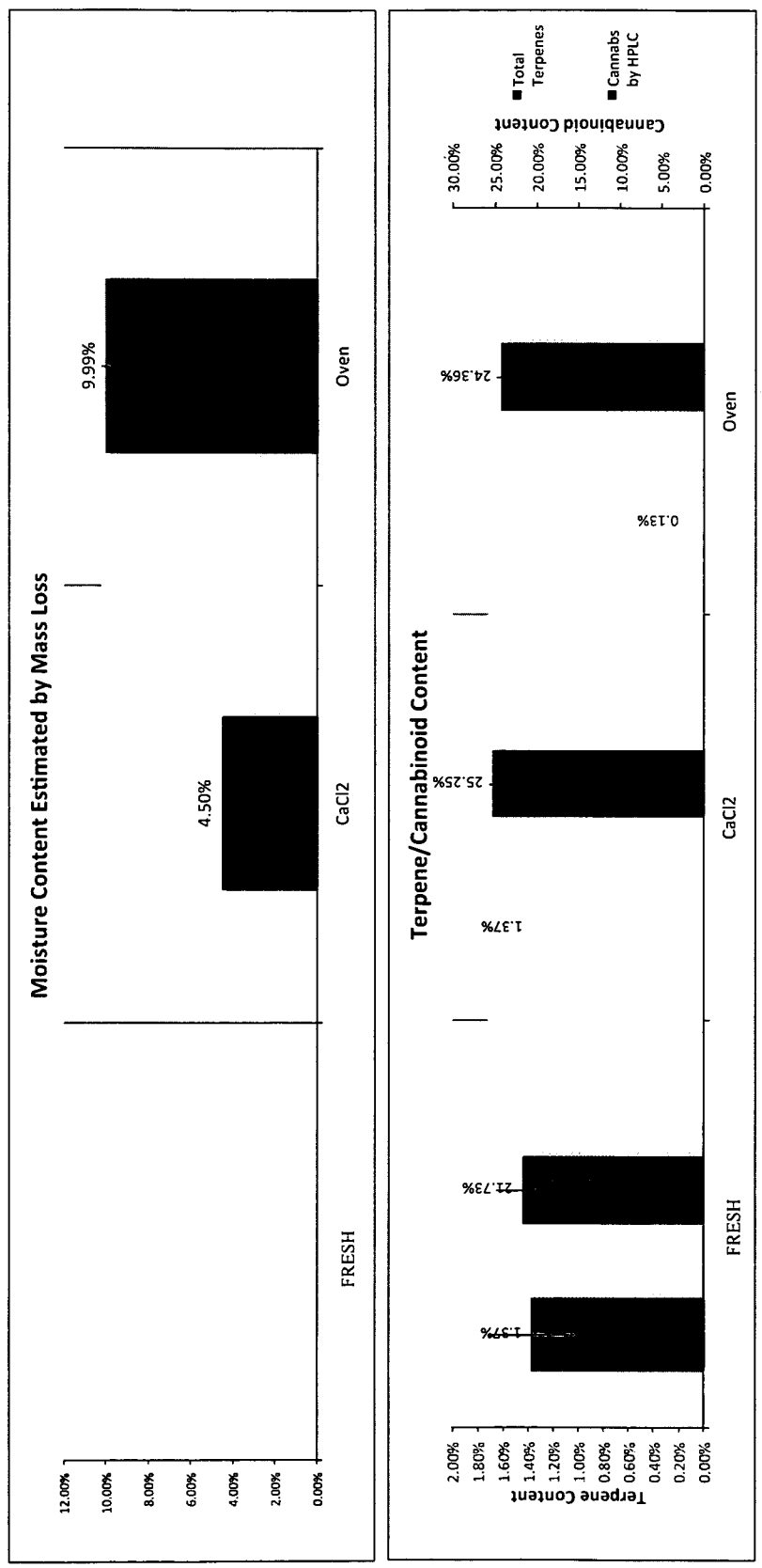
FIG. 28—Comparison of three identical cannabis samples processed by $CaCL_2$ chemical desiccation, traditional oven drying, or fresh finished flowers. Top chart shows measured weight loss as estimated moisture content. Bottom chart shows total terpene and cannabinoid contents as measured by GC-FID and HPLC, respectively. Samples are whole unground flowers.

Example 18—Comparison of Cannabinoid and Terpene Profiles for Oven-Dried and Chemically Desiccated Samples To test the effect of chemical desiccation and oven drying on analyte content, 1 g of whole finished flowers was placed over 20 g $CaCl_2$) for 96 hours ($CaCL_2$ treatment), and 1 g of whole finished flowers was placed in an oven at 105 C for 2 hours (Oven treatment). A third control "fresh" gram was immediately analyzed (Fresh control treatment). All samples in this example were analyzed for cannabinoid and terpene content using the HPLC and GC methods of the present disclosure. The experiment was conducted with three technical replicates for each treatment and control group. The results from these experiments are shown in FIG. 28, and also summarized below in Table 11.

TABLE 11

Terpene and Cannabinoid contents of Fresh Tissue Compared to Chemical Desiccation and Oven Drying.

| | Total Terpenes | | Cannabinoids by HPLC | |
|---|---|---|---|---|
| Sample | Wt % | 95% CI | WT % | 95% CI |
| Fresh | 1.37% | 0.35% | 21.73% | 3.04% |
| $CaCL_2$ | 1.37% | 0.04% | 25.25% | 0.39% |
| Oven | 0.13% | 0.01% | 24.36 | 0.43% |

Figure 29:
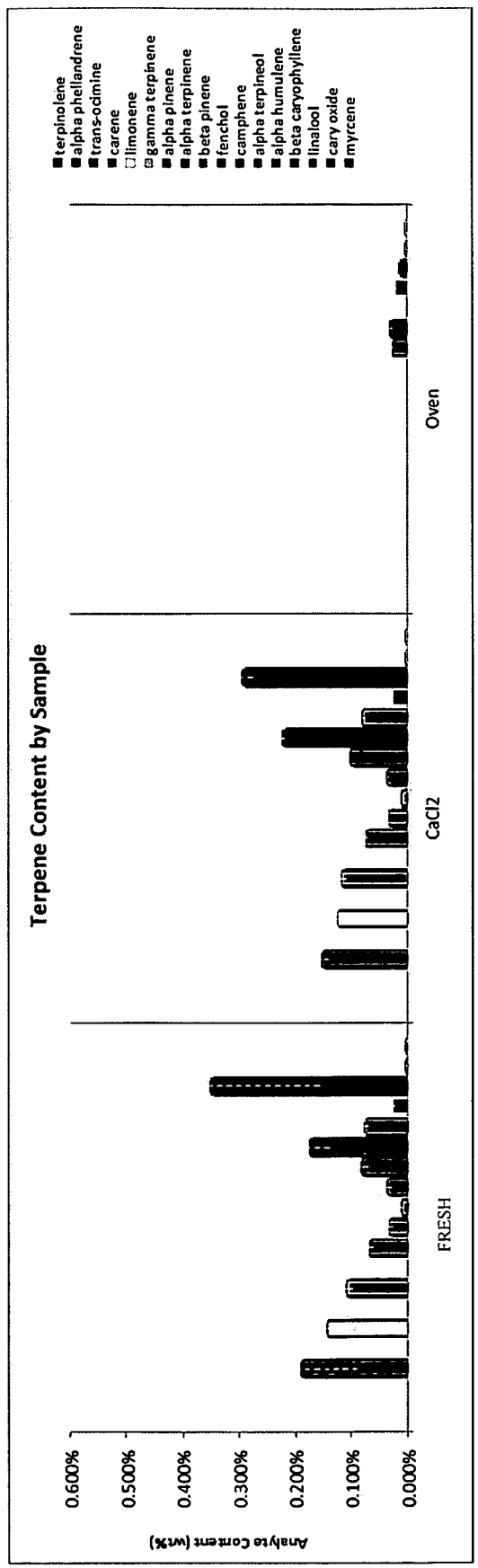
FIG. 29—GC-FID measured terpene profiles of three identical cannabis samples processed by $CaCL_2$ chemical desiccation, traditional oven drying, or fresh finished flowers. Top bar graph depicts visual representation of individual terpene contents. Bottom is a tabulated summary of measured terpene contents. Samples are w hole unground flowers.

These results suggest that the greater mass loss obtained from oven drying methods is largely due to loss of non-water volatile compounds. For example, FIG. 28 demonstrates that oven-dried samples lost 90% of the terpene content measured in fresh samples. Samples dried with chemical desiccants on the other hand, maintained equivalent terpene content as their fresh sample counterparts. FIG. 29 provides additional detail on the effect of chemical desiccation and oven drying on terpene profiles of cannabis samples. Results from this experiment demonstrate that chemically desiccated samples maintain similar terpene profiles to those measured from fresh samples, while oven dried samples lose nearly all terpene content.

Figure 30:
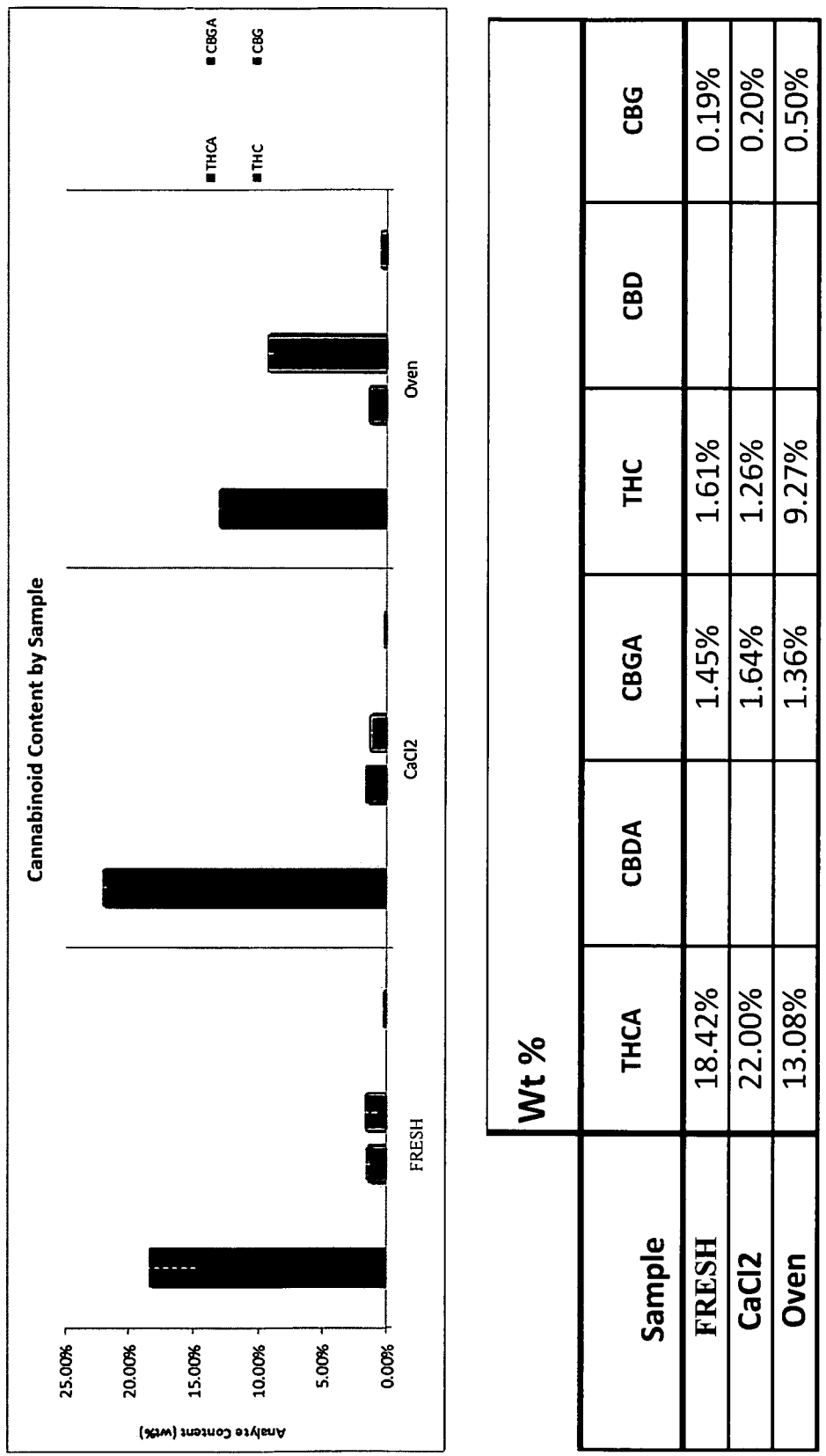
FIG. 30—HPLC measured cannabinoid profiles of three identical cannabis samples processed by $CaCL_2$ chemical desiccation, traditional oven drying, or fresh finished flowers. Top bar graph is a visual representation of individual cannabinoid contents. Bottom is a tabulated summary of measured cannabinoid contents. Blank value indicates undetectable levels. Samples are whole unground flowers. The cannabinoids from oven-dried samples have undergone significant decarboxylation.

FIG. 30 also compares changes in the cannabinoid profiles of chemically desiccated and oven-dried cannabis samples. Oven-dried samples exhibited signs of cannabinoid decarboxylation of THCA and CBGA to THC and CBG, respectively. Chemically desiccated samples on the other hand, maintained similar cannabinoid profiles as those of their fresh sample equivalents. Terpene loss and CO2 content loss from cannabinoid decarboxylation in the oven-dried sample accounts for nearly 3% of the mass loss.

The results of this example provide additional evidence that traditional oven-drying methods of sample drying overestimate moisture content and greatly affect terpene and cannabinoid contents of cannabis samples.

Example 19—Comparison of Different Chemical Desiccation Techniques on Ground Flower Tissue In this example, finished cannabis flower tissue was ground up in a stainless steel coffee grinder in order to increase the surface area of the flowers and speed desiccation.

Flower tissue from three different cultivars (PEVA, ACDC, and PCGA) were ground and one gram of each sample was placed in a container with 20 g of either $CaCL_2$ or $MgSO_4$ desiccant. A third gram of ground sample was placed in an oven at 105 C for 2 hours. Samples were weighed periodically, and mass loss was recorded. This experiment was repeated with three technical replicates for each cultivar and drying treatment.

Table 12 below summarizes the results of the experiment.

This experiment demonstrates that other chemical desiccants may be used for moisture quantification of cannabis samples. The results of Table 12 show that both $CaCL_2$ and $MgSO_4$ samples reach steady state weight within 24-48 hours. $MgSO_4$ appears to be a slightly weaker desiccant, as samples treated with $MgSO_4$ appear to retain 2% moisture over the equivalent $CaCl_2$ samples. This suggests even though each sample reached a constant mass on each desiccant, the strength and capacity of the desiccant can play a role in the final moisture content. Desiccation with $MgSO_4$ may require higher desiccant to sample ratios. Persons having skill in the art will recognize methods of determining optimum desiccant ratios. For example, via the experiments conducted in Example 16 of the present disclosure.

Figure 31:
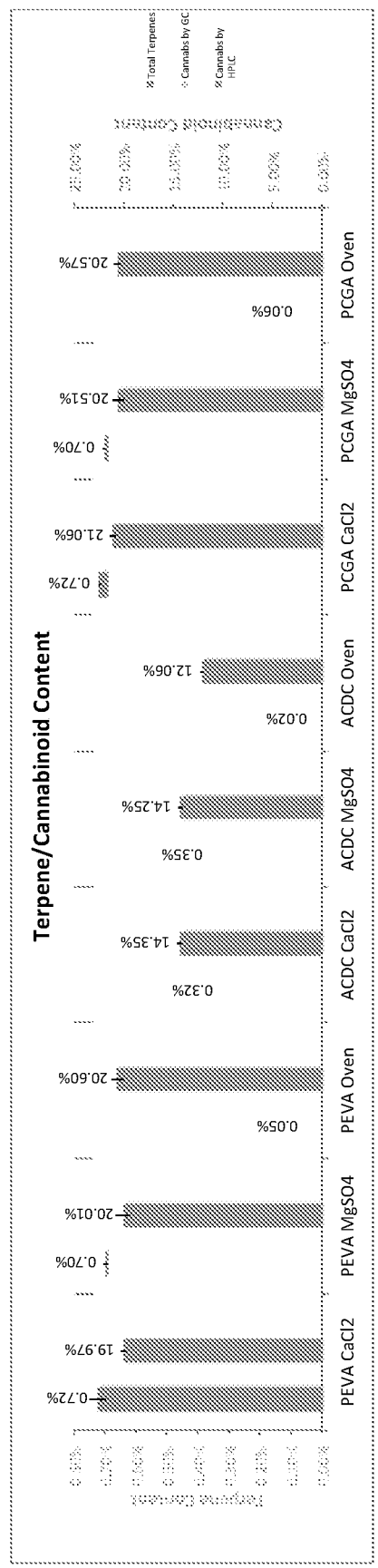
FIG. 31—Comparison of three identical cannabis samples processed by $CaCL_2$ chemical desiccation, $MgSO_4$ or traditional oven drying. The experiment was repeated for three cannabis varieties (PEVA, ACDC, and PCGA). Top chart shows total terpene and cannabinoid contents as measured by GC-FID and HPLC, respectively. Bottom is a tabulated summary of the cannabinoid and terpene contents used to construct the bar graph. Samples are ground flowers.

Desiccated samples as described above were analyzed using the cannabinoid and terpene analysis methods disclosed herein. FIG. 31 demonstrates that both $CaCL_2$ and $MgSO_4$ chemical desiccation techniques preserve the terpene contents of each of the tested samples. As was previously shown in Example 18, oven dried samples show a nearly complete loss of terpenes in all samples. The content of the terpenes measured in this Example are less than would normally be expected for these cultivars (typically 1.5-2%). This loss however is expected based on previous experiments, which demonstrated that grinding of samples ruptures trichomes and accelerates terpene loss. Shorter 24-36 hour chemical desiccations may reduce terpene loss from rupture trichomes. Alternatively, samples may be desiccated as whole flowers as performed in Example 18 of this disclosure.

Figure 32:
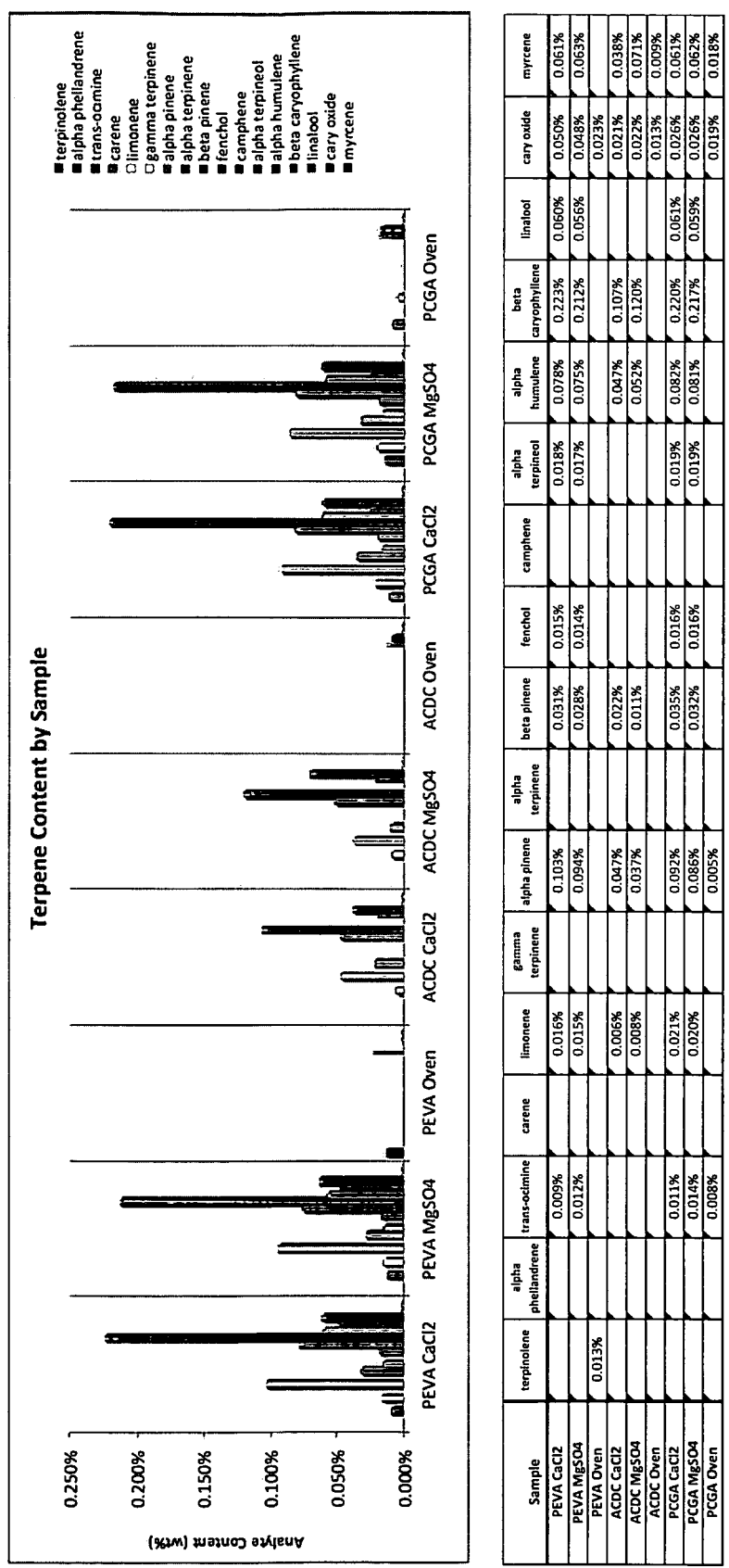
FIG. 32—GC-FID measured terpene profiles of three identical cannabis samples processed by $CaCL_2$ chemical desiccation. $MgSO_4$ or traditional oven drying. The experiment was repeated for three cannabis varieties (PEVA, ACDC, and PCGA). Top bar graph depicts visual representation of individual terpene contents. Bottom is a tabulated summary of measured terpene contents. Samples are ground flowers.

FIG. 32 shows the terpene profiles of chemically desiccated and oven dried samples. As previously reported in earlier examples, chemically desiccated samples maintained terpene diversity, while oven dried samples showed a nearly complete loss of terpenes.

Figure 33:
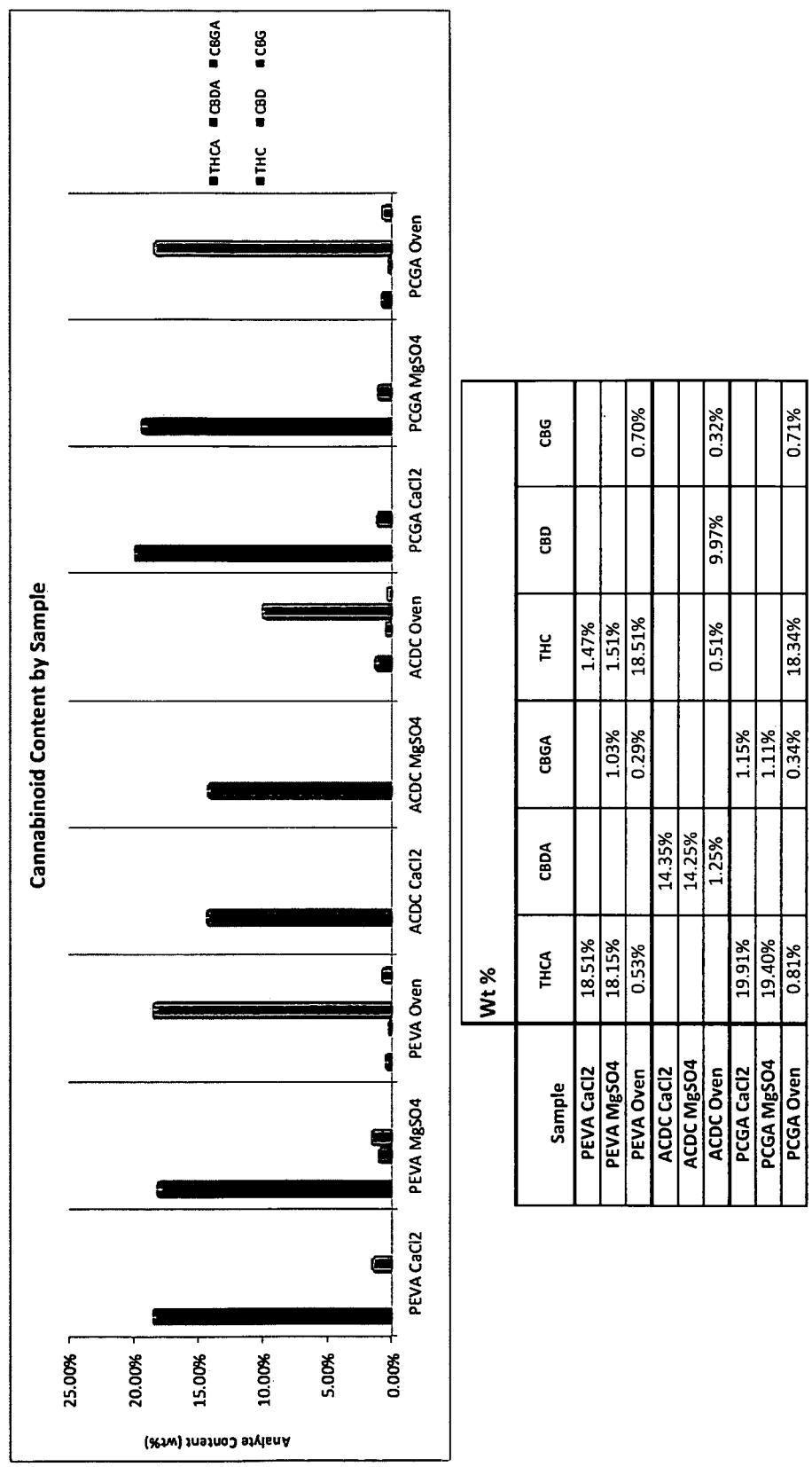
FIG. 33—HPLC measured cannabinoid profiles of three identical cannabis samples processed by $CaCL_2$ chemical desiccation. $MgSO_4$ or traditional oven drying. The experiment was repeated for three cannabis varieties (PEVA, ACDC, and PCGA). Top bar graph is a visual representation of individual cannabinoid contents. Bottom is a tabulated summary of measured cannabinoid contents. Blank value indicates undetectable levels. Samples are ground flowers. The cannabinoids from oven-dried samples have undergone significant decarboxylation.

FIG. 33 shows that oven-dried samples underwent cannabinoid decarboxylation of THCA, CBDA, and CBGA to THC, CBD, and CBG, respectively. Chemically desiccated samples on the other hand, maintained similar cannabinoid profiles as those of their fresh sample equivalents. Although

TABLE 12

Mass Loss of Ground Cannabis Tissue Dried with $CaCL_2$ or $MgSO_4$ Compared to Oven Drying.

| | | Sample | | | | | | | | |
|---|---|---|---|---|---|---|---|---|---|---|
| | | PEVA | | | ACDC | | | PCGA | | |
| | | Average | StDEV | RSD | Average | StDEV | RSD | Average | StDEV | RSD |
| CaCl2 | 24 h | 4.8% | 0.1% | 2.1% | 7.0% | 0.2% | 2.4% | 5.5% | 0.1% | 1.2% |
| | 48 h | 5.0% | 0.1% | 1.2% | 7.4% | 0.2% | 3.0% | 7.5% | 2.9% | 38.2% |
| | 72 h | 5.1% | 0.0% | 0.1% | 7.7% | 0.2% | 2.4% | 5.9% | 0.1% | 1.2% |
| | 96 h | | | | | | | | | |
| | 120 h | 5.2% | 0.1% | 1.2% | 7.8% | 0.2% | 1.9% | 5.9% | 0.1% | 1.1% |
| | 144 h | | | | | | | | | |
| | 168 h | | | | | | | | | |
| | 192 h | 5.4% | 0.1% | 1.1% | 8.0% | 0.2% | 3.0% | 6.1% | 0.1% | 2.0% |
| MgSO4 | 24 h | 3.5% | 0.1% | 3.1% | 5.4% | 0.1% | 1.2% | 4.0% | 0.1% | 2.7% |
| | 48 h | 3.8% | 0.1% | 2.9% | 5.7% | 0.1% | 1.2% | 4.2% | 0.2% | 3.9% |
| | 72 h | 3.8% | 0.1% | 2.9% | 5.9% | 0.1% | 1.8% | 4.3% | 0.1% | 3.3% |
| | 96 h | | | | | | | | | |
| | 120 h | 3.8% | 0.1% | 1.8% | 6.0% | 0.1% | 2.1% | 4.3% | 0.1% | 3.3% |
| | 144 h | | | | | | | | | |
| | 168 h | | | | | | | | | |
| | 192 h | 3.9% | 0.1% | 2.8% | 6.1% | 0.1% | 1.7% | 4.5% | 0.1% | 3.1% |
| | Oven | 12.0% | 2.5% | 20.4% | 14.4% | 0.1% | 1.0% | 13.4% | 0.1% | 0.7% | the total weight percent for each cannabinoid was similar for all treatments. FIG. 33 shows that that nearly complete decarboxylation occurred over 2 hours in the oven at 105 C. This results in a conversion of the acidic forms to the neutral forms by loss of $CO_2$.

If ~1000 mg of a sample contains ~20% THCA, this would correspond to a loss of approximately 26 mg of $CO_2$ upon decarboxylation. This is an additional mass loss of approximately 2.6% that is attributed to moisture loss after oven drying, when it is actually due to loss of $CO_2$. As described in this application, incorrect moisture measurements lead to incorrect analyte normalizations by weight.****

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

REFERENCES

1. ElSohly, M., & Gul, W. (2014) in Handbook of Cannabis, R. G. Pertwee (Eds), Oxford University Press, Oxford, UK, pp 3-22.
2. Russo, E. B. (2011) British Journal of Pharmacology 163, 1344-1364.
3. Hazekamp. A. (2007) in Cannabis: Extracting the Medicine, PrintPartners, Amsterdam, The Netherlands, pp 91-106.
4. Fishedick. J. T., Hazekamp, A., Erkelens, T., Choi. Y. H., Verpoorte, R. (2010) Phytochemistry 71, 2058-2073.
5. DeBacker, B., Debrus, B., Lebrun, P., Theunis, L., Dubois, N., Decock, L., Verstraete, A., Hubert, P., Charlier, C. (2009) Journal of Chromatography B 877, 4115-4124.
6. Swift. W., Wong, A., Li, K. M., Arnold. J. C., McGregor, I. S. (2013) PLOS ONE 8, 1-9.
7. American Herbal Pharmacopoeia, Cannabis Inflorescence and Leaf (2013), AHP, Scott's Valley, Calif.
8. Dussy, F. E., Hamberg, C., Luginbuhl, M., Schwerzmann, T., Briellmann, T. A. (2005) Forensic Science International 149, 3-10.
9. Restek ChromaBLOGraphy, http://blog.restek.com/?p=11770, accessed April 2014.
10. De Meijer, E. P. M., Bagatta, M., Carboni, A., Crucitti, P., Cristiana Moliterni, V. M., Ranalli, P., Mandolino, G. (2003) Genetics 163, 335-346.
11. Aberl, A., Coelhan, M. (2012) J. Agric. Food Chem. 60, 2785-2792.
12. Kulkarni, V. M., Rathod, V. K. (2014) Ultrason, Sonochem, 21, 606-11.
13. Burden, D. W. (2012) Random Primers 12, 1-25, http://opsdiagnostics.com/applicationsisamnplehomogenization/homogenizationguidepart1.html, accessed April 2013.
14. AOAC Peer-Verified Methods Program, Manual on policies and procedures (1998), Arlington, Va.
15. McPartland, J. M., Russo, E. B. (2001) Journal of Cannabis Therapeutics 1, 103-132.
16. Grotenherman, F. G. (2003). Journal of Cannabis Therapeutics, 3, 3-51.
17. Davies, H. V. et al (2010 Regulatory Toxicology and Pharmacology 58, S54-S61.
18. do Vale et al. (2002) Phytomedicine, 9, 709-714.
19. Rao et al. (2002) Journal of Pharmacy and Pharmacology 42, 877-878.
20. da Silva et al. (2012) Molecules, 17, 6305-16.

The invention claimed is:

1. A method for determining a concentration of at least one cannabinoid and at least one terpene in a test sample, the method comprising the steps of:
   a) extracting the test sample in an extraction solution, thereby producing an extracted test sample comprising the at least one cannabinoid and at least one terpene dissolved in the extraction solution, wherein the extraction solution comprises:
      i) a solvent;
      ii) a first internal standard with a known response ratio relative to the at least one cannabinoid;
      iii) a second internal standard with a known response ratio relative to the at least one terpene; and
      iv) a third internal standard;
   b) diluting the extracted test sample produced by step a) one or more times with a dilution solution; wherein said dilution solution comprises the solvent, the first internal standard, and the second internal standard, but not the third internal standard;
   c) subjecting the extracted test sample produced by step a), and/or the diluted test sample(s) produced by step b) to at least one chromatographic separation and detecting the separated sample(s) with at least one detector; and
   d) determining the concentration of the at least one cannabinoid and the at least one terpene in the test sample; wherein the concentration of the at least one cannabinoid in the test sample is normalized for dilution errors based on the concentration of the third internal standard in the diluted test sample(s) produced by step b).

2. The method of claim 1, wherein the at least one chromatographic separation is high performance liquid chromatography (HPLC).

3. The method of claim 2, wherein the at least one detector is a photodiode array detector.

4. The method of claim 1, wherein the at least one chromatographic separation is gas chromatography (GC).

5. The method of claim 4, wherein the at least one detector is a flame ionization detector.

6. The method of claim 1, wherein the at least one cannabinoid is selected from the group consisting of: tetrahydrocannabinolic acid (THCA), cannabidiolic acid (CBDA), tetrahydrocannabinol (THC), cannabidiol (CBD), cannabiserol (CBG), cannabichromene (CBC), and delta-8-tetrahydrocannabinol (delta-8 THC).

7. The method of claim 1, wherein the at least one cannabinoid is tetrahydrocannabinol (THC).

8. The method of claim 1, wherein the at least one terpene is selected from the group consisting of: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

9. The method of claim 1, wherein the solvent is ethanol.

10. The method of claim 1, wherein the first internal standard is ibuprofen.

11. The method of claim 1, wherein the second internal standard is n-nonane.

12. The method of claim 1, wherein the third internal standard is 4-biphenyl carboxylic acid (BPCA).

13. The method of claim 1, wherein the first internal standard is ibuprofen, the second internal standard is n-nonane, and the third internal standard is 4-biphenyl carboxylic acid.

14. A method for quantifying cannabinoids and terpenes from a test sample, said method comprising the steps of:
   a) extracting the test sample in an extraction solution, thereby producing an analytical extract comprising the cannabinoids and terpenes dissolved in the extraction solution, said extraction solution comprising:
      i. a solvent;
      ii. a first internal standard, and;
      iii. a second internal standard; and
   b) performing a high performance liquid chromatography (HPLC), and a gas chromatography-flame ionization detector (GC-FID) analysis of the analytical extract of step a) to produce a signal for at least one cannabinoid and at least one terpene, and to produce a signal for each of the standards;

wherein the signal for the at least one cannabinoid is normalized based on the signal from the first internal standard to quantify said at least one cannabinoid in the test sample, and wherein the signal for the at least one terpene is normalized based on the signal from the second internal standard to quantify said at least one terpene in the test sample; wherein the first internal standard is ibuprofen at a known concentration, and the second internal standard is n-nonane at a known concentration.

15. The method of claim 14 wherein the quantification of cannabinoids is performed via high performance liquid chromatography (HPLC).

16. The method of claim 14, wherein the quantification of terpenes is performed via gas chromatography-flame ionization detector (GC-FID).

17. The method of claim 14, wherein the analytical extract is diluted in a dilution solution prior to undergoing the high performance liquid chromatography (HPLC) and/or the gas chromatography-flame ionization detector (GC-FID) analysis of step b); wherein the extraction solution comprises a third internal standard, and wherein the dilution solution is identical to the extraction solution except for the presence of the third internal standard.

18. The method of claim 17, wherein the signal for the at least one cannabinoid is normalized based on the signal from the first internal standard and the third internal standard to quantify said at least one cannabinoid in the test sample, and/or wherein the signal for the at least one terpene is normalized based on the signal from the second internal standard and the third internal standard to quantify said at least one terpene in the test sample.

19. The method of claim 17, wherein the third internal standard is 4-biphenyl carboxylic acid (BPCA).

20. The method of claim 14, wherein the solvent is ethanol.

* * * * *